United States Patent
Molino

(10) Patent No.: US 7,696,166 B2
(45) Date of Patent: *Apr. 13, 2010

(54) USE OF CYCLOSPORIN ALKYNE/ALKENE ANALOGUES FOR PREVENTING OR TREATING VIRAL-INDUCED DISORDERS

(75) Inventor: Bruce F. Molino, Slingerlands, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/391,023

(22) Filed: Mar. 28, 2006

(65) Prior Publication Data

US 2007/0232531 A1    Oct. 4, 2007

(51) Int. Cl.
*A61K 38/12* (2006.01)
(52) U.S. Cl. .......................................... 514/11; 530/317
(58) Field of Classification Search .................. None
See application file for complete search history.

(56) References Cited

U.S. PATENT DOCUMENTS

| | | | |
|---|---|---|---|
| 4,210,581 A | 7/1980 | Rüegger et al. |
| 4,288,431 A | 9/1981 | Traber et al. |
| 4,384,996 A | 5/1983 | Bollinger et al. |
| 4,396,542 A | 8/1983 | Wenger |
| 4,554,351 A | 11/1985 | Wenger |
| 4,639,434 A | 1/1987 | Wenger et al. |
| 4,649,047 A | 3/1987 | Kaswan |
| 4,703,033 A | 10/1987 | Seebach |
| 4,727,035 A | 2/1988 | Mahoney |
| 4,764,503 A | 8/1988 | Wenger |
| 4,771,122 A | 9/1988 | Seebach |
| 4,798,823 A | 1/1989 | Witzel |
| 4,814,323 A | 3/1989 | Andrieu et al. |
| 4,839,342 A | 6/1989 | Kaswan |
| 4,885,276 A | 12/1989 | Witzel |
| 5,030,739 A | 7/1991 | Foricher et al. |
| 5,116,816 A | 5/1992 | Dreyfuss et al. |
| 5,169,773 A | 12/1992 | Rosenthaler et al. |
| 5,284,826 A | 2/1994 | Eberle |
| 5,318,901 A | 6/1994 | Patchett et al. |
| 5,411,952 A | 5/1995 | Kaswan |
| 5,525,590 A | 6/1996 | Bollinger et al. |
| 5,643,870 A | 7/1997 | Boelsterli et al. |
| 5,767,069 A | 6/1998 | Ko et al. |
| 5,834,266 A | 11/1998 | Crabtree et al. |

(Continued)

FOREIGN PATENT DOCUMENTS

| | | | |
|---|---|---|---|
| BR | 9603738-5 A | 5/1998 |
| CA | 1106303 A2 | 8/1981 |
| CA | 1292962 C | 12/1991 |
| CA | 2076291 AA | 2/1993 |
| CA | 2096892 A | 11/1993 |
| CA | 2086267 AA | 6/1994 |
| CH | 628872 A | 3/1982 |
| CH | 630061 A | 5/1982 |
| CH | 630062 A | 5/1982 |
| CH | 637123 A | 7/1983 |

(Continued)

OTHER PUBLICATIONS

The Merck Manual online version Oct. 27, 2004 www.merck/mmhe section 'Common cold' pp. 1-3.*

(Continued)

*Primary Examiner*—Anish Gupta
*Assistant Examiner*—Ronald T Niebauer
(74) *Attorney, Agent, or Firm*—Nixon Peabody LLP

(57) ABSTRACT

The present invention relates to methods of preventing or treating a mammal with a viral-induced disorder. The method involves administering to the mammal a therapeutically effective amount of a compound represented by Formula I, as shown below:

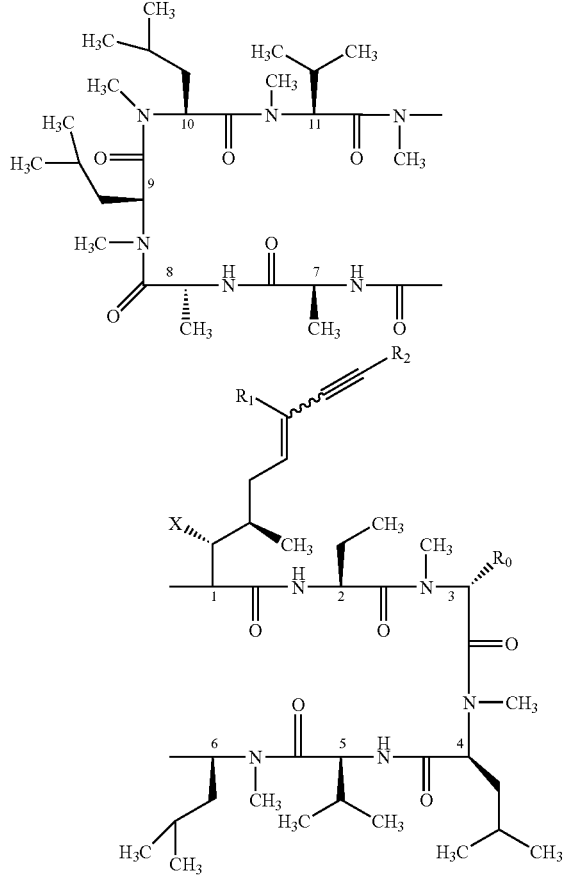

or a pharmaceutically acceptable salt thereof, with X, $R_0$, $R_1$, and $R_2$ defined herein, under conditions effective to prevent or treat the viral-induced disorder.

14 Claims, 1 Drawing Sheet

U.S. PATENT DOCUMENTS

| | | | |
|---|---|---|---|
| 5,840,900 | A | 11/1998 | Greenwald et al. |
| 5,846,514 | A | 12/1998 | Foster et al. |
| 5,869,337 | A | 2/1999 | Crabtree et al. |
| 5,869,709 | A | 2/1999 | Marwah et al. |
| 5,948,693 | A | 9/1999 | Rich et al. |
| 5,948,884 | A | 9/1999 | Luchinger |
| 5,981,479 | A | 11/1999 | Ko et al. |
| 5,994,299 | A | 11/1999 | Barriere et al. |
| 6,255,100 | B1 | 7/2001 | Ko et al. |
| 6,506,777 | B1 | 1/2003 | Finke et al. |
| 6,605,593 | B1 | 8/2003 | Naicker et al. |
| 6,613,739 | B1 | 9/2003 | Naicker et al. |
| 6,686,454 | B1 | 2/2004 | Yatscoff et al. |
| 6,723,339 | B2 | 4/2004 | Meinzer et al. |
| 6,767,555 | B2 | 7/2004 | Ambuhl et al. |
| 6,784,156 | B2 | 8/2004 | Or et al. |
| 6,809,077 | B2 | 10/2004 | Or et al. |
| 6,844,459 | B2 | 1/2005 | Hauer et al. |
| 6,927,208 | B1 | 8/2005 | Wenger et al. |
| 6,979,671 | B2 | 12/2005 | Or et al. |
| 6,998,385 | B2 | 2/2006 | Naicker et al. |
| 7,012,064 | B2 | 3/2006 | Or et al. |
| 7,012,065 | B2 | 3/2006 | Or et al. |
| 7,060,672 | B2 | 6/2006 | Naicker et al. |
| 2002/0127198 | A1 | 9/2002 | Rothbard et al. |
| 2002/0128470 | A1 | 9/2002 | Fuenfschilling et al. |
| 2002/0132763 | A1 | 9/2002 | Naicker et al. |
| 2002/0142946 | A1 | 10/2002 | Or et al. |
| 2003/0022831 | A1 | 1/2003 | Rothbard et al. |
| 2003/0087813 | A1 | 5/2003 | Or et al. |
| 2003/0104992 | A1 | 6/2003 | Or et al. |
| 2003/0109425 | A1 | 6/2003 | Or et al. |
| 2003/0109426 | A1 | 6/2003 | Or et al. |
| 2003/0139326 | A1 | 7/2003 | Naicker et al. |
| 2003/0166515 | A1 | 9/2003 | Or et al. |
| 2003/0171264 | A1 | 9/2003 | Naicker et al. |
| 2003/0186855 | A1 | 10/2003 | Or et al. |
| 2003/0212249 | A1 | 11/2003 | Naicker et al. |
| 2003/0220234 | A1 | 11/2003 | Naicker et al. |
| 2004/0087496 | A1 | 5/2004 | Kim et al. |
| 2004/0110666 | A1 | 6/2004 | Or et al. |
| 2004/0157768 | A1 | 8/2004 | Or et al. |
| 2004/0220091 | A1 | 11/2004 | Adam et al. |
| 2004/0235716 | A1 | 11/2004 | Molino et al. |
| 2004/0247624 | A1 | 12/2004 | Unger et al. |
| 2004/0266669 | A1 | 12/2004 | Wu et al. |
| 2005/0176628 | A1 | 8/2005 | Naicker et al. |
| 2005/0192214 | A1 | 9/2005 | Naicker et al. |
| 2006/0035821 | A1 | 2/2006 | Hunt et al. |
| 2006/0035822 | A1 | 2/2006 | Hunt et al. |
| 2006/0035828 | A1 | 2/2006 | Elmaleh |
| 2006/0052290 | A1 | 3/2006 | Naicker et al. |
| 2006/0069015 | A1 | 3/2006 | Molino et al. |
| 2006/0069016 | A1* | 3/2006 | Molino et al. ................. 514/9 |
| 2006/0074015 | A1 | 4/2006 | Molino et al. |
| 2006/0135414 | A1 | 6/2006 | Naicker et al. |
| 2006/0217309 | A1 | 9/2006 | Naicker et al. |
| 2007/0232530 | A1 | 10/2007 | Molino |
| 2007/0232532 | A1 | 10/2007 | Molino |
| 2008/0021197 | A1 | 1/2008 | Molino et al. |
| 2008/0153744 | A1 | 6/2008 | Molino et al. |
| 2008/0249002 | A1* | 10/2008 | Molino et al. ................. 514/11 |

FOREIGN PATENT DOCUMENTS

| | | | |
|---|---|---|---|
| CH | 640520 | A | 1/1984 |
| CS | 277471 | B6 | 3/1993 |
| CS | 277472 | B6 | 3/1993 |
| CZ | 280552 | B6 | 2/1996 |
| CZ | 280553 | B6 | 2/1996 |
| DD | 285793 | A5 | 1/1991 |
| DD | 295245 | A5 | 10/1991 |
| DD | 295870 | A | 11/1991 |
| DD | 295871 | A | 11/1991 |
| DE | 2455859 | A1 | 6/1975 |
| DE | 2648121 | A1 | 5/1977 |
| DE | 2819094 | A1 | 11/1978 |
| DE | 4032268 | A1 | 4/1992 |
| DE | 4236237 | A1 | 4/1994 |
| DE | 19933173 | A1 | 1/2001 |
| DE | 102004011988 | A1 | 9/2005 |
| EP | 0 034 567 | | 11/1984 |
| EP | 283801 | A2 | 9/1988 |
| EP | 300785 | A2 | 1/1989 |
| EP | 375454 | A1 | 6/1990 |
| EP | 444897 | A1 | 9/1991 |
| EP | 471295 | A1 | 2/1992 |
| EP | 473961 | A2 | 3/1992 |
| EP | 487289 | A2 | 5/1992 |
| EP | 642799 | A1 | 3/1995 |
| EP | 0 484 281 | B2 | 11/2000 |
| FR | 2640641 | A1 | 6/1990 |
| FR | 2757520 | A1 | 6/1998 |
| FR | 2757521 | A1 | 6/1998 |
| FR | 2757522 | A1 | 6/1998 |
| FR | 2851471 | A1 | 8/2004 |
| GB | 2205317 | A1 | 12/1988 |
| GB | 2206119 | A1 | 12/1988 |
| GB | 2207678 | A1 | 2/1989 |
| GB | 2212499 | A1 | 7/1989 |
| GB | 2227244 | A1 | 7/1990 |
| JP | 57063093 | A2 | 4/1982 |
| JP | 05271267 | A2 | 10/1993 |
| JP | 07278187 | A2 | 10/1995 |
| JP | 10279596 | A2 | 10/1998 |
| JP | 2002080394 | A2 | 3/2002 |
| JP | 2005198543 | A2 | 7/2005 |
| JP | 2005325061 | A2 | 11/2005 |
| KR | 161664 | B1 | 11/1998 |
| KR | 2002089300 | A | 11/2002 |
| RU | 2144017 | C1 | 1/2000 |
| WO | WO 90/06763 | | 6/1990 |
| WO | WO 92/06998 | | 4/1992 |
| WO | WO 92/13094 | | 8/1992 |
| WO | WO 92/13569 | | 8/1992 |
| WO | WO 93/07150 | | 4/1993 |
| WO | WO 94/18317 | | 8/1994 |
| WO | WO 94/25606 | | 11/1994 |
| WO | WO 95/02684 | | 1/1995 |
| WO | WO 96/06111 | | 2/1996 |
| WO | WO 96/06857 | | 3/1996 |
| WO | WO 96/27607 | | 9/1996 |
| WO | WO 96/40758 | | 12/1996 |
| WO | WO 97/04005 | | 2/1997 |
| WO | WO 97/11092 | | 3/1997 |
| WO | WO 97/46575 | | 12/1997 |
| WO | WO 98/03192 | | 1/1998 |
| WO | WO 98/07713 | | 2/1998 |
| WO | WO 98/08956 | | 3/1998 |
| WO | WO 98/46247 | | 10/1998 |
| WO | WO 98/49193 | | 11/1998 |
| WO | WO 98/58927 | | 12/1998 |
| WO | WO 99/02659 | | 1/1999 |
| WO | WO 99/10373 | | 3/1999 |
| WO | WO 99/10374 | | 3/1999 |
| WO | WO 99/18120 | | 4/1999 |
| WO | WO 99/21879 | | 5/1999 |
| WO | WO 99/32512 | | 7/1999 |
| WO | WO 99/62540 | | 12/1999 |
| WO | WO 99/65933 | | 12/1999 |
| WO | WO 99/67280 | | 12/1999 |
| WO | WO 00/01715 | | 1/2000 |
| WO | WO 00/08033 | | 2/2000 |
| WO | WO 00/51558 | | 9/2000 |

| | | |
|---|---|---|
| WO | WO 00/67801 | 11/2000 |
| WO | WO 01/05819 A1 | 1/2001 |
| WO | WO 01/13957 A2 | 3/2001 |
| WO | WO 01/35913 A1 | 5/2001 |
| WO | WO 01/35914 A1 | 5/2001 |
| WO | WO 02/24865 A2 | 3/2002 |
| WO | WO 02/41858 A1 | 5/2002 |
| WO | WO 02/41859 A1 | 5/2002 |
| WO | WO 02/064106 A1 | 8/2002 |
| WO | WO 02/065986 A2 | 8/2002 |
| WO | WO 02/067917 A1 | 9/2002 |
| WO | WO 02/069902 A2 | 9/2002 |
| WO | WO 02/076927 A2 | 10/2002 |
| WO | WO 02/085928 A2 | 10/2002 |
| WO | WO 02/092032 A1 | 11/2002 |
| WO | WO 02/092033 A1 | 11/2002 |
| WO | 02/100428 A1 | 12/2002 |
| WO | WO 03/030834 A2 | 4/2003 |
| WO | WO 03/032949 A1 | 4/2003 |
| WO | WO 03/033010 A1 | 4/2003 |
| WO | WO 03/033526 A2 | 4/2003 |
| WO | WO 03/033527 A2 | 4/2003 |
| WO | WO 03/034980 A1 | 5/2003 |
| WO | WO 03/049772 A1 | 6/2003 |
| WO | WO 03/070755 A2 | 8/2003 |
| WO | WO 2004/050687 A2 | 6/2004 |
| WO | WO 2004/072108 A1 | 8/2004 |
| WO | WO 2004/082629 A1 | 9/2004 |
| WO | WO 2004/089960 A2 | 10/2004 |
| WO | WO 2004/096236 A1 | 11/2004 |
| WO | WO 2004/100960 A1 | 11/2004 |
| WO | WO 2005/000879 A1 | 1/2005 |
| WO | WO 2005/021028 A1 | 3/2005 |
| WO | WO 2005/046575 A2 | 5/2005 |
| WO | WO 2005/097164 A2 | 10/2005 |
| WO | WO 2006/005580 A1 | 1/2006 |
| WO | WO 2006/005610 A1 | 1/2006 |
| WO | WO 2006/014872 A1 | 2/2006 |
| WO | 2006/039163 A2 | 4/2006 |
| WO | 2006/039164 A2 | 4/2006 |
| WO | 2006/041631 A2 | 4/2006 |
| WO | WO 2006/063470 A1 | 6/2006 |
| WO | WO 2006/066416 A1 | 6/2006 |
| WO | WO 2006/071618 A1 | 7/2006 |
| WO | 2007/112345 A2 | 10/2006 |
| WO | 2007/112352 A2 | 10/2006 |
| WO | 2007/112357 A2 | 10/2006 |

OTHER PUBLICATIONS

The Merck Manual online version Mar. 20, 2005 www.merck.com/mmhe section 'Viral infections' pp. 1-4.*
Chakrabarty et al., 2004, Dermatologic Therapy, v17 pp. 465-490.*
Abel et al., "ISATX247: A Novel Calcineurin Inhibitor," *J. Heart Lung Transplant.* 20(2):161 (2001) (Abstract 36).
Aspeslet et al., "ISA$_{TX}$ 247: A Novel Calcineurin Inhibitor," *Transplant. Proc.* 33:1048-1051 (2001).
Buetler et al., "Does Cyclosporin A Generate Free Radicals?" *TIPS* 21:288-290 (2000).
Christians & Sewing, "Cyclosporin Metabolism in Transplant Patients," *Pharmac. Ther.* 57:291-345 (1993).
Clark & Yorio, "Ophthalmic Drug Discovery," *Nat. Rev. Drug Discov.* 2(6):448-459 (2003).
Dumont, "ISAtx-247 Isotechnilca/Roche," *Curr. Opin. Investig. Drugs* 5(5):542-550 (2004).
Eberle et al., "Preparation of Sulfhydryl Cyclosporin A," *J. Org. Chem.* 60:2610-2612 (1995).
Eckstein & Fung, "A New Class of Cyclosporin Analogues for the Treatment of Asthma," *Expert Opin. Investig. Drugs* 12(4):647-653 (2003).
Foster, "Deuterium Isotope Effects in Studies of Drug Metabolism," *Tips* 5:524-527 (1984).
Fritz-Langhals & Kunath, "Synthesis of Aromatic Aldehydes by Laccase-Mediator Assisted Oxidation," *Tetrahedron Lett.* 39:5955-5956 (1998).
Henke et al., "Cyclosporine A Inhibits ATP Net Uptake of Rat Kidney Mitochondria," *Biochem. Pharmacol.* 43(5):1021-1024 (1992).
Kallen et al., "12 Cyclosporins. : Recent Developments in Biosynthesis, Pharmacology and Biology, and Clinical Applications," *Biotechnology*, Second Edition, Rehm et al, eds., pp. 535-591 (1997).
Khanna et al., "TGF-β: A Link Between Immunosuppression, Nephrotoxicity, and CsA," *Transplant. Proc.* 30:944-945 (1998).
Ko & Wenger, "53. Solid-Phase Total Synthesis of Cyclosporine Analogues," *Helvetica Chimica Acta* 80:695-705 (1997).
Lazarova et al., "Synthesis and Biological Evaluation of Novel Cyclosporin A Analogues: Potential Soft Drugs for the Treatment of Autoimmune Diseases," *J. Med. Chem.* 46:674-676 (2003).
Loor, "Cyclosporins and Related Fungal Products in the Reversal of P-Glycoprotein-Mediated Multidrug Resistance," in *Multidrug Resistance in Cancer Cells* Gupta et al, eds., John Wiley and Sons Ltd: Chichester, pp. 385-412 (1996).
Loor, "Valspodar: Current Status and Perspectives," *Exp. Opin. Invest. Drugs* 8(6):807-835 (1999).
Mlynar et al., "The Non-Immunosuppressive Cyclosporin A Analogue SDZ NIM 811 Inhibits Cyclophilin A Incorporation Into Virions and Virus Replication in Human Immunodeficiency Virus Type 1-Infected Primary and Growth-Arrested T Cells," *J. Gen. Virol.* 78(4):825-835 (1997).
Offenzeller et al., "Biosynthesis of the Unusual Amino Acid (4R)-4-[(E)-2-Butenyl]-4-methyl-$_L$-threonine of Cyclosporin A: Enzymatic Analysis of the Reaction Sequence Including Identification of the Methylation Precursor in a Polyketide Pathway," *Biochem.* 35:8401-8412 (1996).
Paolini, "Cyclosporin A and Free Radical Generation," *TIPS* 22(1):14-15 (2001).
Park & Meier, "A Semi-Synthetic Approach to Olefinic Analogs of Amino Acid One (MeBMT) in Cyclosporin A," *Tetrahedron Lett.* 30(32):4215-4218 (1989).
Potthast et al., "A Novel Method for the Conversion of Benzyl Alcohols to Benzaldehydes by Laccase-Catalyzed Oxidation," *J. Mol. Catalysis A* 108:5-9 (1996).
Punniyamurthy & Iqbal, "Cobalt Catalysed Allylic and Benzylic Oxidations with Dioxygen in the Presence of Ethyl 2-Oxocyclopentanecarboxylate," *Tetrahedron Lett.* 35(23):4003-4006 (1994).
Seebach et al., "Modification of Cyclosporin A (CS): Generation of an Enolate at the Sarcosine Residue and Reactions with Electrophiles," *Helvetica Chimica Acta* 76:1564-1590 (1993).
Seebach & Ko, "Thiocyclosporins: Preparation, Solution and Crystal Structure, and Immunosuppressive Activity," *Helvetica Chimica Acta* 74:1953-1990 (1991).
Serino et al., "Oxygen Radical Formation by the Cytochrome P450 System as a Cellular Mechanism for Cyclosporine Toxicity," *Transplant. Proc.* 26:2916-2917 (1994).
Serkova et al., "The Novel Immunosuppressant SDZ-RAD Protects Rat Brain Slices from Cyclosporine-Induced Reduction of High-Energy Phosphates," *Br. J. Pharmacol.* 129:485-492 (2000).
Snyder & Sabatini, "Immunophilins and the Nervous System," *Nat. Med.* 1(1):32-37 (1995).
Snyder et al., "Neural Actions of Immunophilin Ligands," *TIPS* 19:21-26 (1998).
Steiner et al., "Neurotrophic Actions of Nonimmunosuppressive Analogues of Immunosuppressive Drugs FK506, Rapamycin and Cyclosporin A," *Nat. Med.*3(4):421-428 (1997).
Traber et al., "Cyclosporins-New Analogues by Precursor Directed Biosynthesis," *J. Antibiotics* 42(4):591-597 (1989).
Traber et al., "122. Die Struktur von Cyclosporin C," *Helvetica Chimica Acta* 60(4):1247-1255 (1977) (English Abstract Only).
Traber et al., "162. Isolierung und Strukturermittlung der neuen Cyclosporine E, F, G, H und I," *Helvetica Chimica Acta* 65(5):1655-1677 (1982) (English Abstract Only).
Traber et al., "2. Neue Cyclosporine aus *Tolypocladium inflatum* Die Cyclosporine K-Z," *Helvetica Chimica Acta* 70:13-36 (1987) (English Abstract Only).

Wenger, "60. Synthesis of Cyclosporine: Total Syntheses of 'Cyclosporin A' and 'Cyclosporin H', Two Fungal Metabolites Isolated from the Species *Tolypocladium Inflatum G$_{AMS}$*," Helvetica Chimica Acta 67(2):502-525 (1984).

Wenger, "Structures of Cyclosporine and Its Metabolites," *Transplant. Proc.* 22(3):1104-1108 (1990).

Xu et al., "Redox Chemistry in Laccase-Catalyzed Oxidation of N-Hydroxy Compounds," *Appl. Environ. Microbiol.* 66(5):2052-2056 (2000).

Aebi et al., "Synthesis, Conformation, and Immunosuppressive Activities of Three Analogs of Cyclosporin A Modified in the 1-Position," *Journal of Medicinal Chemistry* 33(3):999-1009 (1990), Abstract only.

Agathos et al., "Enhancement of Cyclosporin Production in a *Tolypocladium inflatum* Strain After Epichlorohydrin Treatment," *Journal of Biotechnology* 13(1):73-81 (1990), Abstract onl y.

Agathos et al., "The Fungal Production of Cyclosporins," *Annals of the New York Academy of Sciences*, 506(Biochem. Eng. 5):657-662 (1987), Abstract only.

Alberg et al., "Structure-Based Design of a Cyclophilin-Calcineurin Bridging Ligand," *Science* (Washington, DC, United States) 262(5131):248-250 (1993), Abstract only.

Andres et al., "Interaction of Lead(II) With Highly-Dentate Linear and Cyclic Polyamines," *Journal of the Chemical Society, Dalton Transactions: Inorganic Chemistry* (23):3507-3513 (1972-1999) (1993), Abstract only.

Angell et al. "Innovation and Perspectives in Solid Phase Synthesis & Combinatorial Libraries: Peptides, Proteins and Nucleic Acids—Small Molecule Organic Chemical Diversity, Collected Papers," in Epton, ed. *International Symposium*, 5th, London, Sep. 2-6, 1997 (1999), Meeting Date 1997, Mayflower Scientific Ltd.: Kingswinford, pp. 135-138, Abstract only.

Angell et al., "Solid-Phase Synthesis of Cyclosporin Peptides," *Journal of the American Chemical Society* 117(27):7279-7280 (1995), Abstract only.

Angell, "The Solid-Phase Synthesis Of Cyclosporin A Analogs," Diss. Abstr. Int., B 1997, 57(9):5657(1996), Abstract only.

Belshaw et al. "Cell-Specific Calcineurin Inhibition by a Modified Cyclosporin," *Journal of the American Chemical Society* 119(7):1805-1806 (1997), Abstract only.

Belshaw et al., "Controlling Protein Association and Subcellular Localization With a Synthetic Ligand That Induces Heterodimerization of Proteins," *Proceedings of the National Academy of Sciences of the United States of America*, 93(10):4604-4607 (1996), Abstract only.

Belshaw et al., "Rational Design of Orthogonal Receptor-Ligand Combinations," *Angewandte Chemie, International Edition in English*, 34(19):2129-2132 (1995), Abstract only.

Bencini et al., "Anaerobic Complexation of Cobalt(II) by [3k]aneNk (k=7-12) Polyazacycloalkanes," *Inorganic Chemistry* 28(12):2480-2482 (1989), Abstract only.

Bencini et al., "Synthesis and Ligational Properties of the Two Very Large Polyazacycloalkanes [33]aneN11 and [36]aneN12 Forming Trinuclear Copper(II) Complexes," *Inorganic Chemistry* 27(1):176-180 (1988), Abstract only.

Bencini et al., "Thermodynamic and Structural Aspects of the Interaction Between Macrocyclic Polyammonium Cations and Complexed Anions," *Inorganic Chemistry* 31(10):1902-1908 (1992), Abstract only.

Billich et al., Enzymic Synthesis of Cyclosporin A,: *Journal of Biological Chemistry* 262(36):17258-17259 (1987), Abstract only.

Billich et al., "Novel Cyclosporin Derivatives Featuring Enhanced Skin Penetration Despite Increased Molecular Weight," *Bioorganic and Medicinal Chemistry* 13(9):3157-3167 (2005), Abstract only.

Bohnstedt, "The Synthesis And Biological Activities Of Novel Backbone-Modified Analogs of Cyclosporin A," Diss. Abstr. Int. B 1995, 55(11), 4848 (1994), Abstract only.

Brooks et al., "Preparative Chromatographic Purification of Cyclosporine Metabolites," *Clinical Chemistry* (Washington, DC, United States) 39(3):457-466 (1993), Abstract only.

Brugghe et al., "Simultaneous Multiple Synthesis and Selective Conjugation of Cyclized Peptides Derived from a Surface Loop of a Meningococcal Class 1 Outer Membrane Protein," *International Journal of Peptide & Protein Research* 43(2), 166-172 (1994), Abstract only.

Buchta et al., "A Cyclosporin From *Mycelium sterilae*," *Phytochemistry* 48(7):1195-1198 (1998), Abstract only.

Burtscher et al., "Synthesis of [S-[1-14C]val7]VALSPODAR: Application of (+)/(-31 )-[13,14Cn]BABS and (+)/(-)-[13,14Cn]DPMGBS," *Journal of Labelled Compounds & Radiopharmaceuticals* 43(3):205-216 (2000), Abstract only.

Cacalano et al., "Antibodies to Cyclosporine a (CsA) by a Novel Route and Their Use to Monitor Cyclosporine Levels by Radioimmunoassay (RIA)," *Journal of Immunological Methods* 118(2):257-263 (1989), Abstract only.

Carry et al., "Semisynthetic Di- and Tri-Functionalized Non-Immunosuppressive Cyclosporin A Derivatives as Potential Anti-HIV 1 Drugs," *Synlett* (2):316-320 (2004), Abstract only.

Cerny et al., "Synthesis of [ω-3H-MeBmt1]-Cyclosporin A," *Journal of Labelled Compounds & Radiopharmaceuticals* 41(4):267-272 (1998), Abstract only.

Chen et al., "A Sensitive Enzyme Immunoassay for Cyclosporin A Using Antibodies Generated Against a Novel Hapten," *Research Communications in Molecular Pathology and Pharmacology* 88(3):317-326 (1995), Abstract only.

Cho et al., "Water Soluble Cyclosporine Monomethoxy Poly(Ethyleneglycol) Conjugates as Potential Prodrugs," *Archives of Pharmacal Research* 27(6):662-669 (2004), Abstract only.

Chu et al., "A New Producer of Cyclosporin C," *Zhongguo. Kangshengsu Zazhi* 23(1):1-5, 16 (1998), Abstract only.

Chu et al., "Production of Cyclosporin C by Gliomastix luzulae Isolated From Different Areas of China," *Zhongguo Kangshengsu Zazhi* 23(2):116-120 (1998), Abstract only.

Chu et al., "Screening of Antifungal Substances with Immunosuppressive Activity by Special Morphological Abnormalities of *Aspergillus clavatus*," *Zhongguo Kangshengsu Zazhi* 23(3):193-196 (1998), Abstract only.

Coates et al., "Radioimmunoassay of Salivary Cyclosporine With Use of Iodine-125-Labeled Cyclosporine," *Clinical Chemistry* (Washington, DC, United States), 34(8):1545-1551 (1988), Abstract only.

Colucci et al., "Synthesis of D-Lysine8-Cyclosporine A. Further Characterization of Bop-Cl in the 2-7 Hexapeptide Fragment Synthesis," *Journal of Organic Chemistry* 55(9): 2895-2903 (1990), Abstract only.

Dai et al., "Study of the Reaction Between Cyclosporine A and 4-Benzoylbenzoic Acid," *Jingxi Huagong* 18(3):135-137 (2001), Abstract only.

Donatsch et al., "A Radioimmunoassay to Measure Cyclosporin A in Plasma and Serum Samples," *Journal of Immunoassay* 2(1): 19-32 (1981), Abstract only.

Dreyfuss et al., "Cyclosporin A and C. New Metabolites From *Trichoderma polysporum* (Link ex Pers.) Rifai," *European Journal of Applied Microbiology* 3(2):125-133 (1976), Abstract only.

Dugave, "Study of the cis-trans Isomerization of the Amino-Acyl Prolyl Peptide Bond: Application to the Design of Novel Inhibitors of Immunophilins," *Current Organic Chemistry* 6(15):1397-1431 (2002), Abstract only.

Durette et al., "A study of the Correlation Between Cyclophilin Binding and in Vitro Immunosuppressive Activity of Cyclosporine A and Analogs," *Transplantation Proceedings* 20(2, Suppl. 2):51-57 (1988), Abstract only.

Eberle et al., "Bridged Cyclosporins," *Journal of Organic Chemistry* 60(15):4868-4872 (1995), Abstract only.

Eberle et al., "Cyclosporin A: Regioselective Ring Opening and Fragmentation Reactions via Thioamides. A Route to Semisynthetic Cyclosporins," *Journal of Organic Chemistry* 59(24): 7249-7258 (1994), Abstract only.

Eberle et al., "Modifications of the MeBmt Side Chain of Cyclosporin A," *Bioorganic & Medicinal Chemistry Letters* 5(15):1725-1728 (1995), Abstract only.

Eberle et al., "Preparation and in Vitro Activities of Ethers of [D-Serine]8-cyclosporin," *Journal of Medicinal Chemistry* 38(11):1853-1864 (1995), Abstract only.

Eberle et al., "Preparation of [D-cysteine]8-Cyclosporin Via Intramolecular Sulfur Transfer Reaction," *Journal of Organic Chemistry* 58(3):673-677 (1993), Abstract only.

Eberle et al., "Preparation of Functionalized Ethers of Cyclosporin A," *Tetrahedron Letters* 35(35):6477-6480 (1994), Abstract only.

Eberle et al., "Synthesis of the Main Metabolite (OL-17) of Cyclosporin A," *Journal of Organic Chemistry*, 57(9):2689-2691 (1992), Abstract only.

Endo et al., "Solution-Phase Synthesis and Structural Analysis of N-Desmethylated Cyclosporin O Analogs," *Peptide Science* 39:383-386 Volume Date 2002, (2003), Abstract only.

Evers et al., "Synthesis of Non-Immunosuppressive Cyclophilin-Binding Cyclosporin A Derivatives as Potential Anti-HIV-1 Drugs," *Bioorganic & Medicinal Chemistry Letters* 13 (24): 4415-4419 (2003), Abstract only.

Fang et al., "Separation of Cyclosporins by High Speed Counter Current Chromatography," *Zhongguo Kangshengsu Zazhi* 30(1):48-51 (2005), Abstract only.

French et al., "New Fluorescent Derivatives of Cyclosporin for Use in Immunoassays," *Journal of Pharmaceutical and Biomedical Analysis* 10(1):23-30 (1992), Abstract only.

Galpin et al., "Synthesis of Cyclosporin Analogs," *Tetrahedron Letters* 28(51):6517-6520 (1987), Abstract only.

Galpin et al., "Synthetic Studies of Cyclosporin Analogs," *Tetrahedron* 44(6):1783-1794 (1988), Abstract only.

Gfeller et al., "Improvement of Detection Sensitivity of Cyclosporin A by Derivatization With 2-Naphthylselenyl Chloride," *Helvetica Chimica Acta* 63(3):728-732 (1980), Abstract only.

Giger et al., "Design and Synthesis of a Transition State Analog of a Metalloporphyrin-Catalysed Oxidation Reaction," *Journal of Porphyrins and Phthalocyanines* 6(5):362-365 (2002), Abstract only.

Grote et al. "A Practical Method for the Synthesis of a Cyclosporine-Fluorescein Conjugate," *Organic Process Research & Development*, 9(6):822-824 (2005), Abstract only.

Guichou et al., "Pseudo-Prolines (ψPro): Direct Insertion of ψPro Systems Into Cysteine Containing Peptides," *Tetrahedron Letters* 43(24):4389-4390 (2002), Abstract only.

Hamel et al., "Cyclosporin A Prodrugs: Design, Synthesis and Biophysical Properties," *Journal of Peptide Research* 63(2):147-154 (2004), Abstract only.

Hamel et al., "Water-Soluble Prodrugs of Cyclosporine A With Tailored Conversion Rates," *Journal of Peptide Research* 65(3):364-374 (2005), Abstract only.

Hensens et al., "The Preparation of [2-deutero-3-fluoro-D-Ala8]Cyclosporin A by Directed Biosynthesis," *Journal of Antibiotics* 45(1):133-135 (1992), Abstract only.

Hornich et al., "Variation of Amino Acids Within the Cyclosporin-Cyclophilin Binding Domain. Synthesis of a 21-Membered Cyclopeptolide," *Scientia Pharmaceutica* 64(3/4):463-470 (1996), Abstract only.

Hu et al., "Cyclosporin Analogs Modified in the 3,7,8-Positions: Substituent Effects on Peptidylprolyl Isomerase Inhibition and Immunosuppressive Activity Are Nonadditive," *Journal of Medicinal Chemistry* 38 (21): 4164-4170 (1995), Abstract only.

Hu, "Synthesis And Biological Properties of Novel Cyclosporine Analogs," Diss. Abstr. Int. B 1995, 55(7), 2743 (1994), Abstract only.

Hubler et al., "Synthetic Routes to NEtXaa4-Cyclosporin A Derivatives as Potential Anti-Hiv I Drugs," *Tetrahedron Letters* 41(37):7193-7196 (2000), Abstract only.

Husi et al., "Prediction of Substrate-Specific Pockets in Cyclosporin Synthetase," *FEBS Letters* 414(3):532-536 (1997), Abstract only.

Jegorov et al., "An Unusual Side Chain C-C Cleavage at the MeBmt Amino Acid in Cyclosporin A," *Amino Acids* 10(2):145-151 (1996), Abstract only.

Jegorov et al., "Cyclosporins from *Tolypocladium terricola*," *Phytochemistry* 38(2):403-407 (1995), Abstract only.

Jegorov et al., "Cyclosporins of Symmetry P21—a Series of Clathrates," *Journal of Inclusion Phenomena and Macrocyclic Chemistry* 37(1-4):137-153 (2000), Abstract only.

Jegorov et al., "Synthesis and Crystal Structure Determination of Cyclosporin H," *Collection of Czechoslovak Chemical Communications* 65(8):1317-1329 (2000), Abstract only.

Jiang et al., "Synthesis of Biotinylated Cyclosporin A and Studies on its Interaction With Human Cyclophilin A," *Huaxue Xuebao* 59(10):1745-1750 (2001), Abstract only.

Kanoh et al., Photo-Cross-Linked Small-Molecule Affinity Matrix for Facilitating Forward and Reverse Chemical Genetics *Angewandte Chemie, International Edition* 44(28):4282 (2005) [Erratum], Abstract only.

Kanoh et al., Photo-Cross-Linked Small-Molecule Affinity Matrix for Facilitating Forward and Reverse Chemical Genetics, *Angewandte Chemie, International Edition* 44(23):3559-3562 (2005), Abstract only.

Keller et al., "Pseudoprolines (ψPro) in Drug Design: Direct Insertion of ψPro Systems Into Cyclosporin C," *Chemistry—A European Journal* 6(23):4358-4363 (2000), Abstract only.

Kobel et al., "Directed Biosynthesis of Cyclosporins," *European Journal of Applied Microbiology and Biotechnology* 14(4):237-240 (1982), Abstract only.

Koeck et al., "Novel Backbone Conformation of Cyclosporin A: The Complex With Lithium Chloride," *Journal of the American Chemical Society* 114(7):2676-2686 (1992), Abstract only.

Kratochvil et al., "Crystal Structures of Cyclosporin Derivatives: O-acetyl-(4R)-4-(E-2-butyl)-4,N-Dimethyl-L-Threonyl-Cyclosporin A and O-Acetyl-(4R)-4[E-2-(4- Bromobutyl)]-4,N-Dimethyl-L-Threonyl-Cyclosporin A," *Collection of Czechoslovak Chemical Communications* 64(1):89-98 (1999), Abstract only.

Kuhnt et al., "Microbial Biotransformation Products of Cyclosporin A," *Journal of Antibiotics* 49(8):781-787 (1996), Abstract only.

Lee et al., "Synthesis and Immunosuppressive Activities of Conformationally Restricted Cyclosporin Lactam Analogs," *International Journal of Peptide & Protein Research* 35(5):481-494 (1990), Abstract Only.

Levitsky et al., "Exo-Mechanism Proximity-Accelerated Alkylations: Investigations of Linkers, Electrophiles and Surface Mutations in Engineered Cyclophilin-Cyclosporin Systems," *ChemBioChem* 6(5):890-899 (2005), Abstract only.

Levitsky et al., "Selective Inhibition of Engineered Receptors Via Proximity-Accelerated Alkylation," *Organic Letters* 5(5):693-696 (2003), Abstract only.

Lhoest et al., "Isolation, Identification and Immunosuppressive Activity of a New IMM-125 Metabolite From Human Liver Microsomes. Identification of its Cyclophilin A-IMM-125 Metabolite Complex by Nanospray Tandem Mass Spectrometry," *Journal of Mass Spectrometry* 33 (10):936-942 (1998), Abstract only.

Li et al., "The Development of Highly Efficient Onium-Type Peptide Coupling Reagents Based Upon Rational Molecular Design," *Journal of Peptide Research* 58(2):129-139 (2001), Abstract only.

Li et al., "Total Synthesis of Cyclosporin O Both in Solution and in the Solid Phase Using Novel Thiazolium-, Immonium-, and Pyridinium-Type Coupling Reagents: BEMT, BDMP, and BEP," *Journal of Organic Chemistry* 65(10):2951-2958 (2000), Abstract only.

Liu et al., "Preparation of Cyclosporine A Immunogen," *Sichuan Daxue Xuebao, Ziran Kexueban* 38(3):407-411 (2001), Abstract only.

Liu et al., "Semipreparative Chromatographic Separation Of Cyclosporin G Metabolites Generated by Microsomes from Rabbits Treated With Rifampicin," *Journal of Pharmacological and Toxicological Methods* 35(3):121-129 (1996), Abstract only.

Liu et al., "Structural Characterization of two Novel Oxidative Derivatives of Cyclosporine Generated by a Chemical Method," *Clinical Biochemistry* 31(3):173-180 (1998), Abstract only.

Lu et al., "Modification of Cyclosporin A and Conjugation of Its Derivative to HPMA Copolymers," *Bioconjugate Chemistry* 12(1):129-133 (2001), Abstract only.

Lu et al., "Synthesis of Bioadhesive Lectin-HPMA Copolymer-Cyclosporin Conjugates," *Bioconjugate Chemistry* 11(1):3-7 (2000), Abstract only.

Lynch, "The Search for Cyclophilin Inhibitors: The Design And Synthesis Of Conformationally Constrained Scaffolds," Diss. Abstr. Int., B 1995, 56(2)828 (1995), Abstract only.

Magni et al., "Hydrolytic Conditions for the Formation of Open-Chain Oligopeptides from Cyclosporin A," *Journal of Peptide Research* 49(3):191-194 (1997), Abstract only.

Mahoney et al., "Derivatives of Cyclosporin Compatible With Antibody-Based Assays: I. The Generation of [125I)]-Labeled Cyclosporin," *Clinical Chemistry* (Washington, DC, United States), 31(3):459-462 (1985), Abstract only.

McIntyre et al., "ISA-247," *Drugs of the Future* 29(7):680-686 (2004), Abstract only.

Mikol et al., "The Role of Water Molecules in the Structure-Based Design of (5-Hydroxynorvaline)-2-cyclosporin: Synthesis, Biological Activity, and Crystallographic Analysis with Cyclophilin A," *Journal of Medicinal Chemistry* 38(17):3361-3367 (1995), Abstract only.

Muamba et al. "Peptides: The Wave of the Future," in Lebl eds., *Proceedings of the Second International and the Seventeenth American Peptide Symposium*, San Diego, CA, Jun. 9-14, 2001, 130-131 (2001), Abstract only.

Ohta et al., "Production of Human Metabolites of Cyclosporin A, AM1, AM4N and AM9, by Microbial Conversion," *Journal of Bioscience and Bioengineering* 99(4):390-395 (2005), Abstract only.

Okada et al., "Properties and the Inclusion Behavior of 6-O-α-D-Galactosyl- and 6-O-α-D-Mannosyl- Cyclodextrins," *Chemical & Pharmaceutical Bulletin* 47(11):1564-1568 (1999), Abstract only.

Papageorgiou et al., "Anti HIV-1 Activity of a Hydrophilic Cyclosporine Derivative With Improved Affinity to Cyclophilin," *Bioorganic & Medicinal Chemistry Letters* 6(4):497 (1996) [Erratum], Abstract only.

Papageorgiou et al., "Anti HIV-1 Activity of a Hydrophilic Cyclosporine Derivative With Improved Binding Affinity to Cyclophilin A," *Bioorganic & Medicinal Chemistry Letters* 6(1):23-26 (1996), Abstract only.

Papageorgiou et al., "Calcineurin has a Very Tight-Binding Pocket for the Side Chain of Residue 4 of Cyclosporin," *Bioorganic & Medicinal Chemistry Letters* 4(2):267-272 (1994), Abstract only.

Papageorgiou et al., "Conformational Control of Cyclosporin Through Substitution of the N-5 position. A new class of cyclosporin antagonists," *Bioorganic & Medicinal Chemistry* 5(1):187-192 (1997), Abstract only.

Papageorgiou et al., "Derivatives of Cyclosporin at Position 2 as Probes for Cyclophilin," *Bioorganic & Medicinal Chemistry Letters* 3(12):2559-64 (1993), Abstract only.

Papageorgiou et al., "Improved Binding Affinity for Cyclophilin A by a Cyclosporin Derivative Singly Modified at Its Effector Domain," *Journal of Medicinal Chemistry* 37(22):3674-3676 (1994), Abstract only.

Paprica et al., "Preparation of Novel Cyclosporin A Derivatives," *Bioconjugate Chemistry* 3(1):32-36 (1992), Abstract only.

Patchett et al., "Analogs of Cyclosporin A Modified at the D-Ala8 Position," *Journal of Antibiotics* 45(1):94-102 (1992), Abstract only.

Patiny et al., "Structure-Activity Studies of Novel D-Ser8-Cyclosporin A Derivatives As Potential Anti-HIV Drugs," *Peptides 2002, Proceedings of the European Peptide Symposium, 27th*, Benedetti et al. (eds) 1020-1021 (2002), Abstract only.

Patiny et al., "Synthesis and Characterization of Constrained Cyclosporin A Derivatives Containing a Pseudo-Proline Group," *Tetrahedron* 59(28):5241-5249 (2003), Abstract only.

Pflanz et al., "Induction and Rapid Screening of Monoclonal Antibodies Against Cyclosporin A," *Immunology Letters*, 18(4):241-245 (1988), Abstract only.

Pohl et al., "Crystal Structures of Two Modifications of [3,O-Didehydro-MeBmtl,Va12]Cyclosporin and Comparison of Three Different X-Ray Data Sets," *Helvetica Chimica Acta* 78(2):355-366 (1995), Abstract only.

Radeke et al., "Additive and Synergistic Effects of Cyclosporine Metabolites on Glomerular Mesangial Cells," *Kidney International* 39(6): 1255-1266 (1991), Abstract only.

Raman Dissertation, 338 pp. Avail.: UMI, Order No. DA9809876 From: Diss. Abstr. Int., B 1998, 59(3), 1117 (1997), Abstract only.

Raman et al., "Methods to Circumvent a Difficult Coupling in the Solid-Phase Synthesis of Cyclosporine Analogs," *Journal of Organic Chemistry* 63(17):5734-5735 (1998), Abstract only.

Rich et al., "Synthesis and Antimitogenic Activities of Four Analogs of Cyclosporin A Modififed in the 1-Position," *Journal of Medicinal Chemistry* 29(6):978-984 (1986), Abstract only.

Rich et al., "Synthesis, Biological Activity, and Conformational Analysis of (2S,3R,4S)-MeBmt-Cyclosporin, A Novel 1-Position Epimer of Cyclosporin A," *Journal of Medicinal Chemistry* 32(8):1982-1987 (1989), Abstract only.

Rihova et al., "Cytotoxic and Cytostatic Effects of Anti-Thy 1.2 Targeted Doxorubicin and Cyclosporin A," *Journal of Controlled Release* 40(3):303-319 (1996), Abstract onl y.

Roedl et al., "Lipoprotein-Induced Modulation of Cyclosporine A-Mediated Immunosuppression," *European Journal of Clinical Investigation* 20(3):248-252 (1990), Abstract only.

Romanova et al., "Synthesis of Cyclosporin A Fragment 8-11," *Ukrainskii Khimicheskii Zhurnal (Russian Edition)* 55(5):527-530(1989), Abstract only.

Rothbard et al., "Conjugation of Arginine Oligomers to Cyclosporin A Facilitates Topical Delivery and Inhibition of Inflammation," *Nature Medicine* New York 6(11):1253-1257 (2000), Abstract only.

Rothe et al., in Brunfeldt, ed., *Pept., Proc. Eur. Pept. Symp.*, 16th Meeting Date 1980, Scriptor: Copenhagen, Den pp. 258-263 (1981), Abstract only.

Rozycki et al., "New Cyclosporin A Analog: Synthesis and Immunosuppressive Activity," *Molecular Immunology* 29(9): 1043-1047 (1992), Abstract only.

Ruegger et al., "Cyclosporin A, A Peptide Metabolite From *Trichoderma polysporum* (Link ex Pers.) Rifai, With Immunosuppressive Activity," *Helvetica Chimica Acta* 59(4):1075-1092 (1976), Abstract only.

Sakamoto et al., "FR901459, a Novel Inununosuppressant Isolated From *Stachybotrys chartarum* No. 19392. Taxonomy of the Producing Organism, Fermentation, Isolation, Physico-Chemical Properties and Biological Activities," *Journal of Antibiotics* 46(12):1788-1798 (1993), Abstract only.

Shevchenko et al., "Synthesis of Tritiated Cyclosporin A and FK-506 by Metal-Catalyzed Hydrogen Isotope Exchange," *Journal of Labelled Compounds & Radiopharmaceuticals* 47(7):407-414 (2004), Abstract only.

Shevchenko et al., Synthesis of Tritium-Labeled Immunodepressants Containing Double Bonds by Isotope Exchange with Tritium Water, *Radiochemistry* (Moscow) (Translation of Radiokhimiya) 41(1):85-88 (1999), Abstract only.

Smulik et al., "Synthesis of Cyclosporin A-Derived Affinity Reagents by Olefin Metathesis," *Organic Letters* 4(2):2051-2054 (2002), Abstract only.

Stabler et al., "Chemiluminescence Immunoassay of Cyclosporine in Whole Blood," *Clinical Chemistry* (Washington, DC, United States), 36(6):906-908 (1990), Abstract only.

Sun et al., "Synthesis, Conformation, and Immunosuppressive Activity of Cyclosporines That Contain ϵ-Oxygen (4R)-4-[(E)-butenyl]-4,N-Dimethyl-L-Threonine Analogs in the 1-Position," *Journal of Medicinal Chemistry* 33(5):1443-1452 (1990), Abstract only.

Sun, "Synthesis of Cyclosporin Analogs Modified in the 1-Position," Diss. Abstr. Int. B 1990, 50(12, Pt. 1), 5637 (1989), Abstract only.

Tamolang et al., "A Rifampicin-Induced Hepatic Microsomal Enzyme System for the Generation of Cyclosporine Metabolites," *Pharmacological Research* 32(3):141-148 (1995), Abstract only.

Thern et al., "Peptides: The Wave of the Future," in Lebl, eds., *Proceedings of the Second International and the Seventeenth American Peptide Symposium*, San Diego, CA, Jun. 9-14, 2001, 244-245 (2001), Abstract only.

Thern et al., "Triphosgene as Highly Efficient Reagent for the Solid-Phase Coupling of N-Alkylated Amino Acids-Total Synthesis of Cyclosporin O," *Tetrahedron Letters* 43(28):5013-5016 (2002), Abstract only.

Traber et al., "[Melle4]Cyclosporin, a Novel Natural Cyclosporin With Anti-HIV Activity: Structural Elucidation, Biosynthesis and Biological Properties," *Antiviral Chemistry & Chemotherapy* 5(5):331-339 (1994), Abstract only.

Traber et al., "New Cyclopeptides From *Trichoderma polysporum* (Link ex Pers.) Rifai: Cyclosporins B, D and E," *Helvetica Chimica Acta* 60(5):1568-1578 (1977), Abstract only.

Traber et al., "Novel Cyclosporins from *Tolypocladium inflatum.* Cyclosporins K-Z," *Helvetica Chimica Acta* 70(1):13-36 (1987), Abstract only.

Traber et al., "Occurrence of Cyclosporins and Cyclosporin-Like Peptolides in Fungi," *Journal of Industrial Microbiology & Biotechnology* 17(5/6):397-401 (1996), Abstract only.

Traber et al., "The Structure of Cyclosporin C." *Helvetica Chimica Acta* 60(4):1247-1255 (1977), Abstract only.

Tung et al., "Synthesis and Biological Properties of a High Specific Activity Radioiodinated, Photolabile Cyclosporin," *UCLA Symposia on Molecular and Cellular Biology, New Series*, 86(Synth. Pept.), pp. 321-335 (1989), Abstract only.

Tuominen et al., "Separation of Cyclosporins by High-Performance Liquid Chromatography and Mass Spectrometric Study of Cyclosporin Metabolites," *Rapid Communications in Mass Spectrometry* 12(16):1085-1091 (1998), Abstract only.

Vedejs et al., "Solution-Phase Synthesis of a Hindered N-Methylated Tetrapeptide Using Bts-Protected Amino Acid Chlorides: Efficient Coupling and Methylation Steps Allow Purification by Extraction," *Journal of Organic Chemistry* 65(8):2309-2318 (2000), Abstract only.

Wei et al., "Synthesis and Neurotrophic Activity of Nonimmunosuppressant Cyclosporin A Derivatives," *Bioorganic & Medicinal Chemistry Letters* 14(17):4549-4551 (2004), Abstract only.

Wenger et al., "Cyclosporine: Chemistry, Structure-Activity Relationships and Mode of Action," *Progress in Clinical Biochemistry and Medicine* 3:157-191(1986), Abstract only.

Wenger et al., "Structure of Cyclosporine and its Metabolites: Total Synthesis of Cyclosporine Metabolites Formed by Oxidation at Positions 4 and 9 of Cyclosporine. Preparation of Leucine-4-Cyclosporine, ($\gamma$-hydroxy)-N-Methylleucine-9-Cyclosporine and Leucine-4-($\gamma$-hydroxy)-N-Methylleucine-9-Cyclosporine," *Chimia* 46(7-8):314-322 C (1992), Abstract only.

Wenger, "Synthesis of Ciclosporin and Analogs: Structural and Conformational Requirements for Immunosuppressive Activity," *Progress in Allergy* 38 (Ciclosporin):46-64 (1986), Abstract only.

Wenger, "Synthesis of Cyclosporin and Analogs: Structure, Activity, Relationships of New Cyclosporin Derivatives," *Transplantation Proceedings* 15(4, Suppl. 1-2)2230-2241 (1983), Abstract only.

Wu et al., "Preparation of Cyclosporin A Immunogen,"*Journal of Chinese Pharmaceutical Sciences* 11(3):78-82 (2002), Abstract only.

Yamada et al., "Single-Step N-Methylation of Hindered Peptides: Total Synthesis of Cyclosporin O," *Peptide Science* 41:591-594 Volume Date 2004, (2005), Abstract only.

Paeshuyse et al., "Potent and Selective Inhibition of Hepatitis C Virus Replication by the Non-Immunosuppressive Cyclosporin Analogue DEB10-025," *Antiviral Research* 65(3):A41 (2005).

Nakagawa et al., "Specific Inhibition of Hepatitis C Virus Replication by Cyclosporin A," *Biochem. Biophys. Res. Commun*. 313:42-47 (2004).

Inoue et al., "Combined Interferon $\alpha$2b and Cyclosporin A in the Treatment of Chronic Hepatitis C: Controlled Trial," *J. Gastroenterol*. 38:567-572 (2003).

Bandera et al., "Immunomodulants in HIV Infection," *Expert Opin. Ther. Patents* 15(9):1115-1131 (2005).

Bartz et al., "Inhibition of Human Immunodeficiency Virus Replication by Non-Immunosuppressive Analogs of Cyclosporin A," *Proc. Natl. Acad. Sci. USA* 92:5381-5385 (1995).

Prelog et al., "Treatment of Psoriatic Arthritis with Cyclosporin A," *Acta Dermatovenerologica, Alpina, Pannonica et Adriatica*, 9(3):1-5 (2000).

Rosenwirth et al., "Debio-025, A Novel Non-Immunosuppressive Cyclosporine Analog with Potent Anti-Human Immunodeficiency Virus Type 1 Activity: Pharmacological Properties and Mode of Action," *Antiviral Research*, 64(3):42-43 (2005).

DEB 025, ADIS Database, pp. 1-2 (Oct. 12, 2005).

\* cited by examiner ue OF CYCLOSPORIN ALKYNE/ALKENE ANALOGUES FOR PREVENTING OR TREATING VIRAL-INDUCED DISORDERS

FIELD OF THE INVENTION

The present invention discloses novel cyclosporin alkyne/alkene analogues and their utilities as pharmaceutical agents for prevention and treatment of viral-induced diseases. Methods for preparation of such analogues are also disclosed.

BACKGROUND OF THE INVENTION

Cyclosporin A (CsA), a neutral cyclic undecapeptide isolated from the fungus *Tolypocladium inflatum* and currently marketed as NEORAL® and SANDIMMUNE® (Novartis, Basel, Switzerland), has been widely used for the prevention of organ transplant rejection. The molecular basis for the immunosuppressant activity of cyclosporin A and cyclosporin analogues begins with the passive diffusion of the cyclosporin (Cs) molecule into the cell, followed by binding to its intracellular receptor, cyclophilin A (CypA). CypA belongs to a family of proteins that catalyze cis-trans peptidyl-prolyl isomerization, i.e., PPIase, a rate-limiting step in protein folding. CsA and other cyclosporin analogues bind to the active site of CypA. However, immunosuppression is not believed to be due to the inhibition of CypA PPIase activity. The target of the CsA-CypA complex is a $Ca^{2+}$-calmodulin-dependent serine-threonine-specific protein phosphatase, calcineurin. In T-cells responding to antigen presentation, an increase in intracellular $Ca^{2+}$ activates calcineurin, which subsequently dephosphorylates the transcription factor called the nuclear factor of activated T-cells ("NFAT"). Dephosphorylated NFAT undergoes a molecular change, e.g., homodimerization that allows it to cross into the nucleus, and promotes the expression of T-cell activation genes. CsA and other immunosuppressive cyclosporin derivatives inhibit calcineurin which results in the inhibition of expression of cytokine genes, e.g., interleukin-2 (IL-2) that promotes T-cell activation and proliferation, i.e., immunosuppressive activity.

Human Immunodeficiency Viruses and Cyclosporin A or Non-Immunosuppressive Cyclosporins Human immunodeficiency viruses ("HIVs") are lentiviruses, a family of mammalian retroviruses evolved to establish chronic persistent infection with gradual onset of clinical symptoms. There are two major families of HIV. Most of the epidemic involves HIV-1; HIV-2 is a close relative whose distribution is concentrated in western Africa.

Human cyclophilins A and B have been identified as cellular proteins which bind specifically to HIV-1 Gag polyprotein, $p555^{gag}$. Gag proteins play a major role in several steps of the virus life cycle, including the assembly and release of virions (Willis et al., "Form, Function, and Use of Retroviral Gag Proteins," *AIDS* 5:639-654 (1991)). A cleavage product of the Gag polyprotein, the capsid protein, has been shown to bind specifically to cyclophilin A. Cyclophilin A is functionally associated with the HIV-1 virions through interaction with the Gag polyprotein. This interaction between cyclophilin A and Gag proteins is inhibited by the immunosuppressive drug, cyclosporin A (Thali et al., "Functional Association of Cyclophilin A With HIV-1 Virions," *Nature* 372:363-365 (1994)).

Cyclosporin A has demonstrated in vitro antiviral activity against HIV-1 (Karpas et al., "Inhibition of Human Immunodeficiency Virus and Growth of Infected T-cells by the Immunosuppressive Drugs Cyclosporin A and FK 506," *Proc. Natl. Acad. Sci. USA* 89:8351-8355 (1992)); however, initial in vivo studies in which cyclosporin A was administered as a monotherapy in HIV-infected patients at advanced stages of disease did not show a beneficial effect from the treatment (Levy et al., "Long-Term Follow-Up of HIV Positive Asymptomatic Patients Having Received Cyclosporin A," *Adv. Ex. Med. Biol.* 374:229-234 (1995)). U.S. Pat. No. 4,814,323 to Andrieu et al. reported that administration of cyclosporins may be used for the prevention of AIDS in patients infected with the virus before the appearance of the AIDS symptoms, that is patients with no symptoms or patients with AIDS related complex.

Highly active antiretroviral therapy ("HAART") has dramatically decreased the HIV-related morbidity and mortality rates among HIV-infected patients and the transmission of HIV from mother to child by efficiently suppressing viral replication (Palella et al., "Declining Morbidity and Mortality Among Patients With Advanced Human Immunodeficiency Virus Infection," *N. Eng. J. Med.* 338:853-860 (1998)). Limitations of HAART have become better understood. Thus, the virus can be suppressed to undetectable levels but not eradicated. In addition, there is an ever-growing list of side effects, the eventual development of resistance, and the cost and complexity of HAART regimens that must be contended with.

HAART covers a broad range of antiretroviral agents that include nucleoside reverse transcriptase inhibitors ("NRTI"), nonnucleoside reverse transcriptase inhibitors ("NNRTI"), HIV protease inhibitors, and fusion inhibitors. Specific examples of antiviral agents from each of these families include: Zidovudine, Didanosine, Stavudine, and Lamivudine from the NRTI antiviral class; Nevirapine, Efavirenz, and Delavirdine from the NNRTI antiviral class; Saquinovir, Indinavir, and Ritonavir from the HIV protease inhibitor class; and Enfuvirtide from the fusion inhibitor antiviral class.

From an immunological standpoint, the introduction of HAART allows for only a partial immune reconstitution. Indeed, ex vivo measures of immune function do not generally normalize and, most importantly, HIV-specific T cell responses remain almost invariably impaired. Though several variables have been identified that correlate with the degree of immune reconstitution during HAART, the actual underlying mechanism(s) responsible for such an incomplete immune reconstitution are still poorly understood and likely reflect the severe HIV-driven perturbations in T cell dynamics and homeostasis and the interaction between host and viral factors (Douek, "Disrupting T-Cell Homeostasis: How HIV-1 Infection Causes Disease," *AIDS Rev.* 5:172-177 (2003)).

A strategy aimed at the broadest immune reconstitution, possibly overcoming the limitations of HAART, consists in the adjuvant use of immunomodulants. By combining cyclosporin A with HAART, the goal is to contain the immune activation, either virus-specific or owing to non-specific "bystander" activation. Results from pilot studies in HIV-infected patients has shown that the rapid shutdown of T-cell activation induced by cyclosporin A has produced a more rapid and stable increase in CD4+ T-cells and a significant long-term increase in IFN-γ secreting CD4+ and CD4+ CCR7-T-cells, establishing a more favorable immunological set-point (Bandera et al., "Immunomodulants in HIV Infection," *Expert Opin. Ther. Patents* 15(9):1115-1131 (2005)). Determination of the long-term efficacy must be assessed in order to understand if this approach truly has value.

SDZ NIM 811 is a cyclosporin analogue that is completely devoid of immunosuppressive activity but exhibits potent and selective anti-HIV-1 activity (Mlynar et al., "The Non-Immunosuppressive Cyclosporin A Analogue SDZ NIM 811 Inhibits Cyclophilin A Incorporation Into Virions and Virus Replication in Human Immunodeficiency Virus Type-1-Infected Primary and Growth-Arrested Cells," *J. General Virology* 78:825-835 (1997)). SDZ NIM 811 does not prevent the activation of CD4+ T-cell activation as cyclosporin A does. In a manner similar to cyclosporin A, it is proposed that SDZ NIM 811 interferes with the HIV-1 Gag-cyclophilin A interaction to effect its antiviral activity.

SDZ NIM 811 does not inhibit calcineurin and possesses none of the immunosuppressive activity of cyclosporin A. The potent inhibition of calcineurin by cyclosporin, in addition to being responsible for the potent immunosuppressive activity of cyclosporin A, is also believed to be the cause of the toxicity and the narrow therapeutic index of this drug. Separation of immunosuppressive and antiviral activity could lead to novel antiviral cyclosporins with fewer side effects and improved therapeutic index. Elucidation of structure activity relationships for cyclosporins permits the design of non-immunosuppressive cyclosporin derivatives that retain potent (cyclophilin A) PPIase activity to achieve this goal (Bartz et al., "Inhibition of Human Immunodeficiency Virus Replication by Non-Immunosuppressive Analogs of Cyclosporin A," *Proc. Natl. Acad. Sci. USA* 92:5381-5385 (1995)). European Patent No. 484 281, U.S. Pat. No. 5,767,069, U.S. Pat. No. 5,948,884, and French Patent Nos. 2,757,520, 2,757,521, and 2,757,522 disclose non-immunosuppressive cyclosporins with antiviral activity.

Hepatitis C Virus and Cyclosporin A

Recently, cyclosporin A, the most widely prescribed immunosuppressive drug, was reported to be clinically effective against hepatitis C viral (HCV) infection (Nakagawa et al., "Specific Inhibition of Hepatitis C Virus Replication by Cyclosporin A," *Biochem. Biophys. Res. Commun.* 313:42-47 (2004)). The authors of the Nakagawa et al. paper state that certain chaperone activities, such as those of cyclophilins, may be crucial for the processing and maturation of the viral proteins and for viral replication.

A subsequent controlled clinical trial showed that a combination of cyclosporin A with interferon α2b is more effective than interferon monotherapy, especially in patients with high viral loads (Inoue et al., "Combined Interferon α2b and Cyclosporin A in the Treatment of Chronic Hepatitis C: Controlled Trial," *J. Gastroenterol.* 38:567-572 (2003)).

PCT International Patent Publication No. WO 2006/005610 recently described the use of a combination of cyclosporin A and pegylated interferon for treating hepatitis C viral infection. In addition, PCT International Patent Publication No. WO 2005/021028 relates to the use of non-immunosuppressive cyclosporins for treatment of HCV disorders. Also, Paeshuyse et al., "Potent and Selective Inhibition of Hepatitis C Virus Replication by the Non-Immunosuppressive Cyclosporin Analogue DEBIO-025," *Antiviral Research* 65(3):A41 (2005) recently published results for a non-immunosuppressive cyclosporin analogue, DEBIO-025, that exhibited potent and selective inhibition of hepatitis C virus replication. Notably, the cyclosporin derivative DEBIO-025 is also effective for the treatment of HIV-1 (Rosenwirth et al., "Debio-025, A Novel Non-Immunosuppressive Cyclosporine Analog with Potent Anti-Human Immunodeficiency Virus Type 1 Activity: Pharmacological Properties and Mode of Action," *Antiviral Research* 65(3): A42-A43 (2005)). Debio-025 does possess potent binding affinity for cyclophilin A.

There is still a large need for novel cyclosporin analogues that have therapeutic utility in the treatment of viral-induced diseases.

The present invention is directed to achieving these objectives.

SUMMARY OF THE INVENTION

The present invention relates to a method of preventing or treating a mammal with a viral-induced disorder. The method involves administering to the mammal a therapeutically effective amount of a compound having the following formula:

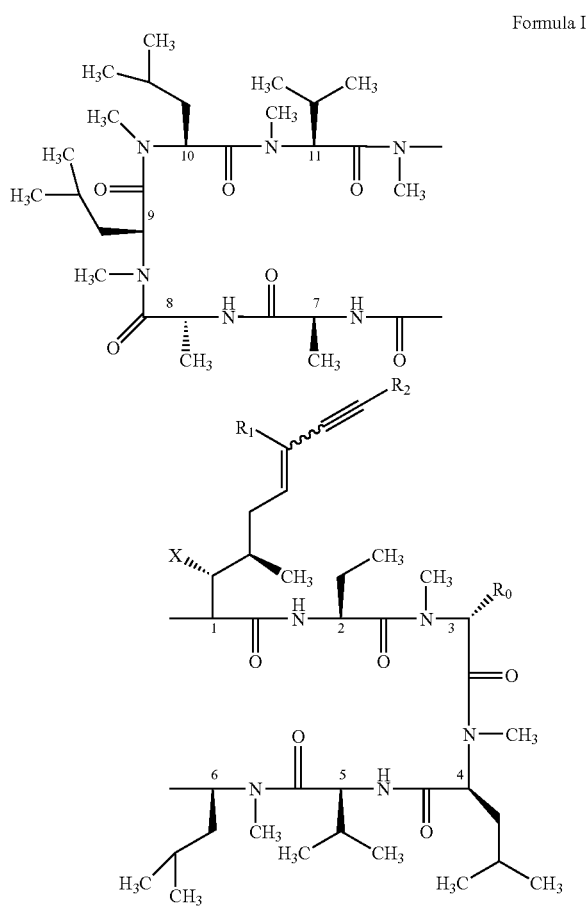

Formula I where:

X is OH or OAc;

$R_0$ is H, $CH_2OH$, or $CH_2OR_3$;

$R_1$ is hydrogen, deuterium, or methyl;

$R_2$ is selected from the group consisting of:
  hydrogen;
  halogen;
  $C_1$-$C_6$ saturated or unsaturated, straight or branched carbon chain;
  $C_1$-$C_6$ saturated or unsaturated, straight or branched carbon chain containing a substitution or substitutions selected from the group consisting of deuterium, halogen, nitrogen, sulfur, and silicon;
  $C_1$-$C_6$ saturated or unsaturated, straight or branched carbon chain containing a function group or function groups selected from the group consisting of alcohol, ether, aldehyde, ketone, carboxylic acid, ester, and amide;

$C_1$-$C_6$ saturated or unsaturated, straight or branched carbon chain containing a function group of oxime or hydrazone;

$C_1$-$C_6$ saturated or unsaturated, straight or branched carbon chain containing an aryl or a heteroaryl group;

$C_3$-$C_6$ substituted and unsubstituted cycloalkyl;

substituted and unsubstituted aryl; and substituted and unsubstituted heteroaryl; and $R_3$ is selected from the group consisting of:
alkanoyl,
alkenoyl,
alkynoyl,
aryloyl,
arylalkanoyl,
alkylaminocarbonyl,
arylaminocarbonyl,
arylalkylaminocarbonyl,
alkyloxycarbonyl,
aryloxycarbonyl, and
arylalkyloxycarbonyl, where the compound is a cis geometric isomer, a trans geometric isomer, or a mixture of the cis and the trans geometric isomers or a pharmaceutically acceptable salt thereof, under conditions effective to prevent or treat the viral-induced disorder.

The present invention discloses chemically modified cyclosporin analogues containing a carbon-carbon triple bond on the side chain of the position one amino acid and optionally a substitution on the position three amino acid of cyclosporin A. In particular, the present invention discloses novel cyclosporin analogues containing a conjugated system of a carbon-carbon triple bond and a carbon-carbon double bond on the side chain of the position one amino acid of cyclosporin A.

The present invention discloses novel cyclosporin analogues which are effective as antiviral agents. The cyclosporin derivatives of the present invention used to treat viral infections may possess potent immunosuppressive activity (via inhibition of calcineurin) or may be completely devoid of immunosuppressive activity (do not inhibit calcineurin). However, the mechanism that the immunosuppressive and non-immunosuppressive cyclosporin compounds share is their activity at cyclophilin A.

DETAILED DESCRIPTION OF THE INVENTION

Figure 1:
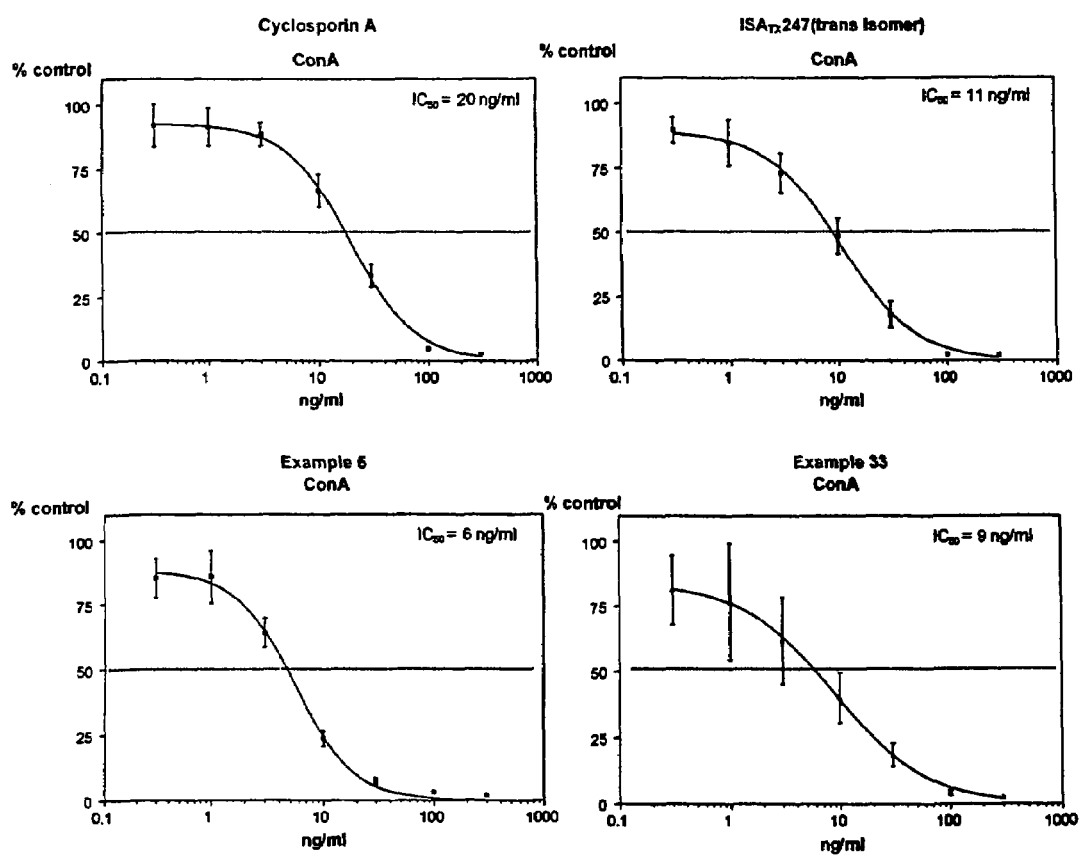
FIG. 1 depicts the results from a concanavalin A (ConA)-stimulated murine splenocyte assay, where the novel cyclosporin analogue compounds of the present invention (disclosed in Examples 5 and 33) are shown to possess enhanced or similar potency in immunosuppression, compared to cyclosporin A and $ISA_{TX}247$.

The present invention relates to a method of preventing or treating a mammal with a viral-induced disorder. The method involves administering to the mammal a therapeutically effective amount of a compound having the following formula:

Formula I where:
X is OH or OAc;
$R_0$ is H, $CH_2OH$, or $CH_2OR_3$;
$R_1$ is hydrogen, deuterium, or methyl;
$R_2$ is selected from the group consisting of:
hydrogen;
halogen;
$C_1$-$C_6$ saturated or unsaturated, straight or branched carbon chain;
$C_1$-$C_6$ saturated or unsaturated, straight or branched carbon chain containing a substitution or substitutions selected from the group consisting of deuterium, halogen, nitrogen, sulfur, and silicon;
$C_1$-$C_6$ saturated or unsaturated, straight or branched carbon chain containing a function group or function groups selected from the group consisting of alcohol, ether, aldehyde, ketone, carboxylic acid, ester, and amide;
$C_1$-$C_6$ saturated or unsaturated, straight or branched carbon chain containing a function group of oxime or hydrazone;
$C_1$-$C_6$ saturated or unsaturated, straight or branched carbon chain containing an aryl or a heteroaryl group;
$C_3$-$C_6$ substituted and unsubstituted cycloalkyl;
substituted and unsubstituted aryl; and
substituted and unsubstituted heteroaryl; and $R_3$ is selected from the group consisting of:
 alkanoyl,
 alkenoyl,
 alkynoyl,
 aryloyl,
 arylalkanoyl,
 alkylaminocarbonyl,
 arylaminocarbonyl,
 arylalkylaminocarbonyl,
 alkyloxycarbonyl,
 aryloxycarbonyl, and
 arylalkyloxycarbonyl, where the compound is a cis geometric isomer, a trans geometric isomer, or a mixture of the cis and the trans geometric isomers or a pharmaceutically acceptable salt thereof, under conditions effective to prevent or treat the viral-induced disorder.

The wavy bond in the structure of Formula I indicates the carbon-carbon double bond is the cis geometric isomer, the trans geometric isomer, or a mixture of both the cis and the trans geometric isomers.

One embodiment of the present invention is the above compound of Formula I, where: X is OH or OAc; $R_0$ is H, $CH_2OH$, or $CH_2OAc$; $R_1$ is H or D; and $R_2$ is H.

Another embodiment of the present invention is the above compound of Formula I, where: X is OH or OAc; $R_0$ is H, $CH_2OH$, or $CH_2OAc$; $R_1$ is H or D; and $R_2$ is $CH_3$, $CD_3$, $CH_2CH_3$, or $CH_2CH_2CH_3$.

Another embodiment of the present invention is the above compound of Formula I, where: X is OH or OAc; $R_0$ is H, $CH_2OH$, or $CH_2OAc$; $R_1$ is H or D; and $R_2$ is $-CH=CH_2$, $-CH=CHCH_3$, $-C\equiv CH$, or $-C\equiv C-CH_3$.

Another embodiment of the present invention is the above compound of Formula I, where: X is OH or OAc; $R_0$ is H, $CH_2OH$, or $CH_2OAc$; $R_1$ is H or D; and $R_2$ is F, Cl, Br, or I.

Another embodiment of the present invention is the above compound of Formula I, where: X is OH or OAc; $R_0$ is H, $CH_2OH$, or $CH_2OAc$; $R_1$ is H or D; and $R_2$ is cyclopropyl.

Another embodiment of the present invention is the above compound of Formula I, where: X is OH or OAc; $R_0$ is H, $CH_2OH$, or $CH_2OAc$; $R_1$ is H or D; and $R_2$ is $CH_2OH$, $CH(OH)CH_3$, $CH_2OCH_3$, $CH_2OCH_2CH_3$, CHO, and $C(=O)CH_3$.

Another embodiment of the present invention is the above compound of Formula I, where: X is OH or OAc; $R_0$ is H, $CH_2OH$, or $CH_2OAc$; $R_1$ is H or D; and $R_2$ is $CH=N-OCH_3$, $CH=N-OCH_2CH_3$, $CH=N-NHCH_3$, or $CH=N-N(CH_3)_2$.

Another embodiment of the present invention is the above compound of Formula I, where: X is OH or OAc; $R_0$ is H; $R_1$ is H; and $R_2$ is H, $CH_3$, $Si(CH_3)_3$.

Other embodiments of the present invention include novel cyclosporine analogue compounds represented by Formula Ia, as shown below:

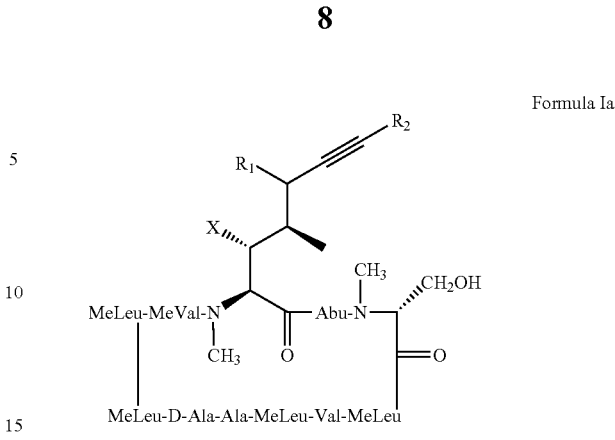

Formula Ia where:
X=OH or OAc;
$R_0$=H;
$R_1$=H or D; and
$R_2$=H, $CH_3$, $CD_3$, n-propyl, n-butyl, $-CH_2CH_2CH_2Cl$, $Si(CH_3)_3$, Ph, p-$ClC_6H_4-$, 2-pyridinyl, 3-thiophenyl, cyclopropyl, cyclohexyl, $-CH_2OH$, $-CH(OH)CH_3$, $-CH_2CH_2OH$, $-CH(OH)CH_2CH_3$, $-CHO$, $-C(=O)CH_3$, $-CH=CH_2$, $-CH=CHCH_3$, $-C(CH_3)=CH_2$, $-CH=CHI$, Br, I, $-CH_2OCH_3$, $-CH_2OPh$, $-CH_2OCH_2CH=CH_2$, $-CH_2OCH_2C\equiv CH$, $-CH_2SCH_2CH_3$, $-CH_2OCH_2CO_2Bu^t$, $-CH_2OCH_2CO_2H$, $-CO_2H$, $-CH_2CH_2CO_2H$, $-CH=N-OCH_3$, or $-CH=N-N(CH_3)_2$;

or where:
X=OH or OAc;
$R_0$=$CH_2OH$ or $CH_2OAc$;
$R_1$=H or D; and
$R_2$=H, $CH_3$, $CD_3$, n-propyl, $Si(CH_3)_3$, Br, $-CH=CH_2$, 3-thiophenyl, $-CH_2OH$, $-CH(OH)CH_3$, $-CH_2OCH_3$, $-CH_2SCH_2CH_3$, $-CH_2OPh$, $-CH_2OCH_2C\equiv CH$, cyclopropyl, or cyclohexyl.

Other embodiments of the present invention include novel cyclosporine analogue compounds represented by Formula Ib, as shown below:

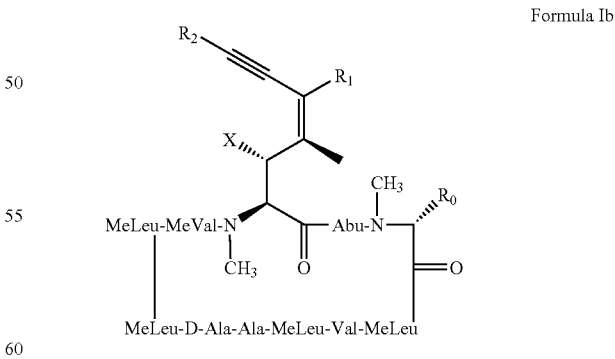

Formula Ib where:
X=OH or OAc;
$R_0$=H;
$R_1$=H or D; and
$R_2$=H, $CH_3$, $Si(CH_3)_3$.

In particular, the present invention relates to novel cyclosporin analogues containing a carbon-carbon triple bond on the side chain of the position one amino acid and optionally a substitution on the position three amino acid of cyclosporin A. More particularly, the present invention relates to novel cyclosporin analogues containing a conjugated system, in which a function group of a carbon-carbon triple bond conjugating with a carbon-carbon double bond is incorporated.

A carbon-carbon triple bond exists in many natural products (Gung et al., "Total synthesis of(S)-(–)-(E)-15,16-Dihydrominquartynoic Acid: A Highly Potent Anticancer Agent," *J. Org. Chem.*, 69:3488-3492 (2004); Ito et al., "Cytotoxic Polyacetylenes from the Twigs of *Ochanostachys amentacea*," *J. Nat. Prod.*, 64:246-248 (2001), which are hereby incorporated by reference in their entirety). It is well known to use alkynes as pharmaceutical agents. However, only one cyclosporin alkyne, in which a carbon-carbon triple bond replaces the carbon-carbon double bond on the side chain of the position one amino acid of cyclosporin A, is known in the literature. Unfortunately, this modification significantly reduces the immunosuppressive activity of cyclosporin A, where this known cyclosporin alkyne shows only 10% relative immunosuppressive activity compared to cyclosporin A (Rich et al., "Synthesis, Conformation, and Immunosuppressive Activities of Three Analogues of Cyclosporin A Modified in the 1-Position," *J. Med. Chem.*, 33:999-1009 (1990), which is hereby incorporated by reference in its entirety). In contrast, the novel cyclosporin alkyne analogues of the present invention, which contains a conjugated system of a carbon-carbon triple bond and a carbon-carbon double bond, possess enhanced immunosuppressive activity over cyclosporin A.

The present invention also discloses methods for preparing the compounds represented by Formula I.

The starting material for the preparation of compounds of the present invention is cyclosporin A. The structure of cyclosporin A, a cycloundecapeptide, and the position numbering for each amino acid in the ring is shown below:

Cyclosporin A can also be represented by Formula IIa, as shown below:

Formula IIa

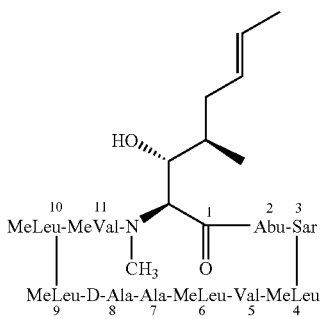

The novel cyclosporin analogues of the present invention are derived from cyclosporin A or cyclosporin diol (Formula IIb), a key intermediate prepared by modification at the position three amino acid of cyclosporin A. As shown in Scheme 1, the cyclosporin diol intermediate can be prepared by deprotonation of cyclosporin A with lithium diisopropylamide (LDA) followed by treatment with formaldehyde (Seebach et al, "Modification of Cyclosporin A: Generation of an Enolate at the Sarcosine Residue and Reaction with Electrophiles," *Helv. Chim. Acta*, 76:1564-1590 (1993), which is hereby incorporated by reference in its entirety).

Scheme 1

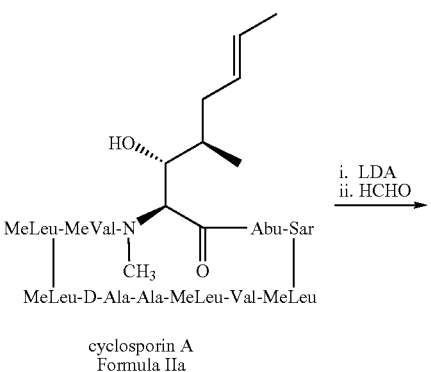

cyclosporin A
Formula IIa

Cyclosporin A (CsA)

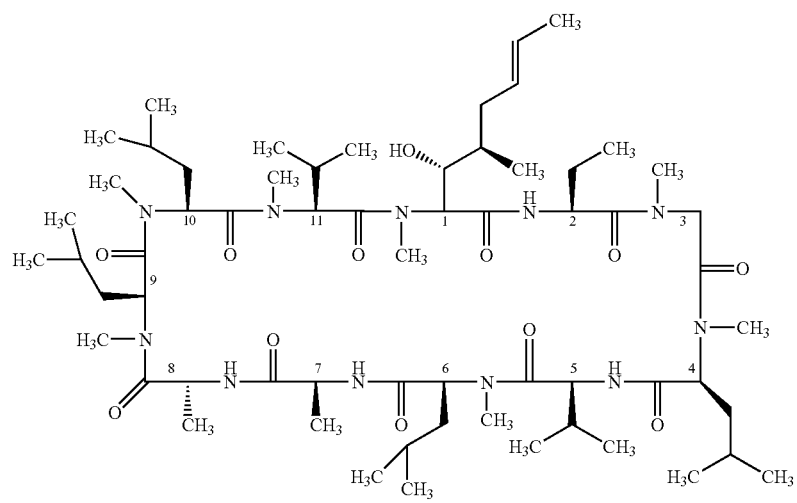

-continued

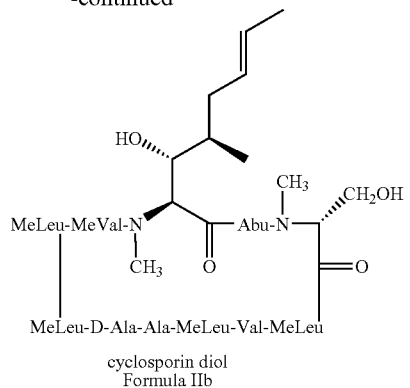

cyclosporin diol
Formula IIb

According to one embodiment of the present invention, novel cyclosporin alkyne analogues can be prepared by employing palladium-mediated couplings (such as Sonogashira and Negishi coupling) as a key step, which is outlined in Scheme 2. Acetylation of cyclosporin A (Formula IIa) or cyclosporin diol intermediate of Formula IIb with acetic anhydride, followed by oxidative cleavage of the double bond with ozone, generates the cyclosporin aldehyde of Formula III smoothly. Treatment of the cyclosporin aldehyde with iodoform-$CrCl_2$ complex (Takai et al, "Simple and Selective Method for RCHO→(E)-RCH═CHX Conversion by Means of a $CHX_3$—$CrCl_2$ System," *J. Am. Chem. Soc.*, 108:7408-7410 (1986), which is hereby incorporated by reference in its entirety) affords cyclosporin vinyl iodides of Formula IVa in good to excellent yield (50-80%) in exclusively the trans-configuration. Palladium-catalyzed coupling (such as Sonogashira coupling and Negishi coupling) of the cyclosporin vinyl iodide of Formula IVa with various alkynes or alkynylzinc reagents provides novel cyclosporin alkynes of Formula Ia in the trans-configuration in high yield. The acetyl protecting group in the cyclosporin alkyne of Formula Ia can be removed by treatment with potassium carbonate in methanol (see Scheme 2).

Scheme 2

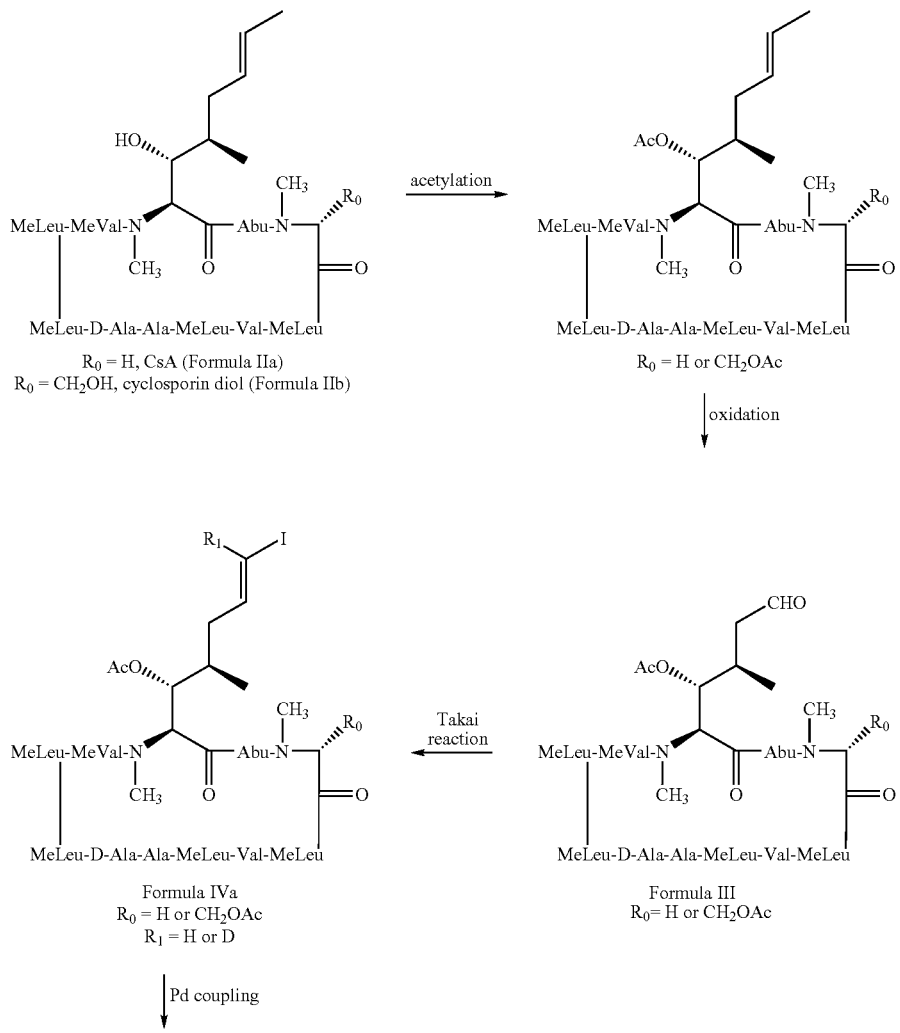

-continued

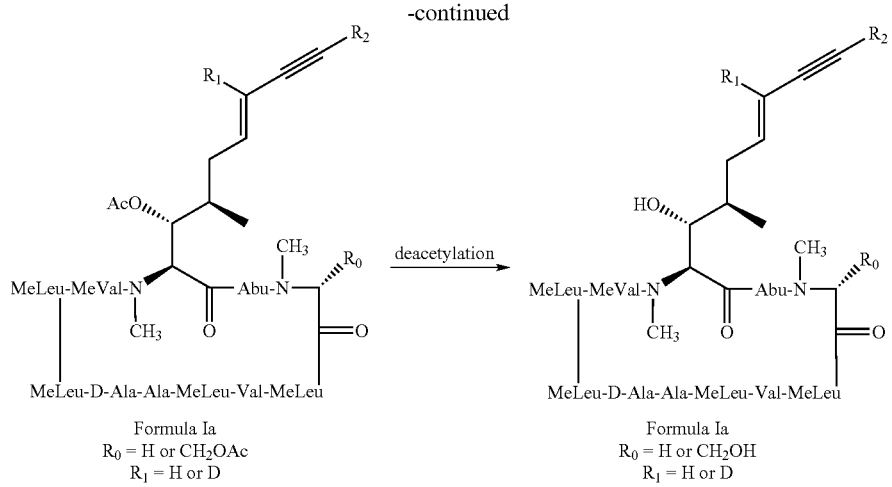

Formula Ia
R₀ = H or CH₂OAc
R₁ = H or D

Formula Ia
R₀ = H or CH₂OH
R₁ = H or D

Utilizing the same strategy, the cis-isomer of cyclosporin alkyne analogues (Formula Ib) can be prepared using the cis-isomer of cyclosporin vinyl iodide (Formula IVb), as shown in Scheme 3. By application of phosphorous ylide chemistry (Wittig reaction), the cyclosporin aldehyde of Formula III can be converted to the cyclosporin vinyl iodide of Formula IVb exclusively as the cis-isomer. Typically, the phosphorous ylide can be generated by treatment of the corresponding phosphonium salt with a strong base, such as n-butyllithium or sodium bis(trimethylsilyl)amide. Palladium catalyzed coupling (such as Sonogashira coupling and Negishi coupling) of the cyclosporin vinyl iodide of Formula IVb with various alkynes or alkynylzinc reagents provides the novel cyclosporin alkyne of Formula Ib in the cis-configuration. The deacetylation is conducted under the same conditions as described above in Scheme 2.

Scheme 3

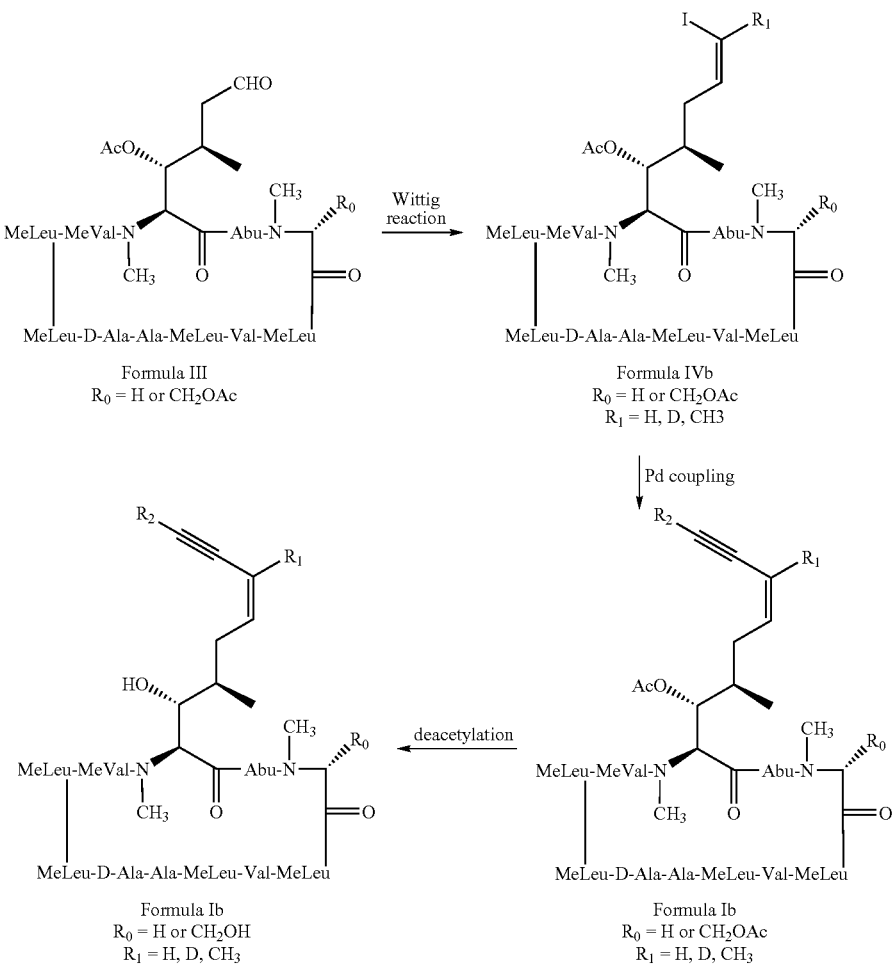

Formula III
R₀ = H or CH₂OAc

Formula IVb
R₀ = H or CH₂OAc
R₁ = H, D, CH3

Formula Ib
R₀ = H or CH₂OH
R₁ = H, D, CH3

Formula Ib
R₀ = H or CH₂OAc
R₁ = H, D, CH3

According to another embodiment of the present invention, cyclosporin alkyne analogues can be prepared by the application of phosphorus chemistry (such as Wittig reaction), as shown in Scheme 4. This chemistry converts the cyclosporin aldehyde of Formula III to a mixture of cis and trans geometric isomers of cyclosporin alkyne analogues of Formula I, which is difficult to be separated. Typically, the phosphorous ylide species under Wittig or Horner-Emmons conditions are generated by treatment of various phosphonium salts or phosphonates with a strong base, such as n-butyllithium or sodium bis(trimethylsilyl)amide. The deacetylation is conducted under the same conditions as described in Scheme 2.

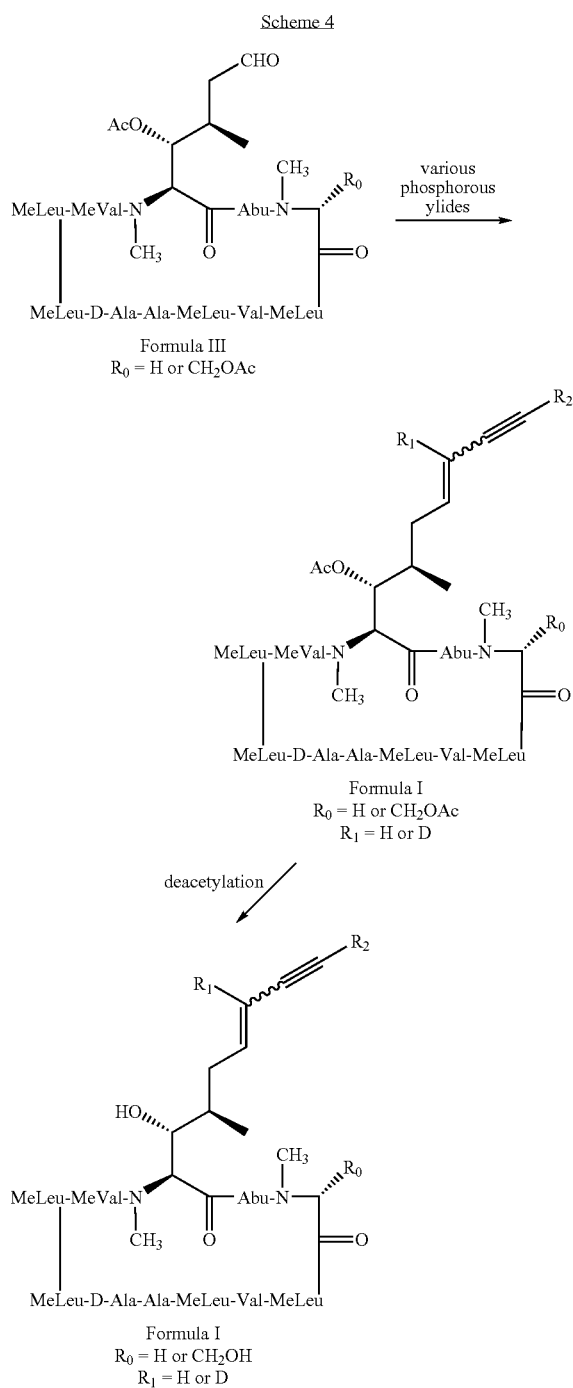

Some of the compounds disclosed in the present invention are useful as immunosuppressive agent. Administration of these compounds suppresses the immune response in organ transplant patients and, thus, prevents allograft rejection. The compounds of the present invention possess enhanced immunosuppressive activity over cyclosporin A. For example, as shown in FIG. 1, the novel cyclosporin alkyne analogue compound disclosed in Example 5 demonstrates immunosuppressive activity up to two times more potent (as determined by $IC_{50}$) over $ISA_{TX}247$ and up to three or four times more active, compared to cyclosporin A, while the cyclosporin alkyne analogue compound disclosed in Example 33 is up to two times more active over cyclosporin A and equipotent to $ISA_{TX}247$ in the concanavalin A (ConA) stimulated murine splenocyte assay. Table 1 shows the immunosuppressive activities of several novel cyclosporin alkyne analogue compounds disclosed in the present application. (The third column in Table 1 contains Cyclosporin A positive control values included for comparison.)

TABLE 1

Immunosuppressive Activity of Novel Cyclosporin Alkyne Analogue Compounds of the Present Invention

| Example where the Novel Cyclosporin Alkyne Analogue Compound is Disclosed | $IC_{50}$ (ng/mL) | $IC_{50}$ (ng/mL) of CsA |
|---|---|---|
| Example 5 | 6 | 20 |
| Example 6 | 6 | 23 |
| Example 13 | 1 | 15 |
| Example 15 | 8 | 17 |
| Example 27 | 6 | 9 |
| Example 28 | 7 | 5 |
| Example 33 | 9 | 20 |
| Example 71 | 4 | 15 |
| Example 73 | 6 | 15 |
| Example 79 | 11 | 15 |
| Example 83 | 10 | 15 |
| Example 89 | 15 | 17 |

The compounds disclosed in the present invention are useful for the prevention or treatment of viral-induced disorders that are dependent upon the presence of cyclophilin A. The compounds of the present invention used to treat these viral infections may possess potent immunosuppressive activity (via inhibition of calcineurin) or may be completely devoid of immunosuppressive activity (do not inhibit calcineurin). However, the mechanism that the immunosuppressive and non-immunosuppressive cyclosporin compounds share is their activity at cyclophilin A.

Cyclophilin A enzyme activity, i.e., peptidyl-prolyl cis-trans isomerase activity, is important to the folding and trafficking of proteins. The HIV infectivity of CD4+ T-cells and viral replication are dependent upon the incorporation of cyclophilin A into HIV-1 virions through interactions with the Gag polyprotein. Inhibition of the cyclophilin A enzyme activity is necessary and sufficient for anti-HIV-1 activity.

In one embodiment of the present invention, the viral-induced disorder is a human immunodeficiency virus (HIV)-induced disorder. Thus, compounds of the present invention that lack immunosuppressant activity as determined by the Concanavalin A (Con A)-stimulated murine splenocyte assay but retain potent peptidyl prolyl isomerase (PPIase) inhibitory (cyclophilin A) activity may possess anti-HIV activity. In addition, compounds of the present invention that have immunosuppressive activity as determined by the Con A-stimulated murine splenocyte assay and also possess potent PPIase inhibitory (cyclophilin A) activity may possess anti-HIV activity.

In vitro biological assays that allow the determination of binding affinity to cyclophilin A or allow the determination of inhibition of peptidyl cis-trans isomerase activity are described in Handschumacher et al., "Cyclophilin: A Specific Cytosolic Binding Protein for Cyclosporin A," *Science* 226: 544-547 (1984) and Kofron et al., "Determination of Kinetic Constants for Peptidyl Prolyl Cis-Trans Isomerases by an Improved Spectrophotometric Assay," *Biochemistry* 30:6127-6134 (1991), respectively, which are both hereby incorporated by reference in their entirety.

The in vitro anti-HIV activity of compounds of the present invention can be measured in established cell line cultures as described by Mayaux et al., "Triterpene Derivatives That Block Entry of Human Immunodeficiency Virus Type 1 Into Cells," *Proc. Natl. Acad. Sci. USA* 91:3564-3568 (1994), which is hereby incorporated by reference in its entirety.

In another embodiment of the present invention, the compound of the present invention is administered in combination with antiretroviral agents, such as nucleoside reverse transcriptase inhibitors, nonnucleoside reverse transcriptase inhibitors, human immunodeficiency virus protease inhibitors, fusion inhibitors, and combinations thereof. Examples of nucleoside reverse transcriptase inhibitors include, but are not limited to, Zidovudine, Didanosine, Stavudine, and Lamivudine. Examples of nonnucleoside reverse transcriptase inhibitors include, but are not limited to, Nevirapine, Efavirenz, and Delavirdine. Examples of human immunodeficiency virus protease inhibitors include, but are not limited to, Saquinovir, Indinavir, and Ritonavir. Examples of fusion inhibitors include, but are not limited to, Enfuvirtide.

Although cyclophilin PPIase activity would appear to be implicated in anti-HCV activity as it is for anti-HIV-1 activity, the hepatitis C virus (HCV) proteins that may interact with cyclophilin A have yet to be identified. In another embodiment of the present invention, the viral-induced disorder is a HCV-induced disorder. Hepatitis C infections or HCV induced disorders are, for example, chronic hepatitis, liver cirrhosis, or liver cancer (e.g., hepatocellular carcinoma). Thus, compounds of the present invention that lack immunosuppressant activity as determined by the Concanavalin A (Con A)-stimulated murine splenocyte assay but retain potent peptidyl prolyl isomerase (PPIase) inhibitory (cyclophilin A) activity may possess anti-HCV activity. In addition, compounds of the present invention that have immunosuppressive activity as determined by the Con A-stimulated murine splenocyte assay and also possess potent PPIase inhibitory (cyclophilin A) activity may possess anti-HCV activity. The compounds of the present invention may also be used as a prophylactic treatment for neonates born to HCV-infected mothers, for healthcare workers exposed to the virus, or for transplant recipients, e.g., organ or tissue transplant (e.g. liver transplant) recipients, to eliminate possible recurrent infection after transplantation.

In another embodiment of the present invention, the compound of the present invention is administered in combination with an interferon. Examples of interferons include, but are not limited to, interferon α2a and interferon α2b. The interferon can be a pegylated interferon. Examples of interferons include, but are not limited to, pegylated interferon α2a or pegylated interferon α2b.

Utility of the immunosuppressive or non-immunosuppressive cyclosporin compounds of the present invention in treating diseases or conditions from HCV infection can be demonstrated in standard animal or clinical tests in accordance with the methods described in Examples 102 and 103, for example.

Some of the compounds disclosed in the present invention also possess utility in the treatment of autoimmune and chronic inflammatory diseases such as asthma, rheumatoid arthritis, multiple sclerosis, psoriasis, and ulcerative colitis, to name only a few.

The compounds disclosed in the present invention are also useful for the treatment of ocular allergy and dry eye. Allergan is currently marketing a topical formulation of cyclosporin A called RESTASIS™ (cyclosporin ophthalmic emulsion) for the treatment of keratoconjunctivitis sicca or chronic dry eye syndrome in patients whose tear production is presumed to be suppressed due to ocular inflammation. While the exact mechanism of RESTASIS™ is unknown, it is thought to act as an immunomodulator with anti-inflammatory effects ("Annual Update 2003: Ophthalmic Drugs" *Drugs of the Future*, 28(3): 287-307 (2003); Clark et al., "Ophthalmic Drug Discovery," *Nature Reviews in Drug Discovery*, 2:448-459 (2003), which are hereby incorporated by reference in their entirety).

For treatment of the above mentioned diseases, therapeutically effective doses of the compounds of the present invention may be administered orally, topically, parenterally, by inhalation spray, or rectally in dosage unit formulations containing conventional non-toxic pharmaceutically acceptable carriers, adjuvants, and vehicles. The term parenteral, as used herein, includes subcutaneous injections, intravenous, intramuscular, intrasternal injection, or infusion techniques.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. The pharmaceutical compositions of the present invention contain the active ingredient formulated with one or more pharmaceutically acceptable carriers. As used herein, the term "pharmaceutical acceptable carrier" means a non-toxic, inert solid, semi-solid or liquid filler, diluent, encapsulating material, or formulation auxiliary of any type. Some examples of pharmaceutically acceptable carriers are sugars such as lactose, glucose, and sucrose; starches such as corn starch or potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic, compatible lubricants such as sodium lauryl sulfate and magnesium stearate; as well as coloring agents, releasing agents, sweetening, and flavoring and perfuming agents. Preservatives and antioxidants, such as ethyl or n-propyl p-hydroxybenzoate, can also be included in the pharmaceutical compositions.

Dosage forms for topical or transdermal administration of compounds disclosed in the present invention include ointments, pastes, creams, lotions, gels, plasters, cataplasms, powders, solutions, sprays, inhalants, or patches. The active component is admixed under sterile conditions with a pharmaceutically acceptable carrier and any needed preservatives or buffers, as may be required. The ointments, pastes, creams and gels may contain, in addition to an active compound of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

For nasal administration, the compounds disclosed in the present invention can be administered, as suitable, in liquid or powdered form from a nasal applicator. Forms suitable for ophthalmic use will include lotions, tinctures, gels, ointment and ophthalmic inserts, as known in the art. For rectal administration (topical therapy of the colon), the compounds of the present invention may be administered in suppository or enema form, in solution in particular, for example in vegetable oil or in an oily system for use as a retention enema.

Compounds disclosed in the present invention may be delivered to the lungs by the inhaled route either in nebulizer form or as a dry powder. The advantage of the inhaled route, over the systemic route, in the treatment of asthma and other diseases of airflow obstruction and/or chronic sinusitis, is that patients are exposed to very small quantities of the drug and the compound is delivered directly to the site of action.

Dosages of the compounds of the present invention employed for the treatment of the maladies identified in the present invention will vary depending on the site of treatment, the particular condition to be treated, the severity of the condition, the subject to be treated (who may vary in body weight, age, general health, sex, and other factors) as well as the effect desired.

Dosage levels ranging from about 0.05 mg to about 50 mg per kilogram of body weight per day are useful for the treatment of the conditions or diseases identified in the present invention. This means the amount of the compound disclosed in the present invention that is administered will range from 2.5 mg to about 2.5 gm per patient per day.

The amount of active ingredient that may be combined with the pharmaceutical carrier materials to produce a single dosage form will vary depending upon the host treated and the particular mode of administration. For example, a formulation intended for the oral administration of humans may contain from 2.5 mg to 2.5 gm of active compound of the present invention compounded with an appropriate and convenient amount of carrier material which may vary from about 5 to 95 percent of the total composition. Dosage unit forms will generally contain between from about 5 mg to about 500 mg of active compound of the present invention. Dosage for topical preparation will, in general be less (one tenth to one hundredth) of the dose required for an oral preparation.

EXAMPLES

Example 1

Preparation of Cyclosporin Acetate

A solution of cyclosporin A (5.0 g, 4.16 mmol), acetic anhydride (7.80 mL, 83.2 mmol), and DMAP (760 mg, 6.2 mmol) in methylene chloride (40 mL) was stirred overnight at room temperature under $N_2$ atmosphere. Saturated sodium bicarbonate solution (200 mL) was added to the solution and stirred for an additional 2 h. The mixture was extracted with ether, washed with 1 N HCl, neutralized with saturated sodium bicarbonate solution, washed with brine, dried over sodium sulfate, and concentrated in vacuo to afford cyclosporin acetate (4.92 g, 95%) as a white solid: $^1$H NMR (300 MHz, $CDCl_3$) δ 8.57 (d, J=9.6 Hz, 1H), 8.04 (d, J=6.9 Hz, 1H), 7.51 (d, J=9.4 Hz, 1H), 7.47 (d, J=7.8 Hz, 1H), 5.67 (dd, J=11.0, 4.0 Hz, 1H), 5.60-5.44 (m, 2H), 5.39 (dd, J=11.7, 3.7 Hz, 1H), 5.32-5.13 (m, 4H), 5.06-4.93 (m, 2H), 4.85 (t, J=7.2 Hz, 1H), 4.77 (t, J=9.6 Hz, 1H), 4.65 (d, J=13.7 Hz, 1H), 4.41 (t, J=7.0 Hz, 1H), 3.46 (s, 3H), 3.26 (s, 3H), 3.24 (s, 3H), 3.21 (s, 3H), 3.10 (s, 3H), 2.68 (s, 3H), 2.66 (s, 3H), 2.50-2.35 (m, 1H), 2.25-1.80 (m, 6H), 2.08 (s, 3H), 2.01 (s, 3H), 1.75-1.55 (m, 6H), 1.45-0.75 (m, 55H); ESI MS m/z 1245 $[C_{64}H_{113}N_{11}O_{13}+H]^+$.

Example 2

Preparation of Acetyl Cyclosporin Aldehyde

Ozone was bubbled into a solution of cyclosporin acetate from Example 1 (3.0 g, 2.4 mmol) in methylene chloride (70 mL) at −78° C. until a blue color was developed. The mixture was degassed with nitrogen for a few min and dimethylsulfide (3 mL) was added at −78° C. The reaction mixture was allowed to warm to room temperature and stirred for 3 h. The reaction mixture was concentrated in vacuo and the residue was dissolved in ethyl acetate (300 mL), washed with water (2×70 mL) and brine (70 mL), dried over sodium sulfate, filtered, and concentrated in vacuo to afford acetyl cyclosporin aldehyde (2.79 g, 94%) as a white solid. The crude was carried to the next step without further purification: $^1$H NMR (300 MHz, $CDCl_3$) δ 9.60 (d, J=3.5 Hz, 1H), 8.55 (d, J=9.7 Hz, 1H), 7.96 (d, J=6.8 Hz, 1H), 7.52 (d, J=7.7 Hz, 1H), 7.46 (d, J=9.0 Hz, 1H), 5.67 (dd, J=11.0, 3.8 Hz, 1H), 5.60-5.45 (m, 2H), 5.32 (dd, J=12.1, 3.3 Hz, 1H), 5.24-5.10 (m, 2H), 5.08-4.90 (m, 2H), 4.84 (t, J=7.1 Hz, 1H), 4.73 (t, J=9.6 Hz, 1H), 4.64 (d, J=13.8 Hz, 1H), 4.41 (t, J=7.0 Hz, 1H), 3.46 (s, 3H), 3.29 (s, 6H), 3.21 (s, 3H), 3.08 (s, 3H), 2.67 (s, 3H), 2.65 (s, 3H), 2.50-2.35 (m, 2H), 2.25-1.80 (m, 6H), 1.99 (s, 3H), 1.75-1.55 (m, 3H), 1.50-0.75 (m, 57H); ESI MS m/z 1233 $[C_{62}H_{109}N_{11}O_{14}+H]^+$.

Example 3

Preparation of Trans Acetyl Cyclosporin Vinyl Iodide

To an ice-cooled suspension of chromium(II) chloride (1.0 g, 8.2 mmol) in THF (25 mL) was added a solution of acetyl cyclosporin aldehyde from Example 2 (0.50 g, 0.41 mmol) and iodoform (1.29 g, 3.28 mmol) in THF (25 mL). After 7 h at 0° C., the reaction mixture was poured into ice-water (50 mL). The water layer was extracted with ethyl acetate (3×60 mL). The combined organics were dried over anhydrous sodium sulfate and concentrated. The material was purified by semi-preparative HPLC to afford trans acetyl cyclosporin vinyl iodide (290 mg, 52%) as a white solid: $^1$H NMR (300 MHz, $CDCl_3$) δ 8.47 (d, J=9.8 Hz, 1H), 8.01 (d, J=6.4 Hz, 1H), 7.56 (d, J=8.8 Hz, 1H), 7.54 (d, J=7.5 Hz, 1H), 6.50-6.40 (m, 1H), 5.84 (d, J=14.3 Hz, 1H), 5.69-5.10 (m, 6H), 4.97 (d, J=11.1 Hz, 2H), 4.87-4.73 (m, 2H), 4.64 (d, J=13.8 Hz, 1H), 4.43 (t, J=7.0 Hz, 1H), 3.43 (s, 3H), 3.28 (s, 3H), 3.26 (s, 3H), 3.20 (s, 3H), 3.12 (s, 3H), 2.68 (s, 3H), 2.66 (s, 3H), 2.45-2.35 (m, 1H), 2.28-1.80 (m, 8H), 2.06 (s, 3H), 1.77-1.60 (m, 3H), 1.50-0.75 (m, 56H); ESI MS m/z 1357 $[C_{63}H_{110}IN_{11}O_{13}+H]^+$.

Example 4

Preparation of the Acetate of Cyclosporin Alkyne

A mixture of acetyl cyclosporin vinyl iodide from Example 3 (90 mg, 0.066 mmol), CuI (6 mg, 0.033 mmol), and $PdCl_2(PPh_3)_2$ (23 mg, 0.033 mmol) in $Et_3N$ (3 mL) was stirred at room temperature under $N_2$ atmosphere. Reaction mixture was then treated with (trimethylsilyl)acetylene (65 mg, 0.66 mmol). Reaction was allowed to stir for 3 h at room temperature. Solution was filtered through a micro-filter and then concentrated in vacuo. The crude product was purified by semi-preparative HPLC to afford the acetate of cyclosporin alkyne (37 mg, 42%) as an off-white solid: $^1$H NMR (300 MHz, CDCl$_3$) δ 8.47 (d, J=9.6 Hz, 1H), 8.03 (d, J=6.9 Hz, 1H), 7.52 (d, J=9.0 Hz, 1H), 7.47 (d, J=7.7 Hz, 1H), 6.12-6.04 (m, 2H), 5.68 (dd, J=10.9, 3.7 Hz, 2H), 5.53 (s, 1H), 5.48 (s, 1H), 5.36-5.11 (m, 7H), 5.01-4.62 (m, 10H), 4.41 (t, J=7.0 Hz, 2H), 4.06 (t, J=6.6 Hz, 2H), 3.44 (s, 3H), 3.27 (s, 3H), 3.26 (s, 3H), 3.20 (s, 3H), 3.07 (s, 3H), 2.68 (s, 2H), 2.65 (s, 3H), 2.04 (s, 2H), 2.00 (s, 3H), 1.31 (d, J=7.1 Hz, 2H), 1.26 (d, J=7.0 Hz, 2H), 1.06-0.79 (m, 50H), 0.17 (s, 9H); ESI MS m/z 1327 [C$_{68}$H$_{119}$N$_{11}$O$_{13}$Si+H]$^+$.

Example 5

Preparation of Cyclosporin Alkyne

A solution of the acetate of cyclosporin alkyne from Example 4 (37 mg, 0.02 mmol) in methanol (2 mL) was stirred at room temperature. Reaction mixture was treated with potassium carbonate (30 mg, 0.21 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford the cyclosporin alkyne (15 mg, 45%) as a white solid: $^1$H NMR (300 MHz, CDCl$_3$) δ 7.94 (d, J=9.8 Hz, 1H), 7.64 (d, J=7.4 Hz, 1H), 7.41 (d, J=8.3 Hz, 1H), 7.16 (d, J=7.8 Hz, 1H), 6.31-6.20 (m, 2H), 5.70 (dd, J=10.8, 3.7 Hz, 2H), 5.50 (d, J=5.9 Hz, 2H), 5.42 (s, 1H), 5.36 (s, 1H), 5.32 (d, J=3.7 Hz, 1H), 5.28 (d, J=3.9 Hz, 1H), 5.11-4.92 (m, 6H), 4.84 (t, J=7.1 Hz, 2H), 4.47 (s, 1H), 4.75-4.62 (m, 4H), 4.13 (s, 1H), 3.91-3.80 (m, 3H), 3.51 (s, 3H), 3.39 (s, 3H), 3.26 (s, 3H), 3.10 (s, 6H), 2.70 (s, 3H), 2.68 (s, 3H), 1.34 (d, J=7.2 Hz, 2H), 1.29-1.24 (m, 8H), 1.08-0.81 (m, 45H), 0.74 (d, J=6.4 Hz, 2H); ESI MS m/z 1213 [C$_{63}$H$_{109}$N$_{11}$O$_{12}$+H]$^+$; HPLC>99% (AUC), $t_R$=13.58 min.

Example 6

Preparation of Cyclosporin Alkyne

To a solution of 1-propynylmagnesium bromide (7.3 mL, 0.5 M in THF, 3.6 mmol) under stirring and nitrogen was added zinc chloride (3.6 mL, 1 M in ether, 3.6 mmol). After 30 min at room temperature, a solution of acetyl cyclosporin vinyl iodide from Example 3 (500 mg, 0.36 mmol) in THF (5 mL) was added, followed by dichlorobis(triphenylphosphine)palladium(II) (258 mg, 0.36 mmol). After 18 h at room temperature, the solvent was removed under reduced pressure. The crude material was purified by semi-preparative HPLC to afford the acetate of cyclosporin alkyne (335 mg, 71%) as a pale yellow solid: ESI MS m/z 1269 [C$_{66}$H$_{113}$N$_{11}$O$_{13}$+H]$^+$.

To a stirred solution of the above cyclosporin alkyne (335 mg, 0.26 mmol) in methanol (10 mL) was added potassium carbonate (360 mg, 2.6 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford cyclosporin alkyne (53 mg, 16%) as an off-white solid: $^1$H NMR (300 MHz, CDCl$_3$) δ 7.89 (d, J=9.5 Hz, 1H), 7.70 (d, J=7.2 Hz, 1H), 7.50 (d, J=8.2 Hz, 1H), 7.26 (d, J=5.2 Hz, 1H), 6.03-5.93 (m, 1H), 5.70 (dd, J$_1$=4.0 Hz, J$_2$=11.0 Hz, 1H), 5.50 (d, J=5.8 Hz, 1H), 5.40-5.29 (m, 3H), 5.16-4.65 (m, 8H), 4.49 (t, J=7.0 Hz, 1H), 3.82-3.78 (m, 1H), 3.49 (s, 3H), 3.36 (s, 3H), 3.23 (s, 3H), 3.11 (s, 3H), 3.09 (s, 3H), 2.72 (s, 3H), 2.70 (s, 3H), 2.60-0.70 (m, 70H); ESI MS m/z 1227 [C$_{64}$H$_{111}$N$_{11}$O$_{12}$+H]$^+$; HPLC>99% (AUC), $t_R$=14.17 min.

Example 7

Preparation of 1-(Trimethylsilyl)propyne-d$_3$

Trimethylsilylacetylene (4.9 mL, 34.5 mmol) is dissolved in THF (20 mL) and cooled to −78° C. n-BuLi (15.2 mL, 2.5 M in hexanes, 38 mmol) was added to the reaction dropwise and stirred for 0.5 h at −78° C. Iodomethane-d$_3$ (5.0 g, 38 mmol) was added to the reaction dropwise. Resulting mixture was warmed to room temperature over 1 h. Reaction was quenched with water and extracted with ethyl ether (3×100 mL). Combined organics were washed with water, brine, dried over sodium sulfate and distilled using a short path distillation setup to remove most of solvents. Residue was transferred to a small flask and distilled to give 1-(trimethylsilylpropyne-d$_3$ (1.8 g, 32%) as colorless oil: $^1$H NMR (300 MHz, CDCl$_3$) δ 0.13 (s, 9H); ESI MS m/z 116 [C$_6$H$_9$D$_3$Si+H]$^+$.

Example 8

Preparation of Deuterated Cyclosporin Alkyne 1-(Trimethylsilyl)propyne-d$_3$ from Example 7 (64 mg, 0.5 mmol) was dissolved in Et$_3$N (3 mL) and cooled to 0° C. Solution was treated with Bu$_4$NF (0.66 mL, 1 M in THF, 0.66 mmol) and allowed to stir at 0° C. under N$_2$ atmosphere for 10 min. Reaction was allowed to warm to room temperature. After warming, the reaction mixture was treated with acetyl cyclosporin vinyl iodide from Example 3 (75 mg, 0.05 mmol), CuI (5 mg, 0.02 mmol), and PdCl$_2$(PPh$_3$)$_2$ (19 mg, 0.02 mmol). Reaction was kept stirring for 3 h at room temperature. Solution was filtered through a micro-filter and then concentrated in vacuo.

The above crude product (32 mg, 0.025 mmol) was dissolved in methanol (2 mL) and stirred at room temperature. Reaction mixture was treated with potassium carbonate (35 mg, 0.25 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford deuterated cyclosporin alkyne (15 mg, 50%) as a white solid: $^1$H NMR (300 MHz, CDCl$_3$) δ 7.98 (d, J=11.5 Hz, 1H), 7.62 (d, J=7.5 Hz, 1H), 7.42 (d, J=8.3 Hz, 1H), 7.15 (d, J=7.9 Hz, 1H), 6.06-5.96 (m, 2H), 5.70 (dd, J=10.8, 3.8 Hz, 2H), 5.50 (d, J=5.9 Hz, 2H), 5.39 (s, 1H), 5.35-5.28 (m, 2H), 5.13-4.90 (m, 10H), 4.82 (t, J=7.2 Hz, 2H), 4.77 (s, 1H), 4.75-4.62 (m, 6H), 4.50 (t, J=7.0 Hz, 2H), 3.51 (s, 3H), 3.39 (s, 3H), 3.26 (s, 3H), 3.10 (s, 6H), 2.70 (s, 3H), 2.68 (s, 3H), 1.34 (d, J=7.2 Hz, 2H), 1.25 (t, J=3.0 Hz, 4H), 1.09-0.81 (m, 45H), 0.71 (d, J=6.1 Hz, 2H); ESI MS m/z 1230 [C$_{64}$H$_{108}$D$_3$N$_{11}$O$_{12}$+H]$^+$; HPLC>99% (AUC), $t_R$=13.74 min.

Example 9

Preparation of Trans-Cyclosporin Vinyl Iodide

To a stirred solution of trans-acetyl cyclosporin vinyl iodide from Example 3 (200 mg, 0.15 mmol) in methanol (20 mL) was added potassium carbonate (518 mg, 3.75 mmol) at room temperature. After 12 h at room temperature, methanol was evaporated. Water (30 mL) was added and the mixture was extracted with ethyl acetate (3×80 mL). The organic layer was separated, dried over anhydrous sodium sulfate, and concentrated under vacuum to afford crude product. The material was purified by semi-preparative HPLC to afford trans-cyclosporin vinyl iodide (125 mg, 63%) as a white solid: $^1$H NMR (300 MHz, CDCl$_3$) δ 7.90 (d, J=9.3 Hz, 1H), 7.66 (d, J=6.5 Hz, 1H), 7.49 (d, J=8.5 Hz, 1H), 7.18 (d, J=7.8 Hz, 1H), 6.55-6.43 (m, 1H), 5.93 (d, J=14.0 Hz, 1H), 5.69 (d, J=8.1 Hz, 1H), 5.47 (d, J=5.9 Hz, 1H), 5.32 (d, J=8.0 Hz, 1H), 5.12-4.92 (m, 4H), 4.82 (t, J=6.2 Hz, 1H), 4.74 (d, J=14.8 Hz, 1H), 4.67 (t, J=9.1 Hz, 1H), 4.53 (t, J=7.2 Hz, 1H), 3.82 (t, J=6.2 Hz, 1H), 3.50 (s, 3H), 3.37 (s, 3H), 3.25 (s, 3H), 3.11 (s, 6H), 2.72 (s, 3H), 2.69 (s, 3H), 2.48-1.90 (m, 8H), 1.80-1.53 (m, 6H), 1.50-0.72 (m, 55H); ESI MS m/z 1315 [C$_{61}$H$_{108}$IN$_{11}$O$_{12}$+H]$^+$; HPLC>99% (AUC), t$_R$=14.35 min.

Example 10

Preparation of Cyclosporin Alkyne

A mixture of cyclosporin vinyl iodide from Example 9 (82 mg, 0.062 mmol), CuI (6 mg, 0.031 mmol), and PdCl$_2$(PPh$_3$)$_2$ (22 mg, 0.031 mmol) in Et$_3$N (3 mL) was stirred at room temperature under N$_2$ atmosphere. Reaction mixture was then treated with (trimethylsilyl)acetylene (61 mg, 0.62 mmol). Reaction was allowed to stir for 3 h at room temperature. Solution was filtered through a micro-filter and then concentrated in vacuo. The crude product was purified by semi-preparative HPLC to afford cyclosporin alkyne (30 mg, 37%) as an off-white solid: $^1$H NMR (300 MHz, CDCl$_3$) δ 7.89 (d, J=9.7 Hz, 1H), 7.61 (d, J=7.5 Hz, 1H), 7.48 (d, J=8.0 Hz, 1H), 7.13 (d, J=7.8 Hz, 1H), 6.21-6.10 (m, 2H), 5.71 (dd, J=10.5, 3.6 Hz, 2H), 5.53 (d, J=5.3 Hz, 2H), 5.47 (s, 1H), 5.42 (s, 1H), 5.27 (dd, J=11.4, 3.8 Hz, 2H), 5.21-4.99 (m, 6H), 4.93-4.71 (m, 4H), 4.62 (t, J=9.3 Hz, 2H), 4.55 (d, J=7.3 Hz, 2H), 3.51 (s, 3H), 3.38 (s, 3H), 3.26 (s, 3H), 3.10 (s, 3H), 3.09 (s, 3H), 2.70 (s, 3H), 2.69 (s, 3H), 1.34 (d, J=7.2 Hz, 2H), 1.32-1.24 (m, 9H), 1.08-0.83 (m, 45H), 0.68 (d, J=5.7 Hz, 2H), 0.17 (s, 9H); ESI MS m/z 1285 [C$_{66}$H$_{117}$N$_{11}$O$_{12}$Si+H]$^+$; HPLC 97.1% (AUC), t$_R$=22.14 min.

Example 11

Preparation of Cyclosporin Alkyne

The acetate of cyclosporin alkyne from Example 4 (488 mg, 0.52 mmol) was dissolved in THF (10 mL) and cooled to 0° C. Solution was treated with Bu$_4$NF (6.3 mL, 1 M in THF, 6.3 mmol) and allowed to stir for 20 min under N$_2$ atmosphere. Reaction was quenched with saturated sodium bicarbonate solution and warmed to room temperature. Reaction mixture was extracted with ethyl acetate (3×100 mL). Combined organic layers were washed with brine, dried over sodium sulfate and concentrated in vacuo. The crude product was purified by semi-preparative HPLC to afford cyclosporin alkyne (231 mg, 50%) as an off-white solid: $^1$H NMR (300 MHz, CDCl$_3$) δ 8.51 (d, J=9.7 Hz, 1H), 8.00 (d, J=6.7 Hz, 1H), 7.71-7.63 (m, 2H), 7.56-7.43 (m, 2H), 7.38 (d, J=9.1 Hz, 1H), 6.26-6.15 (m, 2H), 5.67 (dd, J=7.1, 3.8 Hz, 2H), 5.53 (d, J=5.9 Hz, 2H), 5.38 (dd, J=11.9, 3.9 Hz, 2H), 5.31-5.26 (m, 2H), 5.14 (t, J=7.6 Hz, 2H), 4.97 (d, J=11.0 Hz, 2H), 4.94-4.73 (m, 4H), 4.46-4.33 (m, 8H), 3.44 (s, 3H), 3.27 (s, 3H), 3.25 (s, 3H), 3.21 (s, 3H), 3.09 (s, 3H), 2.67 (s, 3H), 2.65 (s, 3H), 2.01 (s, 3H), 1.32-1.23 (m, 4H), 1.06-0.70 (m, 50H); ESI MS m/z 1255 [C$_{65}$H$_{111}$N$_{11}$O$_{13}$+H]$^+$.

Example 12

Preparation of the Acetate of Cyclosporin Alkynyl Iodide

A mixture of cyclosporin alkyne from Example 11 (65 mg, 0.05 mmol) and CuI (100 mg, 0.52 mmol) in THF (3 mL) was cooled to −15° C. Bis-(trimethylsilyl)peroxide (90 mg, 0.52 mmol) was added to the reaction dropwise under N$_2$ atmosphere. The reaction was kept stirring at −15° C. for 15 min and then allowed to warm to room temperature. Reaction was heated to 50° C. and stirred overnight. Reaction mixture was diluted with THF, washed with a saturated solution of ammonium chloride, washed with brine, dried over sodium sulfate, and concentrated in vacuo. The crude product was purified by semi-preparative HPLC to afford the acetate of cyclosporin alkynyl iodide (8 mg, 11%) as an off-white solid: $^1$H NMR (300 MHz, CDCl$_3$) δ 8.44 (d, J=9.6 Hz, 1H), 8.02 (d, J=6.6 Hz, 1H), 7.64 (d, J=9.3 Hz, 1H), 7.58 (d, J=7.5 Hz, 1H), 6.09-5.98 (m, 2H), 5.68 (d, J=11.1 Hz, 2H), 5.55-5.06 (m, 10H), 5.97 (d, J=10.9 Hz, 2H), 4.88-4.72 (m, 8H), 4.64 (d, J=13.7 Hz, 2H), 4.44 (t, J=6.8 Hz, 2H), 3.43 (s, 3H), 3.25 (s, 3H), 3.23 (s, 3H), 3.19 (s, 3H), 3.10 (s, 3H), 2.68 (s, 3H), 2.66 (s, 3H), 2.01 (s, 3H), 1.40-1.25 (m, 4H), 1.10-0.71 (m, 50H); ESI MS m/z 1381 [C$_{65}$H$_{110}$IN$_{11}$O$_{13}$+H]$^+$.

Example 13

Preparation of Cyclosporin Alkynyl Iodide

A solution of the acetate of cyclosporin alkynyl iodide from Example 12 (8 mg, 0.006 mmol) in methanol (1 mL) was stirred at room temperature. Reaction mixture was treated with potassium carbonate (20 mg, 0.14 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl iodide (3.2 mg, 46%) as a white solid: $^1$H NMR (300 MHz, CDCl$_3$) δ 7.95 (d, J=9.7 Hz, 1H), 7.64 (d, J=7.4 Hz, 1H), 7.47 (d, J=8.0 Hz, 1H), 7.21 (d, J=7.7 Hz, 1H), 6.23-6.20 (m, 2H), 5.70 (dd, J=10.8, 3.7 Hz, 2H), 5.55 (s, 1H), 5.48 (d, J=6.0 Hz, 2H), 5.28 (dd, J=11.3, 3.7 Hz, 2H), 5.14-4.91 (m, 6H), 4.82 (t, J=7.2 Hz, 2H), 4.77 (s, 1H), 4.70-4.62 (m, 3H), 4.52 (t, J=7.1 Hz, 2H), 3.81 (d, J=6.4 Hz, 2H), 3.50 (s, 3H), 3.39 (s, 3H), 3.26 (s, 3H), 3.10 (s, 6H), 2.69 (s, 3H), 2.68 (s, 3H), 1.34 (d, J=7.2 Hz, 2H), 1.31-1.22 (m, 9H), 1.08-0.80 (m, 45H), 0.72 (d, J=6.5 Hz, 2H); ESI MS m/z 1339 [C$_{63}$H$_{108}$IN$_{11}$O$_{12}$+H]$^+$; HPLC 95.4% (AUC), t$_R$=19.54 min.

Example 14

Preparation of the Acetate of Cyclosporin Alkynyl Bromide

A solution of cyclosporin alkyne from Example 11 (96 mg, 0.08 mmol) and CuBr (328 mg, 2.3 mmol) in THF (4 mL) was cooled to −15° C. Bis(trimethylsilyl)peroxide (408 mg, 2.3 mmol) was added to the reaction dropwise, under N$_2$ atmosphere. Reaction mixture was kept stirring at −15° C. for 20 min, then allowed to warm to room temperature and stirred an additional 5 h. Reaction was quenched with saturated ammonium chloride solution and extracted with ethyl acetate. Organic layer washed with brine, dried over sodium sulfate, and concentrated in vacuo. The crude product was purified by semi-preparative HPLC to afford the acetate of cyclosporin alkynyl bromide (19 mg, 69%) as an off-white solid: ESI MS m/z 1333 $[C_{65}H_{110}BrN_{11}O_{13}+H]^+$.

Example 15

Preparation of Cyclosporin Alkynyl Bromide

A solution of the acetate of cyclosporin alkynyl bromide from Example 14 (19 mg, 0.01 mmol) in methanol (2 mL) was stirred at room temperature. Reaction mixture was treated with potassium carbonate (30 mg, 0.22 mmol) and was allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl bromide (8 mg, 43%) as a white solid: $^1$H NMR (300 MHz, CDCl$_3$) δ 7.96 (d, J=9.7 Hz, 1H), 7.65 (d, J=7.2 Hz, 1H), 7.43 (d, J=8.1 Hz, 1H), 7.18 (d, J=7.8 Hz, 1H), 6.24-6.14 (m, 2H), 5.73-5.68 (m, 1H), 5.48 (d, J=6.2 Hz, 2H), 5.40 (s, 1H), 5.35 (s, 1H), 5.29 (dd, J=11.7, 3.8 Hz, 2H), 5.07 (d, J=10.7 Hz, 2H), 5.01-4.93 (m, 3H), 4.85 (t, J=7.2 Hz, 2H), 4.74 (s, 1H), 4.69 (s, 1H), 4.63 (s, 1H), 4.49 (t, J=7.2 Hz, 2H), 3.83 (t, J=6.5 Hz, 2H), 3.50 (s, 3H), 3.39 (s, 3H), 3.26 (s, 3H), 3.10 (s, 6H), 2.70 (s, 3H), 2.68 (s, 3H), 2.00 (s, 6H), 1.35 (d, J=7.1 Hz, 2H), 1.26 (d, J=4.0 Hz, 3H), 1.08-0.80 (m, 48H), 0.74 (d, J=6.4 Hz, 1H); ESI MS m/z 1291 $[C_{63}H_{108}BrN_{11}O_{12}+H]^+$; HPLC 96.9% (AUC), $t_R$=20.07 min.

Example 16

Preparation of the Acetate of Cyclosporin Alkynyl Amine

A mixture of acetyl cyclosporin vinyl iodide from Example 3 (60 mg, 0.044 mmol), CuI (4 mg, 0.022 mmol), and PdCl$_2$(PPh$_3$)$_2$ (15 mg, 0.022 mmol) in Et$_3$N (3 mL) was stirred at room temperature under $N_2$ atmosphere. Reaction mixture was then treated with N-methylpropargylamine (30 mg, 0.44 mmol). Reaction was allowed to stir for 6 h at room temperature. Solution was filtered through a micro-filter and then concentrated in vacuo. The crude product was purified by semi-preparative HPLC to afford the acetate of cyclosporin alkynyl amine (9.5 mg, 17%) as an off-white solid: $^1$H NMR (300 MHz, CDCl$_3$) δ 8.45 (d, J=9.7 Hz, 1H), 7.99 (d, J=6.9 Hz, 1H), 7.44 (t, J=8.0 Hz, 2H), 5.98-5.89 (m, 2H), 5.67 (dd, J=10.8, 3.6 Hz, 2H), 5.51 (d, J=3.0 Hz, 2H), 5.40-5.23 (m, 7H), 5.14 (t, J=7.6 Hz, 2H), 5.00-4.74 (m, 10H), 4.63 (d, J=13.8 Hz, 2H), 4.42 (t, J=7.0 Hz, 2H), 4.10 (s, 1H), 3.44 (s, 3H), 3.26 (s, 3H), 3.24 (s, 3H), 3.20 (s, 3H), 3.08 (s, 3H), 2.67 (s, 3H), 2.65 (s, 3H), 2.57 (s, 2H), 2.02 (s, 3H), 2.01 (s, 2H), 1.30 (t, J=6.8 Hz, 2H), 1.25 (s, 2H), 1.06-0.78 (m, 50H); ESI MS m/z 1298 $[C_{67}H_{116}N_{12}O_{13}+H]^+$.

Example 17

Preparation of Cyclosporin Alkynyl Amine

A solution of the acetate of cyclosporin alkynyl amine from Example 16 (9.5 mg, 0.007 mmol) in methanol (2 mL) was stirred at room temperature. Reaction mixture was treated with potassium carbonate (11 mg, 0.07 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl amine (4.5 mg, 49%) as a white solid: $^1$H NMR (300 MHz, CDCl$_3$) δ 8.00 (d, J=10.6 Hz, 1H), 7.65 (d, J=8.5 Hz, 1H), 7.61 (d, J=6.9 Hz, 1H), 7.21 (d, J=7.9 Hz, 1H), 6.15-6.04 (m, 2H), 5.67 (dd, J=11.0, 4.1 Hz, 2H), 5.54-5.38 (m, 2H), 5.33 (d, J=8.1 Hz, 1H), 5.08-4.63 (m, 6H), 4.85-4.63 (m, 8H), 4.61 (s, 1H), 1.50 (t, J=7.2 Hz, 2H), 4.41 (s, 1H), 4.26 (d, J=1.7 Hz, 2H), 4.14 (d, J=1.7 Hz, 2H), 4.08-3.97 (m, 2H), 3.50 (s, 3H), 3.40 (s, 3H), 3.24 (s, 3H), 3.12 (s, 3H), 3.11 (s, 3H), 2.67 (s, 3H), 2.66 (s, 3H), 2.00 (s, 2H), 1.54 (d, J=9.6 Hz, 2H), 1.46 (s, 1H), 1.38-1.25 (m, 6H), 1.05-0.80 (m, 45H), 0.77 (d, J=6.5 Hz, 2H); ESI MS m/z 1256 $[C_{65}H_{114}N_{12}O_{12}+H]^+$; HPLC 98.8% (AUC), $t_R$=12.28 min.

Example 18

Preparation of the Acetate of Cyclosporin Alkynyl Amine

A mixture of acetyl cyclosporin vinyl iodide from Example 3 (60 mg, 0.044 mmol), CuI (4 mg, 0.022 mmol), and PdCl$_2$(PPh$_3$)$_2$ (15 mg, 0.022 mmol) in Et$_3$N (3 mL) was stirred at room temperature under $N_2$ atmosphere. Reaction mixture was then treated with 1-(dimethylamino)-2-propyne (38 mg, 0.44 mmol). Reaction was allowed to stir for 6 h at room temperature. Solution was filtered through a micro-filter and then concentrated in vacuo. The crude product was purified by semi-preparative HPLC to afford the acetate of cyclosporin alkynyl amine (33 mg, 56%) as an off-white solid: $^1$H NMR (300 MHz, CDCl$_3$) δ 8.49 (d, J=9.6 Hz, 1H), 8.02 (d, J=6.8 Hz, 1H), 7.45 (t, J=7.7 Hz, 2H), 6.06-5.95 (m, 2H), 5.67 (dd, J=1.0, 3.8 Hz, 2H), 5.52 (d, J=6.8 Hz, 2H), 5.36 (s, 1H), 5.31 (s, 1H), 5.14 (t, J=7.6 Hz, 2H), 5.00-4.94 (m, 9H), 4.86 (t, J=7.3 Hz, 2H), 4.75 (t, J=9.5 Hz, 2H), 4.65 (d, J=13.8 Hz, 2H), 4.41 (t, J=7.0 Hz, 2H), 4.12 (dd, J=14.2, 7.1 Hz, 2H), 3.44 (s, 3H), 3.26 (s, 3H), 3.25 (s, 3H), 3.21 (s, 3H), 3.07 (s, 3H), 2.67 (s, 2H), 2.65 (s, 3H), 2.32 (s, 6H), 2.04 (s, 2H), 2.01 (s, 3H), 1.31 (d, J=7.1 Hz, 2H), 1.26 (d, J=6.8 Hz, 2H), 1.06-0.59 (m, 50H); ESI MS m/z 1312 $[C_{68}H_{118}N_{12}O_{13}+H]^+$.

Example 19

Preparation of Cyclosporin Alkynyl Amine

A solution of the acetate of cyclosporin alkynyl amine from Example 18 (33 mg, 0.02 mmol) in methanol (3 mL) was stirred at room temperature. Reaction mixture was treated with potassium carbonate (34 mg, 0.2 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl amine (17 mg, 55%) as a white solid: $^1$H NMR (300 MHz, CDCl$_3$) δ 7.98 (d, J=9.7 Hz, 1H), 7.64 (d, J=7.6 Hz, 1H), 7.48 (d, J=8.1 Hz, 1H), 7.12 (d, J=7.9 Hz, 1H), 6.21-6.12 (m, 2H), 5.70 (dd, J=10.7, 3.6 Hz, 2H), 5.43 (d, J=5.7 Hz, 2H), 5.47 (s, 1H), 5.42 (s, 1H), 5.28 (dd, J=11.5, 3.8 Hz, 2H), 5.11-4.99 (m, 8H), 4.92 (dd, J=9.7, 6.0 Hz, 2H), 4.82 (t, J=7.4 Hz, 2H), 4.75 (s, 2H), 4.70 (s, 2H), 4.63 (t, J=9.4 Hz, 2H), 4.54 (t, J=7.3 Hz, 2H), 3.51 (s, 3H), 3.39 (s, 3H), 3.26 (s, 3H), 3.11 (s, 3H), 3.10 (s, 3H), 2.70 (s, 3H), 2.68 (s, 3H), 2.55 (s, 3H), 1.34 (d, J=7.2 Hz, 2H), 1.30-1.24 (m, 9H), 1.09-0.81 (m, 45H), 0.70 (d, J=6.0

Hz, 2H); ESI MS m/z 1270 $[C_{66}H_{116}N_{12}O_{12}+H]^+$; HPLC>99% (AUC), $t_R$=12.37 min.

Example 20

Preparation of the Acetate of Cyclosporin Alkynyl Alcohol

A mixture of acetyl cyclosporin vinyl iodide from Example 3 (300 mg, 0.22 mmol), CuI (21 mg, 0.11 mmol), and PdCl$_2$(PPh$_3$)$_2$ (39 mg, 0.055 mmol) in Et$_3$N (5 mL) was stirred at room temperature under N$_2$ atmosphere. Reaction mixture was then treated with propargyl alcohol (124 mg, 2.2 mmol). Reaction was allowed to stir for 3 h at room temperature. Solution was filtered through a micro-filter and then concentrated in vacuo. The crude product was purified by semi-preparative HPLC to afford the acetate of cyclosporin alkynyl alcohol (100 mg, 36%) as an off-white solid: $^1$H NMR (300 MHz, CDCl$_3$) δ 8.44 (d, J=9.9 Hz, 1H), 7.96 (d, J=6.9 Hz, 1H), 7.43 (d, J=7.9 Hz, 2H), 5.68 (dd, J=10.9, 3.9 Hz, 2H), 5.57 (d, J=10.2 Hz, 1H), 5.27 (d, J=3.3 Hz, 2H), 5.23 (d, J=3.4 Hz, 2H), 5.00-4.80 (m, 8H), 4.64 (s, 1H), 4.60 (s, 1H), 4.46-4.25 (m, 5H), 4.06 (t, J=6.7 Hz, 2H), 3.43 (s, 3H), 3.25 (s, 3H), 3.20 (s, 3H), 3.10 (s, 3H), 2.67 (s, 3H), 2.65 (s, 3H), 2.04 (s, 4H), 2.03 (s, 5H), 1.30 (t, J=7.6 Hz, 2H), 1.25 (s, 5H), 1.06-0.76 (m, 51H); ESI MS m/z 1285 $[C_{66}H_{113}N_{11}O_{14}+H]^+$.

Example 21

Preparation of Cyclosporin Alkynyl Alcohol

A solution of acetate of cyclosporin alkynyl alcohol from Example 20 (32 mg, 0.025 mmol) in methanol (2 mL) was stirred at room temperature. Reaction mixture was treated with potassium carbonate (38 mg, 0.27 mmol) and allowed to keep stirring under N$_2$ atmosphere overnight. The mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl alcohol (21 mg, 68%) as a white solid: $^1$H NMR (300 MHz, CDCl$_3$) δ 7.60 (d, J=9.8 Hz, 1H), 7.40 (d, J=9.0 Hz, 2H), 7.19 (d, J=7.7 Hz, 1H), 6.10-5.99 (m, 1H), 5.66 (dd, J=10.6, 3.8 Hz, 2H), 5.46 (s, 1H), 5.41-5.34 (m, 4H), 5.14-5.02 (m, 6H), 4.89 (d, J=4.6 Hz, 2H), 4.94 (d, J=4.8 Hz, 2H), 4.83-4.66 (m, 4H), 4.44 (t, J=7.1 Hz, 1H), 4.30 (d, J=11.9 Hz, 2H), 4.11-4.02 (m, 4H), 3.50 (s, 3H), 3.39 (s, 3H), 3.23 (s, 3H), 3.10 (s, 3H), 3.09 (s, 3H), 2.68 (s, 6H), 2.18-2.11 (m, 7H) 1.38 (d, J=7.2 Hz, 5H), 1.24 (d, J=6.6 Hz, 6H), 1.06-0.78 (m, 39H); ESI MS m/z 1243 $[C_{64}H_{111}N_{11}O_{13}+H]^+$; HPLC>99% (AUC), $t_R$=13.16 min.

Example 22

Preparation of Cyclosporin Alkynyl Aldehyde

A mixture of the acetate of cyclosporin alkynyl alcohol from Example 20 (100 mg, 0.77 mmol), N-methylmorpholine N-oxide (14 mg, 0.121 mmol), 4 Å molecular sieves (200 mg) was dissolved in methylene chloride (2 mL). Mixture was treated with tetrapropylammonium perruthenate (3 mg, 0.008 mmol) and stirred at room temperature under N$_2$ atmosphere. Mixture was kept stirring for 2 h and then filtered through a pad of silica gel. The filtrate was concentrated in vacuo. The crude product was purified by semi-preparative HPLC to afford cyclosporin alkynyl aldehyde (88 mg, 89%) as an off-white solid: $^1$H NMR (300 MHz, CDCl$_3$) δ 9.32 (s, 1H), 8.46 (d, J=9.5 Hz, 1H), 8.01 (d, J=6.6 Hz, 1H), 7.68 (d, J=8.9 Hz, 1H), 7.58 (d, J=7.5 Hz, 1H), 6.52-6.41 (m, 2H), 5.68 (dd, J=10.8, 3.5 Hz, 2H), 5.53 (d, J=12.7 Hz, 2H), 5.40-5.13 (m, 15H), 4.96 (d, J=11.0 Hz, 2H), 4.64 (d, J=13.8 Hz, 2H), 4.44 (t, J=6.9 Hz, 2H), 3.98 (s, 2H), 3.44 (s, 3H), 3.26 (s, 2H), 3.24 (s, 3H), 3.20 (s, 3H), 3.11 (s, 3H), 2.67 (s, 3H), 2.66 (s, 3H), 2.02 (s, 3H), 1.33-1.19 (m, 4H), 1.06-0.75 (m, 50H); ESI MS m/z 1283 $[C_{66}H_{111}N_{11}O_{14}+H]^+$.

Example 23

Preparation of the Acetate of Trans-Cyclosporin Vinyl Iodide

A solution of cyclosporin alkynyl aldehyde from Example 22 (87 mg, 0.068 mmol) and iodoform (232 mg, 0.68 mmol) in THF (3 mL) was cooled to −78° C. After cooling, dry Cr(II)Cl$_2$ (165 mg, 1.35 mmol) was added to the reaction. The reaction mixture was allowed to warm to 0° C. and stirred under N$_2$ atmosphere for 4 h. Mixture was poured into ice water and extracted with ethyl acetate (3×100 mL). The combined organic layers were washed with brine, dried over sodium sulfate, and concentrated in vacuo. The crude product was purified by semi-preparative HPLC to afford the acetate of trans-cyclosporin vinyl iodide (18 mg, 19%) as an off-white solid: $^1$H NMR (300 MHz, CDCl$_3$) δ 8.38 (d, J=8.9 Hz, 1H), 8.01 (d, J=6.3 Hz, 1H), 7.76 (d, J=8.8 Hz, 1H), 7.63 (d, J=6.7 Hz, 1H), 6.92-6.71 (m, 7H), 6.05-5.94 (m, 2H), 5.52 (d, J=8.0 Hz, 2H), 5.37 (d, J=13.2 Hz, 2H), 5.01-4.55 (m, 10H), 4.47 (t, J=6.9 Hz, 2H), 3.41 (s, 2H), 3.25 (s, 3H), 3.21 (s, 3H), 3.19 (s, 3H), 3.10 (s, 3H), 2.83 (dd, J=10.6, 7.6 Hz, 2H), 2.70 (s, 2H), 2.68 (s, 3H), 2.03 (s, 2H), 2.02 (s, 3H), 1.34-1.25 (m, 7H), 1.06-0.74 (m, 50H); ESI MS m/z 1407 $[C_{67}H_{112}IN_{11}O_{13}+H]^+$.

Example 24

Preparation of Cyclosporin Vinyl Iodide

A solution of the acetate of cyclosporin vinyl iodide from Example 23 (18 mg, 0.012 mmol) in methanol (1 mL) was stirred at room temperature. Reaction mixture was treated with potassium carbonate (50 mg, 0.36 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin vinyl iodide (7.5 mg, 44%) as a white solid: $^1$H NMR (300 MHz, CDCl$_3$) δ 7.91 (d, J=9.7 Hz, 1H), 7.64 (d, J=7.2 Hz, 1H), 7.46 (d, J=8.2 Hz, 1H), 7.21 (d, J=7.8 Hz, 1H), 6.79 (s, 1H), 6.74 (s, 2H), 6.65 (d, J=2.0 Hz, 2H), 6.60 (d, J=2.1 Hz, 1H), 6.22-6.11 (m, 2H), 5.79 (dd, J=10.7, 3.5 Hz, 2H), 5.49-5.26 (m, 3H), 5.11-4.62 (m, 6H), 4.49 (t, J=7.1 Hz, 2H), 4.40 (s, 1H), 4.30-4.20 (m, 2H), 4.14 (d, J=1.7 Hz, 2H), 3.50 (s, 3H), 3.38 (s, 3H), 3.24 (s, 3H), 3.10 (s, 6H), 2.70 (s, 3H), 2.68 (s, 3H), 1.54 (d, J=9.7 Hz, 2H), 1.45 (s, 1H), 1.38-1.25 (m, 9H), 1.07-0.43 (m, 47H); ESI MS m/z 1365 $[C_{65}H_{110}N_{11}O_{12}+H]^+$; HPLC>99% (AUC), $t_R$=14.49 min.

Example 25

Preparation of the Acetate of Cyclosporin Alkynyl Alcohol

A solution of acetyl cyclosporin vinyl iodide from Example 3 (75 mg, 0.055 mmol), CuI (11 mg, 0.055 mmol), and PdCl$_2$(PPh$_3$)$_2$ (39 mg, 0.055 mmol) in Et$_3$N (3 mL) was stirred at room temperature under N$_2$ atmosphere. Reaction mixture was then treated with 3-butyne-2-ol (39 mg, 0.55 mmol). Reaction was allowed to stir for 6 h at room temperature. Solution washed through micro filter and then concentrated in vacuo. The crude product was purified by semi-preparative HPLC to afford the acetate of cyclosporin alkynyl alcohol (15 mg, 21%) as an off-white solid: $^1$H NMR (300 MHz, CDCl$_3$) δ 8.45 (d, J=9.1 Hz, 1H), 7.99 (d, J=6.1 Hz, 1H), 7.40 (d, J=6.9 Hz, 2H), 5.72-5.13 (m, 12H), 5.01-4.39 (m, 10H), 4.26-4.07 (m, 2H), 3.45 (s, 3H), 3.37 (s, 3H), 3.26 (s, 3H), 3.21 (s, 3H), 3.10 (s, 3H), 2.68 (s, 3H), 2.66 (s, 3H), 2.04 (s, 6H), 1.50-1.43 (m, 5H), 1.31 (d, J=7.8 Hz, 10H), 1.26 (s, 5H), 1.08-0.75 (m, 40H); ESI MS m/z 1299 [C$_{67}$H$_{115}$N$_{11}$O$_{14}$+H]$^+$.

Example 26

Preparation of Cyclosporin Alkynyl Alcohol

A solution of acetate of cyclosporin alkynyl alcohol from Example 25 (15 mg, 0.011 mmol) in methanol (1 mL) was stirred at room temperature. Reaction mixture was treated with potassium carbonate (17 mg, 0.13 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl alcohol (5 mg, 36%) as a white solid: $^1$H NMR (300 MHz, CDCl$_3$) δ 7.58 (d, J=10.2 Hz, 1H), 7.41 (d, J=8.0 Hz, 2H), 7.22 (d, J=9.1 Hz, 1H), 6.06-5.94 (m, 2H), 5.66 (dd, J=10.5, 3.2 Hz, 2H), 5.49 (s, 1H), 5.47-5.34 (m, 4H), 5.14-4.91 (s, 7H), 4.80-4.57 (m, 6H), 4.45 (t, J=7.1 Hz, 2H), 4.04 (d, J=7.0 Hz, 2H), 3.50 (s, 3H), 3.38 (s, 3H), 3.23 (s, 3H), 3.10 (s, 3H), 3.08 (s, 3H), 2.69 (s, 6H), 1.42 (d, J=3.2 Hz, 6H), 1.38 (d, J=7.2 Hz, 6H), 1.27-1.24 (m, 8H), 1.07-0.75 (m, 42H); ESI MS m/z 1257 [C$_{65}$H$_{113}$N$_{11}$O$_{13}$+H]$^+$; HPLC>99% (AUC), t$_R$=13.44 min.

Example 27

Preparation of Cyclosporin Ene-Yne-Ene

The acetate of cyclosporin alkynyl alcohol from Example 25 (135 mg, 0.10 mmol) was dissolved in benzene (4 mL) and stirred under N$_2$ atmosphere. Solution was treated with Burgess reagent (98 mg, 0.40 mmol) and stirred at 60° C. for 5 h. Mixture was diluted with ethyl ether, washed with water and brine, dried over sodium sulfate, and concentrated in vacuo.

The above crude product (68 mg, 0.053 mmol) was dissolved in methanol (3 mL) and stirred at room temperature. Reaction mixture was treated with potassium carbonate (60 mg, 0.43 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin ene-yne-ene (47 mg, 72%) as a white solid: $^1$H NMR (300 MHz, CDCl$_3$) δ 7.92 (d, J=9.8 Hz, 1H), 7.63 (d, J=7.5 Hz, 1H), 7.42 (d, J=8.2 Hz, 1H), 7.15 (d, J=7.8 Hz, 1H), 6.16-6.10 (m, 2H), 5.92 (d, J=2.0 Hz, 1H), 5.90 (d, J=2.0 Hz, 1H), 5.86 (d, J=2.0 Hz, 1H), 5.70 (dd, J=10.8, 3.7 Hz, 2H), 5.63 (d, J=2.1 Hz, 1H), 5.78-5.49 (m, 4H), 5.44 (d, J=2.2 Hz, 1H), 5.41 (d, J=2.2 Hz, 1H), 5.29 (dd, J=11.4, 4.1 Hz, 2H), 5.11 (s, 2H), 5.09-4.91 (m, 4H), 4.80 (t, J=7.3 Hz, 2H), 4.71-4.62 (m, 3H), 5.52 (d, J=7.3 Hz, 2H), 3.51 (s, 3H), 3.39 (s, 3H), 3.25 (s, 3H), 3.10 (s, 6H), 2.70 (s, 3H), 2.68 (s, 3H), 1.35 (d, J=7.2 Hz, 2H), 1.27-1.24 (m, 8H), 1.08-0.82 (m, 45H), 0.73 (d, J=6.4 Hz, 2H); ESI MS m/z 1239 [C$_{65}$H$_{111}$N$_{11}$O$_{12}$+H]$^+$; HPLC>99% (AUC), t$_R$=14.24 min.

Example 28

Preparation of Cyclosporin Ene-Yne-Ene

To a stirred solution of trans-acetyl cyclosporin vinyl iodide from Example 3 (130 mg, 0.095 mmol) in triethylamine (6 mL, degassed) were added 1-pentyn-3-ol (80 mg, 0.95 mmol), copper(I) iodide (18 mg, 0.095 mmol) and dichlorobis(triphenylphosphine)palladium(II) (67 mg, 0.095 mmol). After 18 h at room temperature under nitrogen, the mixture was filtered through a 0.2 μm syringe filter and the solvent was removed under reduced pressure. The crude material was purified by flash column chromatography (SiO$_2$, 1:1 acetone/hexanes) to afford cyclosporin alkynyl alcohol (150 mg, ~80% pure by NMR) as a yellowish oil: ESI MS m/z 1313 [C$_{68}$H$_{117}$N$_{11}$O$_{14}$+H]$^+$.

To a solution of the above cyclosporin alkynyl alcohol (150 mg, 0.11 mmol) in benzene (15 mL) under stirring and nitrogen was added Burgess reagent (135 mg, 0.57 mmol). The mixture was stirred at 60° C. for 2 h. As MS monitoring still showed some starting material, some Burgess reagent (135 mg, 0.57 mmol) was added and the reaction was stirred 60° C. for 2 h. After cooling down, the reaction was extracted with ethyl acetate (100 mL) and washed with water. The organic layer was separated, dried over anhydrous sodium sulfate, and concentrated under vacuum to afford the acetate of cyclosporin ene-yne-ene (38 mg), which was carried over without purification: ESI MS m/z 1295 [C$_{68}$H$_{115}$N$_{11}$O$_{13}$+H]$^+$.

To a stirred solution of the above acetate of cyclosporin ene-yne-ene (38 mg, 0.029 mmol) in methanol (3 mL) was added potassium carbonate (30 mg, 0.21 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford cyclosporin ene-yne-ene (3.1 mg, 8%) as a mixture of cis and trans isomers (yellow oil): $^1$H NMR (300 MHz, CDCl$_3$) δ 7.92 (d, J=9.5 Hz, 1H), 7.63 (d, J=7.3 Hz, 1H), 7.45 (d, J=8.0 Hz, 1H), 7.14 (d, J=8.3 Hz, 1H), 6.14-6.05 (m, 1H), 5.95-5.87 (m, 1H), 5.72-5.67 (m, 1H), 5.48-4.65 (m, 17H), 3.92-3.88 (m, 1H), 3.52 (s, 3H), 3.39 (s, 3H), 3.26 (s, 3H), 3.10 (s, 6H), 2.70 (s, 3H), 2.68 (s, 3H), 2.70-0.70 (m, 67H); ESI MS m/z 1253 [C$_{66}$H$_{113}$N$_{11}$O$_{12}$+H]$^+$; HPLC 13.6% and 86.3% (AUC), t$_R$=15.49 and 16.67 min.

Example 29

Preparation of Cyclosporin Ene-Yne-Ene

To a stirred solution of trans-acetyl cyclosporin vinyl iodide from Example 3 (50 mg, 0.036 mmol) in triethylamine (4 mL, degassed) were added 2-methyl-1-buten-3-yne (24 mg, 0.36 mmol), copper(I) iodide (7 mg, 0.036 mmol) and dichlorobis(triphenylphosphine)palladium(II) (26 mg, 0.036 mmol). After 18 h at room temperature under nitrogen, the mixture was filtered through a 0.2 μm syringe filter and the solvent was removed under reduced pressure. The crude material was purified by semi-preparative HPLC to afford the acetate of cyclosporin ene-yne-ene (31 mg, 65%) as a yellowish oil: ESI MS m/z 1295 [C$_{68}$H$_{115}$N$_{11}$O$_{13}$+H]$^+$.

To a stirred solution of the above acetate of cyclosporin ene-yne-ene (31 mg, 0.02 mmol) in methanol (3 mL) was added potassium carbonate (35 mg, 0.25 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford cyclosporin ene-yne-ene (14 mg, 46%) as a yellowish oil: $^1$H NMR (500 MHz, CDCl$_3$) δ 7.93 (d, J=9.5 Hz, 1H), 7.68-7.62 (m, 2H), 7.28 (d, J=7.5 Hz, 1H), 6.17-6.11 (m, 1H), 6.08-6.03 (m, 1H), 5.65-5.58 (m, 2H), 5.56-5.44 (m, 2H), 5.42-4.50 (m, 8H), 3.92-3.90 (m, 1H), 3.78-3.73 (m, 1H), 3.50 (s, 3H), 3.38 (s, 3H), 3.24 (s, 3H), 3.11 (s, 3H), 3.09 (s, 3H), 2.72 (s, 3H), 2.70 (s, 3H), 1.89 (s, 3H), 2.45-0.71 (m, 69H); ESI MS m/z 1253 $[C_{66}H_{113}N_{11}O_{12}+H]^+$; HPLC 96.4% (AUC), $t_R$=16.55 min.

Example 30

Preparation of the Acetate of Cyclosporin Alkynyl Alcohol

A mixture of acetyl cyclosporin vinyl iodide from Example 3 (70 mg, 0.051 mmol), CuI (5 mg, 0.026 mmol), and PdCl$_2$(PPh$_3$)$_2$ (18 mg, 0.026 mmol) in Et$_3$N (3 mL) was stirred at room temperature under N$_2$ atmosphere. Reaction mixture was then treated with 3-butyn-1-ol (37 mg, 0.51 mmol). Reaction was allowed to stir for 4 h at room temperature. Solution was filtered through micro-filter and then concentrated in vacuo. The crude product was purified by semi-preparative HPLC to afford the acetate of cyclosporin alkynyl alcohol (52 mg, 78%) as an off-white solid: $^1$H NMR (300 MHz, CDCl$_3$) δ 8.46 (d, J=9.5 Hz, 1H), 8.04 (d, J=6.9 Hz, 1H), 7.67(d, J=9.2 Hz, 1H), 7.46 (d, J=7.7 Hz, 1H), 5.68 (dd, J=11.2, 4.6 Hz, 2H), 5.58-4.78 (m, 18H), 4.63 (d, J=13.9 Hz, 2H), 4.44 (t, J=6.9 Hz, 2H), 3.98-3.77 (m, 4H), 3.45 (s, 3H), 3.24 (s, 3H), 3.23 (s, 3H), 3.19 (s, 3H), 3.08 (s, 3H), 2.67 (s, 3H), 2.66 (s, 3H), 2.02 (s, 2H), 1.30 (d, J=6.8 Hz, 4H), 1.25 (t, J=2.2 Hz, 4H), 1.05-0.75 (m, 52H); ESI MS m/z 1299 $[C_{67}H_{115}N_{11}O_{14}+H]^+$.

Example 31

Preparation of Cyclosporin Alkynyl Alcohol

A solution of the acetate of cyclosporin alkynyl alcohol from Example 30 (52 mg, 0.04 mmol) in methanol (2 mL) was stirred at room temperature. Reaction mixture was treated with potassium carbonate (60 mg, 0.43 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl alcohol (22 mg, 44%) as a white solid: $^1$H NMR (300 MHz, CDCl$_3$) δ 7.97 (d, J=9.7 Hz, 1H), 7.62 (d, J=7.5 Hz, 1H), 7.49 (d, J=8.4 Hz, 1H), 7.20 (d, J=7.8 Hz, 1H), 5.99-5.88 (m, 2H), 5.69 (dd, J=11.0, 4.0 Hz, 1H), 5.44 (d, J=6.7 Hz, 2H), 5.38 (s, 1H), 5.36 (d, J=3.6 Hz, 1H), 5.32 (d, J=3.9 Hz, 1H), 5.11-4.95 (m, 12H), 4.84 (t, J=7.1 Hz, 2H), 4.72 (s, 1H), 4.68 (t, J=9.8 Hz, 2H), 4.52 (t, J=7.2 Hz, 1H), 3.89 (t, J=6.7 Hz, 1H), 3.74 (t, J=5.7 Hz, 1H), 3.49 (s, 3H), 3.40 (s, 3H), 3.26 (s, 3H), 3.11 (s, 3H), 3.10 (s, 3H), 2.69 (s, 3H), 2.68 (s, 3H), 1.35 (d, J=7.2 Hz, 2H), 1.25 (d, J=2.9 Hz, 4H), 1.07-0.70 (m, 54H); ESI MS m/z 1257 $[C_{65}H_{113}N_{11}O_{13}+H]^+$; HPLC>99% (AUC), $t_R$=17.67 min.

Example 32

Preparation of the Acetate of Cyclosporin Cyclopropyl Alkyne

A solution of cyclopropyl(trimethylsilyl)acetylene (76 mg, 0.55 mmol) in Et$_3$N (3 mL) was cooled to 0° C. Solution was treated with Bu$_4$NF (0.66 mL, 1 M in THF, 0.66 mmol) and allowed to stir at 0° C. under N$_2$ atmosphere for 10 min. Reaction was allowed to warm to room temperature. After warming, the reaction mixture was treated with acetyl cyclosporin vinyl iodide from Example 3 (75 mg, 0.05 mmol), CuI (5 mg, 0.02 mmol), and PdCl$_2$(PPh$_3$)$_2$ (19 mg, 0.02 mmol). Reaction was kept stirring for 3 h at room temperature. Solution was filtered through a micro filter and then concentrated in vacuo. The crude product was purified by semi-preparative HPLC to afford the acetate of cyclosporin cyclopropyl alkyne (58 mg, 82%) as an off-white solid: $^1$H NMR (500 MHz, CDCl$_3$) δ 8.47 (d, J=4.5 Hz, 1H), 8.01 (d, J=3.9 Hz, 1H), 7.63 (d, J=5.4 Hz, 1H), 7.57 (d, J=4.8 Hz, 1H), 5.88-5.81 (m, 2H), 5.69 (dd, J=6.6, 2.4 Hz, 2H), 5.58 (s, 1H), 5.54 (d, J=6.6 Hz, 2H), 5.47 (s, 1H), 5.30-5.20 (m, 2H), 5.17 (d, J=3.6 Hz, 2H), 5.15 (d, J=3.3 Hz, 2H), 5.08-4.80 (m, 9H), 4.63 (s, 2H), 4.47 (t, J=4.2 Hz, 2H), 4.13 (dd, J=8.7, 4.2 Hz, 4H), 4.07 (t, J=3.9 Hz, 2H), 3.42 (s, 3H), 3.25 (s, 3H), 3.22 (s, 3H), 3.19 (s, 3H), 3.09 (s, 3H), 2.69 (s, 3H), 2.67 (s, 3H), 1.32 (d, J=4.5 Hz, 2H), 1.28 (dd, J=4.2, 1.6 Hz, 4H), 1.10-0.71 (m, 51H); ESI MS m/z 1295 $[C_{68}H_{115}N_{11}O_{13}+H]^+$.

Example 33

Preparation of Cyclosporin Cyclopropyl Alkyne

A solution of the acetate of cyclosporin cyclopropyl alkyne from Example 32 (58 mg, 0.044 mmol) in methanol (3 mL) was stirred at room temperature. Reaction mixture was treated with potassium carbonate (90 mg, 0.65 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo to afford cyclosporin cyclopropyl alkyne (27 mg, 48%) as an off-white solid: $^1$H NMR (300 MHz, CDCl$_3$) δ 7.90 (d, J=9.6 Hz, 1H), 7.65 (d, J=7.3 Hz, 1H), 7.50 (d, J=8.1 Hz, 1H), 7.22 (d, J=7.8 Hz, 1H), 6.03-5.92 (m, 2H), 5.70 (dd, J=10.7, 3.5 Hz, 2H), 5.49 (d, J=5.7 Hz, 2H), 5.38 (s, 1H), 5.33-4.99 (m, 12H), 4.93 (dd, J=9.5, 5.9 Hz, 2H), 4.82 (d, J=5.7 Hz, 2H), 4.76 (s, 2H), 4.71 (s, 2H), 4.65 (t, J=8.9 Hz, 2H), 4.53 (t, J=7.2 Hz, 2H), 3.49 (s, 3H), 3.37 (s, 3H), 3.24 (s, 3H), 3.10 (s, 6H), 2.71 (s, 3H), 2.69 (s, 3H), 1.35 (d, J=7.2 Hz, 2H), 1.26 (d, J=6.6 Hz, 6H), 1.07-0.48 (m, 49H); ESI MS m/z 1253 $[C_{66}H_{113}N_{11}O_{12}+H]^+$; HPLC>99% (AUC), $t_R$=20.26 min.

Example 34

Preparation of the Acetate of Cyclosporin Alkyne

A mixture of acetyl cyclosporin vinyl iodide from Example 3 (100 mg, 0.073 mmol), CuI (7 mg, 0.037 mmol), and PdCl$_2$(PPh$_3$)$_2$ (26 mg, 0.037 mmol) in Et$_3$N (2 mL) was stirred at room temperature under N$_2$ atmosphere. Reaction mixture was then treated with cyclohexylacetylene (80 mg, 0.737 mmol). Reaction was allowed to stir for 6 h at room temperature. Solution was filtered through a short pad of silica gel and then concentrated in vacuo. The crude product was purified by semi-preparative HPLC to afford the acetate of cyclosporin alkyne (75 mg, 76%) as a light brown solid: $^1$H NMR (300 MHz, CDCl$_3$) δ 8.43 (d, J=9.4 Hz, 1H), 8.07 (d, J=6.7 Hz, 1H), 7.85 (d, J=11.7 Hz, 1H), 7.66 (d, J=11.4 Hz, 1H), 6.00-5.90 (m, 1H), 5.80-5.60 (m, 2H), 5.55-5.45 (m, 2H), 5.40-5.20 (m, 3H), 5.10-4.80 (m, 3H), 4.70-4.45 (m, 2H), 3.42 (s, 3H), 3.24 (s, 3H), 3.21 (m, 3H), 3.19 (s, 3H), 3.11 (s, 3H), 2.70 (s, 3H), 2.69 (s, 3H), 2.20-0.80 (m, 83H); ESI MS m/z 1337 [C$_{71}$H$_{121}$N$_{11}$O$_{13}$+H]$^+$.

Example 35

Preparation of Cyclosporin Alkyne

A solution of the acetate of cyclosporin alkyne from Example 34 (76 mg, 0.057 mmol) in methanol (2 mL) was stirred at room temperature. Reaction mixture was treated with potassium carbonate (40 mg, 0.29 mmol) and allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkyne (29 mg, 39%) as a white solid: $^1$H NMR (300 MHz, CDCl$_3$) δ 7.94 (d, J=9.8 Hz, 1H), 7.65-7.55(m, 2H), 7.26 (overlapped with CHCl$_3$, 1H), 6.00-5.85 (m, 1H), 5.71 (dd, J=11.0, 4.0 Hz, 1H), 5.53 (d, J=5.5 Hz, 1H), 5.40 (d, J=15.6 Hz, 1H), 5.30 (dd, J=11.3, 3.5 Hz, 1H), 5.13 (d, J=10.8 Hz, 1H), 5.10-5.00 (m, 3H), 4.89 (dd, J=9.2, 6.2 Hz, 1H), 4.83 (t, J=7.1 Hz, 1H), 4.73 (d, J=14.1 Hz, 1H), 4.63 (t, J=9.7 Hz, 1H), 4.56 (t, J=7.3 Hz, 1H), 3.73 (t, J=7.3 Hz, 1H), 3.50 (s, 3H), 3.38 (s, 3H), 3.25 (s, 3H), 3.11 (s, 3H), 3.09 (s, 3H), 2.71 (s, 3H), 2.70 (s, 3H), 2.60-2.55 (m, 1H), 2.45-2.35 (m, 2H), 2.20-0.75 (m, 74H), 0.68 (d, J=5.8 Hz, 2H); ESI MS m/z 1295 [C$_{69}$H$_{119}$N$_{11}$O$_{12}$+H]$^+$; HPLC 97.9% (AUC), t$_R$=23.24 min.

Example 36

Preparation of Cyclosporin Alkyne

To a stirred solution of trans-acetyl cyclosporin vinyl iodide from Example 3 (50 mg, 0.036 mmol) in triethylamine (3 mL, degassed) were added phenylacetylene (37 mg, 0.36 mmol), copper(I) iodide (7.0 mg, 0.036 mmol) and dichlorobis(triphenylphosphine)palladium(II) (26 mg, 0.036 mmol). After 18 h at room temperature under nitrogen, the mixture was filtered through a 0.2 μm syringe filter and the solvent was removed under reduced pressure. The crude material was purified by semi-preparative HPLC to afford the acetate of cyclosporin alkyne (34 mg, 69%) as a yellowish oil: ESI MS m/z 1331 [C$_{71}$H$_{115}$N$_{11}$O$_{13}$+H]$^+$.

To a stirred solution of the above acetate of cyclosporin alkyne (34 mg, 0.02 mmol) in methanol (3 mL) was added potassium carbonate (30 mg, 0.2 mmol) at room temperature. After 18 h, ethyl acetate (100 mL) and water (50 mL) were added. The organic layer was separated, dried over anhydrous sodium sulfate, and concentrated under vacuum to afford crude product. The material was purified by semi-preparative HPLC to afford cyclosporin alkyne (15 mg, 45%) as a yellowish oil: $^1$H NMR (500 MHz, CDCl$_3$) δ 7.92 (m, 1H), 7.61 (m, 1H), 7.49 (m, 1H), 7.41 (m, 3H), 7.21 (m, 1H), 6.20 (m, 1H), 5.65-4.45 (m, 20H), 3.98 (m, 1H), 3.73 (m, 1H), 3.52 (s, 3H), 3.39 (s, 3H), 3.25 (s, 3H), 3.10 (s, 6H), 2.71 (s, 3H), 2.69 (s, 3H), 2.45-0.70 (m, 62H). ESI MS m/z 1289 [C$_{69}$H$_{113}$N$_{11}$O$_{12}$+H]$^+$; HPLC>98% (AUC); t$_R$=16.67 min.

Example 37

Preparation of the Acetate of Cyclosporin Alkyne

A mixture of acetyl cyclosporin vinyl iodide from Example 3 (80 mg, 0.059 mmol), CuI (6 mg, 0.030 mmol), and PdCl$_2$(PPh$_3$)$_2$ (21 mg, 0.030 mmol) in Et$_3$N (2 mL) was stirred at room temperature under N$_2$ atmosphere. To the above reaction mixture was then treated with 1-chloro-4-ethynylbenzene (80 mg, 0.59 mmol). The resulting reaction mixture was stirred overnight at room temperature. Reaction was filtered through a short pad of silica gel and filtrate was concentrated under reduced pressure. The crude product was purified by semi-preparative HPLC to afford the acetate of cyclosporin alkyne (54 mg, 67%) as a light brown solid: $^1$H NMR (300 MHz, CDCl$_3$) δ 8.47 (d, J=9.6 Hz, 1H), 8.06 (d, J=6.8 Hz, 1H), 7.85-7.65 (m, 2H), 7.61 (d, J=7.6 Hz, 1H), 7.45-7.35 (m, 1H), 7.33-7.27 (m, 2H), 6.05-5.95 (m, 1H), 5.69 (dd, J=11.0, 3.9 Hz, 1H), 5.60-5.47 (m, 2H), 5.45-5.35 (m, 1H), 5.29 (dd, J=8.7, 4.0 Hz, 1H), 5.20-5.10 (m, 1H), 5.05-4.70 (m, 4H), 4.63 (d, J=14.1 Hz, 1H), 4.46 (t, J=7.0 Hz, 1H), 3.44 (s, 3H), 3.27 (s, 3H), 3.26 (s, 3H), 3.20 (s, 3H), 3.09 (s, 3H), 2.69 (s, 3H), 2.68 (s, 3H), 2.50-2.40 (m, 1H), 2.30-0.70 (m, 71H); ESI MS m/z 1365 [C$_{71}$H$_{114}$ClN$_{11}$O$_{13}$+H]$^+$.

Example 38

Preparation of Cyclosporin Alkyne

A solution of the acetate of cyclosporin alkyne from Example 37 (54 mg, 0.047 mmol) in methanol (1.5 mL) was stirred at room temperature. Reaction mixture was treated with potassium carbonate (30 mg, 0.21 mmol) and allowed to keep stirring under N$_2$ atmosphere overnight. Mixture was diluted with ethyl acetate, washed with saturated sodium bicarbonate solution and brine, dried over sodium sulfate, and concentrated under reduced pressure. The crude product was purified by semi-preparative HPLC to afford cyclosporin alkyne (32 mg, 62%) as an off-white solid: $^1$H NMR (500 MHz, CDCl$_3$) δ 7.96 (d, J=9.7 Hz, 1H), 7.65 (d, J=7.4 Hz, 1H), 7.56 (d, J=8.2 Hz, 1H), 7.40-7.33 (m, 2H), 7.30-7.20 (m, 3H), 6.22-6.15 (m 1H), 5.70 (dd, J=1.0, 4.2 Hz, 1H), 5.62 (d, J=15.8 Hz, 1H), 5.52 (d, J=6.2 Hz, 1H), 5.32 (dd, J=11.4, 3.6 Hz, 1H), 5.12-5.00 (m, 2H), 4.96 (dd, J=9.8, 5.9 Hz, 2H), 4.82 (t, J=7.3 Hz, 1H), 4.72 (d, J=14.0 Hz, 1H), 4.67 (t, J=8.9 Hz, 1H), 4.54 (t, J=7.3 Hz, 1H), 3.82 (t, J=6.7 Hz, 1H), 3.52 (s, 3H), 3.40 (s, 3H), 3.26 (s, 3H), 3.11 (s, 3H), 3.10 (s, 3H), 2.71 (s, 3H), 2.69 (s, 3H), 2.65-2.55 (m, 1H), 2.45-2.35 (m, 1H), 2.20-0.85 (m, 65H), 0.75 (d, J=6.9 Hz, 2H); ESI MS m/z 1323 [C$_{69}$H$_{112}$ClN$_{11}$O$_{12}$+H]$^+$; HPLC 97.3% (AUC), t$_R$=22.54 min.

Example 39

Preparation of the Acetate of Cyclosporin Alkyne

A mixture of acetyl cyclosporin vinyl iodide from Example 3 (75 mg, 0.055 mmol), CuI (6 mg, 0.030 mmol), and PdCl$_2$(PPh$_3$)$_2$ (21 mg, 0.030 mmol) in Et$_3$N (2 mL) was stirred at room temperature under N$_2$ atmosphere. Reaction mixture was then treated with 3-ethynylthiophine (65 mg, 0.60 mmol). Reaction was allowed to stir for 6 h at room temperature. Solution was filtered through a short pad of silica gel and then concentrated in vacuo. The crude product was purified by semi-preparative HPLC to afford the acetate of cyclosporin alkyne (31 mg, 42%) as a light brown solid: $^1$H NMR (300 MHz, CDCl$_3$) δ 8.47 (d. J=9.5 Hz, 1H), 8.06 (d, J=6.7 Hz, 1H), 7.73 (d, J=9.2 Hz, 1H), 7.63 (d, J=7.6 Hz, 1H), 7.49 (d, J=2.9 Hz, 1H), 7.25-7.20 (m, 1H), 7.15 (d, J=5.0 Hz, 1H), 6.10-5.90 (m, 1H), 5.70 (dd, J=11.2, 3.5 Hz, 1H), 5.60-4.50 (m, 9H), 4.63 (d, J=14.2 Hz, 1H), 4.51 (t, J=7.2 Hz, 1H), 3.43 (s, 3H), 3.26 (s, 6H), 3.20 (s, 3H), 3.09 (s, 3H), 2.72 (s, 3H), 2.68 (s, 3H), 2.50-2.40 (m, 1H), 2.30-0.70 (m, 71H); ESI MS m/z 1337 $[C_{69}H_{113}N_{11}O_{13}S+H]^+$.

Example 40

Preparation of Cyclosporin Alkyne

A solution of the acetate of cyclosporin alkyne from Example 39 (31 mg, 0.023 mmol) in methanol (2 mL) was stirred at room temperature. Reaction mixture was treated with potassium carbonate (15 mg, 0.108 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkyne (15 mg, 50%) as a white solid; $^1$H NMR (500 MHz, CDCl$_3$) δ 7.94 (d, J=9.8 Hz, 1H), 7.66 (d, J=7.3 Hz, 1H), 7.60 (d, J=8.2 Hz, 1H), 7.50 (dd, J=3.0, 1.0 Hz, 1H), 7.30 (d, J=7.8 Hz, 1H), 7.24 (dd, J=5.0, 3.1 Hz, 1H), 7.11 (dd, J=5.0, 1.1 Hz, 1H), 6.30-6.20 (m, 1H), 5.70 (dd, J=11.0, 4.2 Hz, 1H), 5.61 (d, J=15.8 Hz, 1H), 5.51 (d, J=6.2 Hz, 1H), 5.34 (dd, J=11.3, 3.5 Hz, 1H), 5.15-5.00 (m, 3H), 4.95 (dd, J=9.5, 5.9 Hz, 1H), 4.83 (t, J=7.2 Hz, 1H), 4.73 (d, J=14.1 Hz, 1H), 4.67 (t, J=9.5 Hz, 1H), 4.54 (t, J=7.3 Hz, 1H), 3.83 (t, J=6.9 Hz, 1H), 3.51 (s, 3H), 3.39 (s, 3H), 3.24 (s, 3H), 3.11 (s, 3H), 3.10 (s, 3H), 2.72 (s, 3H), 2.70 (s, 3H), 2.65-2.55 (m, 1H), 2.50-2.40 (m, 1H), 2.20-0.84 (m, 67H); ESI MS m/z 1295 $[C_{67}H_{111}N_{11}O_{12}S+H]^+$; HPLC 97.9% (AUC), $t_R$=20.46 min.

Example 41

Preparation of the Acetate of Cyclosporin Alkyne

A mixture of acetyl cyclosporin vinyl iodide from Example 3 (80 mg, 0.059 mmol), CuI (6 mg, 0.030 mmol), and PdCl$_2$(PPh$_3$)$_2$ (21 mg, 0.030 mmol) in Et$_3$N (2 mL) was stirred at room temperature under $N_2$ atmosphere. Reaction mixture was then treated with 2-ethynylpyridine (61 mg, 0.59 mmol). Reaction was allowed to keep stirring under nitrogen atmosphere at room temperature overnight. The reaction mixture was filtered through a short pad of silica gel and then concentrated in vacuo. The crude product was purified by semi-preparative HPLC to afford the acetate of cyclosporin alkyne (50 mg, 64%) as an off-white solid: $^1$H NMR (300 MHz, CDCl$_3$) δ 8.56 (d, J=4.8 Hz, 1H), 8.52 (d, J=9.7 Hz, 1H), 8.03 (d, J=6.9 Hz, 1H), 7.70-7.60 (m, 2H), 7.50-7.40 (m, 2H), 7.30-7.20 (m, 1H), 6.20-6.10 (m, 1H), 5.68 (dd, J=9.0, 4.0 Hz, 1H), 5.62-5.50 (m, 3H), 5.40-5.25 (m, 2H), 5.20-5.10 (m, 1H), 5.05-4.95 (m, 2H), 4.85-4.75 (m, 1H), 4.64 (d, J=13.8 Hz, 1H), 4.42 (t, J=7.1 Hz, 1H), 3.45 (s, 3H), 3.30 (s, 3H), 3.28 (s, 3H), 3.21 (s, 3H), 3.07 (s, 3H), 2.68 (s, 3H), 2.66 (s, 3H), 2.50-2.40 (m, 2H), 2.30-0.70 (m, 71H); ESI MS m/z 1332 $[C_{70}H_{114}N_{12}O_{13}+H]^+$.

Example 42

Preparation of Cyclosporin Alkyne

A solution of the acetate of cyclosporin alkyne from Example 41 (50 mg, 0.0375 mmol) in methanol (2 mL) was stirred at room temperature. Reaction mixture was treated with potassium carbonate (35 mg, 0.25 mmol) and allowed to keep stirring under $N_2$ atmosphere overnight. Mixture was diluted with ethyl acetate, washed with saturated sodium bicarbonate solution and brine, dried over sodium sulfate, and concentrated under reduced pressure. The crude product was purified by semi-preparative HPL to afford cyclosporin alkyne (3 mg, 6%) as a white solid; $^1$H NMR (500 MHz, CDCl$_3$) δ 8.79 (d, J=4.7 Hz, 1H), 8.00-7.90 (m, 2H), 7.71 (d, J=7.9 Hz, 1H), 7.65 (d, J=7.6 Hz, 1H), 7.50-7.30 (m, 2H), 7.16 (d, J=7.9 Hz, 1H), 6.50-6.40 (m, 1H), 5.75-5.65 (m, 2H), 5.53 (d, J=6.2 Hz, 1H), 5.30-5.25 (m, 1H), 5.15-5.00 (m, 3H), 4.96 (dd, J=9.9, 3.5 Hz, 1H), 4.83 (t, J=7.2 Hz, 1H), 4.72 (d, J=13.9 Hz, 1H), 4.68 (t, J=9.2 Hz, 1H), 4.51 (t, J=7.0 Hz, 1H), 3.84 (t, J=6.8 Hz, 1H), 3.52 (s, 3H), 3.40 (s, 3H), 3.26 (s, 3H), 3.11 (s, 3H), 3.10 (s, 3H) 2.71 (s, 3H), 2.69 (s, 3H), 2.65-2.60 (m, 1H), 2.45-2.40 (m, 1H), 2.20-0.70 (m, 67H); ESI MS m/z 1290 $[C_{68}H_{112}N_{12}O_{12}+H]^+$; HPLC>99% (AUC), $t_R$=18.94 min.

Example 43

Preparation of the Acetate of Cyclosporin Alkyne

A mixture of acetyl cyclosporin vinyl iodide from Example 3 (100 mg, 0.073 mmol), CuI (7 mg, 0.037 mmol), and PdCl$_2$(PPh$_3$)$_2$ (26 mg, 0.037 mmol) in Et$_3$N (2 mL) was stirred at room temperature under $N_2$ atmosphere. Reaction mixture was then treated with 1-pentyne (50 mg, 0.737 mmol). Reaction was allowed to stir for 6 h at room temperature. Solution was filtered through a short pad of silica gel then concentrated in vacuo. The crude product was purified by semi-preparative HPLC to afford the acetate of cyclosporin alkyne (51 mg, 54%) as an off-white solid: $^1$H NMR (300 MHz, CDCl$_3$) δ 8.43 (d, J=9.4 Hz, 1H), 8.06 (d, J=6.7 Hz, 1H), 7.83 (d, J=9.3 Hz, 1H), 7.64 (d, J=7.6 Hz, 1H), 6.00-4.40 (m, 13H), 3.43 (s, 3H), 3.24 (s, 3H), 3.23 (s, 3H), 3.19 (s, 3H), 3.11 (s, 3H), 2.70 (3H), 2.69 (s, 3H), 2.45-0.75 (m, 79H); ESI MS m/z 1297 $[C_{68}H_{117}N_{11}O_{13}+H]^+$.

Example 44

Preparation of Cyclosporin Alkyne

A solution of the acetate of cyclosporin alkyne from Example 43 (51 mg, 0.039 mmol) in methanol (2 mL) was stirred at room temperature. Reaction mixture was treated with potassium carbonate (26 mg, 0.18 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkyne (35 mg, 71%) as a white solid: $^1$H NMR (300 MHz, CDCl$_3$) δ 7.91 (d, J=9.8 Hz, 1H), 7.63 (d, J=7.5 Hz, 1H), 7.48 (d, J=8.2 Hz, 1H), 7.18 (d, J=7.8 Hz, 1H), 6.10-5.95 (m, 1H), 5.71 (dd, J=13.0, 4.1 Hz, 1H), 5.51 (d, J=5.7 Hz, 1H), 5.40 (d, J=15.8 Hz, 1H), 5.30 (dd, J=11.5, 4.0 Hz, 1H), 5.12 (d, J=10.9 Hz, 1H), 5.07-4.95 (m, 2H), 4.92 (dd, J=9.6, 6.0 Hz, 1H), 4.82 (t, J=7.3 Hz, 1H), 4.73 (d, J=14.1 Hz, 1H), 4.64 (t, J=8.3 Hz, 1H), 4.54 (t, J=7.3 Hz, 1H), 3.76 (t, J=6.8 Hz, 1H), 3.51 (s, 3H), 3.38 (s, 3H), 3.25 (s, 3H), 3.09 (s, 6H), 2.71 (s, 3H), 2.69 (s, 3H), 2.65-2.55 (m, 1H), 2.45-2.35 (m, 1H), 2.30-2.20 (m, 2H), 2.15-1.95 (m, 4H), 1.85-0.80 (m, 66H), 0.69 (d, J=6.0 Hz, 2H); ESI MS m/z 1255 $[C_{66}H_{115}N_{11}O_{12}+H]^+$; HPLC>99% (AUC), $t_R$=20.98 min.

Example 45

Preparation of the Acetate of Cyclosporin Alkyne

A mixture of acetyl cyclosporin vinyl iodide from Example 3 (100 mg, 0.073 mmol), CuI (7 mg, 0.037 mmol), and $PdCl_2(PPh_3)_2$ (26 mg, 0.037 mmol) in $Et_3N$ (2 mL) was stirred at room temperature under $N_2$ atmosphere. Reaction mixture was then treated with 1-hexyne (80 mg, 0.737 mmol). Reaction was allowed to stir for 4 h at room temperature. Solution was filtered through a short pad of silica gel and then concentrated in vacuo. The crude product was purified by semi-preparative HPLC to afford the acetate of cyclosporin alkyne (61 mg, 63%) as a light brown solid: $^1$H NMR (300 MHz, $CDCl_3$) δ 8.45 (d, J=9.6 Hz, 1H), 8.05 (d, J=6.8 Hz, 1H), 7.66 (d, J=9.2 Hz, 1H), 7.57 (d, J=7.7 Hz, 1H), 5.90-6.00 (m, 1H), 5.69 (dd, J=10.9, 3.8 Hz, 1H), 5.60-5.10 (m, 5H), 5.05-4.75 (m, 4H), 4.68 (d, J=13.3 Hz, 1H), 3.44 (s, 3H), 3.25 (s, 3H), 3.23 (s, 3H), 3.19 (s, 3H), 3.09 (s, 3H), 2.69 (s, 3H), 2.67 (s, 3H), 2.45-0.75 (m, 82H); ESI MS m/z 1311 $[C_{69}H_{119}N_{11}O_{13}+H]^+$.

Example 46

Preparation of Cyclosporin Alkyne

To a solution of the acetate of cyclosporin alkyne from Example 45 (61 mg, 0.047 mmol) in methanol (2 mL) was added potassium carbonate (30 mg, 0.22 mmol) at room temperature and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkyne (28 mg, 49%) as a white solid: $^1$H NMR (300 MHz, $CDCl_3$) δ 7.91 (d, J=9.7 Hz, 1H), 7.62 (d, J=7.8 Hz, 1H), 7.48 (d, J=8.2 Hz, 1H), 7.18 (d, J=7.9 Hz, 1H), 6.10-5.90 (m, 1H), 5.71 (dd, J=11.0, 3.9 Hz, 1H), 5.51 (d, J=5.7 Hz, 1H), 5.40 (d, J=15.7 Hz, 1H), 5.30 (dd, J=11.5, 3.9 Hz, 1H), 5.12 (d, J=10.9 Hz, 1H), 5.07-4.95 (m, 2H), 4.92 (dd, J=9.6, 6.0 Hz, 1H), 4.80 (t, J=7.4 Hz, 1H), 4.74 (d, J=14.1 Hz, 1H), 4.64 (t, J=8.3 Hz, 1H), 4.54 (t, J=7.3 Hz, 1H), 3.76 (t, J=6.8 Hz, 1H), 3.51 (s, 3H), 3.38 (s, 3H), 3.26 (s, 3H), 3.10 (s, 6H), 2.71 (s, 3H), 2.69 (s, 3H), 2.60-2.50 (m, 1H), 2.45-2.35 (m, 1H), 2.33-2.22 (m, 2H), 2.20-2.00 (m, 4H), 1.85-0.80 (m, 68H), 0.69 (d, J=5.8 Hz, 2H); ESI MS m/z 1269 $[C_{67}H_{117}N_{11}O_{12}+H]^+$; HPLC 98.4% (AUC), $t_R$=21.91 min.

Example 47

Preparation of the Acetate of Cyclosporin Alkyne

A mixture of acetylcyclosporin vinyl iodide from Example 3 (80 mg, 0.059 mmol), CuI (6 mg, 0.030 mmol), and $PdCl_2(PPh_3)_2$ (21 mg, 0.030 mmol) in $Et_3N$ (2 mL) was stirred at room temperature under $N_2$ atmosphere. Reaction mixture was then treated with 5-chloro-1-pentyne (60 mg, 0.59 mmol). Reaction was allowed to stir for 6 h at room temperature. Solution was filtered through a short pad of silica gel and then concentrated in vacuo. The crude product was purified by semi-preparative HPLC to afford the acetate of cyclosporin alkyne (76 mg, 97%) as a light brown solid: $^1$H NMR (300 MHz, $CDCl_3$) δ 8.44 (d, J=9.5 Hz, 1H), 8.05 (d, J=6.8 Hz, 1H), 7.74 (d, J=9.3 Hz, 1H), 7.61 (d, J=7.7 Hz, 1H), 5.95-5.80 (m, 1H), 5.69 (dd, J=11.1, 3.8 Hz, 1H), 5.60-5.45 (m, 3H), 5.35-5.10 (m, 2H), 5.05-4.70 (m, 4H), 4.64 (d, J=14.0 Hz, 1H), 4.46 (t, J=7.1 Hz, 1H), 3.64 (t, J=6.4 Hz, 1H), 3.44 (s, 3H), 3.25 (s, 3H), 3.23 (s, 3H), 3.19 (s, 3H), 3.10 (s, 3H), 2.69 (s, 3H), 2.68 (s, 3H), 2.70-2.60 (m, 2H), 2.25-1.50 (m, 17 h), 1.45-0.60 (m, 58H); m/z 1331 $[C_{68}H_{116}ClN_{11}O_{13}+H]^+$.

Example 48

Preparation of Cyclosporin Alkyne

A solution of the acetate of cyclosporin alkyne from Example 47 (76 mg, 0.047 mmol) in methanol (2 mL) was stirred at room temperature. Reaction mixture was treated with potassium carbonate (35 mg, 0.25 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkyne (29 mg, 49%) as an off-white solid: $^1$H NMR (500 MHz, $CDCl_3$) δ 7.92 (d, J=9.8 Hz, 1H), 7.61 (d, J=7.5 Hz, 1H), 7.49 (d, J=8.2 Hz, 1H), 7.19 (d, J=7.9 Hz, 1H), 6.10-5.95 (m, 1H), 5.70 (dd, J=11.0, 4.3 Hz, 1H), 5.51 (d, J=5.9 Hz, 1H), 5.39 (d, J=16.1 Hz, 1H), 5.29 (dd, J=11.4, 3.8 Hz, 1H), 5.11 (d, J=10.9 Hz, 1H), 5.07-5.00 (m, 2H), 4.92 (dd, J=9.6, 6.0 Hz, 1H), 4.81 (t, J=7.2 Hz, 1H), 4.73 (d, J=14.0 Hz, 1H), 4.64 (dd, J=9.6, 8.6 Hz, 1H), 4.54 (t, J=7.3 Hz, 1H), 3.77 (t, J=7.1 Hz, 1H), 3.64 (t, J=3.4 Hz, 3H), 3.51 (s, 3H), 3.39 (s, 3H), 3.25 (s, 3H), 3.11 (s, 3H), 3.10 (s, 3H), 2.71 (s, 3H), 2.69 (s, 3H), 2.60-2.55 (m, 1H), 2.50-2.40 (m, 3H), 2.20-0.80 (m, 66 h), 0.70 (d, J=6.3 Hz, 2H); m/z 1289 $[C_{66}H_{114}ClN_{11}O_{12}+H]^+$; HPLC 98.1% (AUC), $t_R$=20.39 min.

Example 49

Preparation of the Acetate of Cyclosporin Alkynyl Ether

A solution of the acetate of cyclosporin alkynyl alcohol from Example 20 (77 mg, 0.06 mmol) in methylene chloride (2 mL) was stirred at room temperature under $N_2$ atmosphere. Solution was treated with allyl chloride (46 mg, 0.60 mmol), $PhCH_2NEt_3Cl$ (14 mg, 0.06 mmol) and 40% KOH in water (2 mL). The reaction was stirred for 6 h. Mixture was diluted with ether and washed with water and brine, dried over sodium sulfate, and concentrated in vacuo. The crude product was purified by semi-preparative HPLC to afford the acetate of cyclosporin alkynyl ether (18 mg, 23%) as an off-white solid: $^1$H NMR (300 MHz, $CDCl_3$) δ 8.43 (d, J=9.6 Hz, 1H), 8.01 (d, J=6.6 Hz, 1H), 7.61 (d, J=9.1 Hz, 1H), 7.55 (d, J=7.7 Hz, 1H), 5.98-5.86 (m, 4H), 5.52 (d, J=9.8 Hz, 2H), 5.38-4.62 (m, 17H), 4.45 (d, J=6.8 Hz, 1H), 4.41 (d, J=1.2 Hz, 2H), 4.26 (s, 2H), 4.13 (d, J=2.1 Hz, 2H), 4.06 (d, J=5.5 Hz, 2H), 3.43 (s, 3H), 3.25 (s, 3H), 3.23 (s, 3H), 3.19 (s, 3H), 3.09 (s, 3H), 2.68 (s, 3H), 2.66 (s, 3H), 1.54 (d, J=10.2 Hz, 2H), 1.46 (s, 2H), 1.37 (s, 2H), 1.38-1.19 (m, 4H), 1.06-0.84 (m, 48H), 0.80 (d, J=6.5 Hz, 2H); ESI MS m/z 1325 $[C_{69}H_{117}N_{11}O_{14}+H]^+$.

Example 50

Preparation of Cyclosporin Alkynyl Ether

A solution of the acetate of cyclosporin alkynyl ether from Example 49 (14.5 mg, 0.01 mmol) in methanol (2 mL) was stirred at room temperature. Reaction mixture was treated with potassium carbonate (25 mg, 0.18 mmol) and was allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl ether (6 mg, 42%) as a white solid: $^1$H NMR (300 MHz, CDCl$_3$) δ 7.94 (d, J=9.6 Hz, 1H), 7.62 (d, J=7.6 Hz, 1H), 7.44 (d, J=8.4 Hz, 1H), 7.14 (d, J=7.9 Hz, 1H), 6.12-5.68 (m, 2H), 5.51 (d, J=5.7 Hz, 2H), 5.47 (s, 1H), 5.42 (s, 1H), 5.35-5.28 (m, 1H), 5.22 (d, J=1.3 Hz, 2H), 5.19 (d, J=1.2 Hz, 2H), 5.12 (s, 2H), 5.08 (s, 2H), 5.07-4.81 (m, 2H), 4.75 (s, 1H), 4.70 (s, 1H), 4.26 (d, J=1.7 Hz, 3H), 4.13 (s, 2H), 4.12-4.04 (m, 2H), 3.51 (s, 3H), 3.39 (s, 3H), 3.26 (s, 3H), 3.11 (s, 3H), 3.10 (s, 3H), 2.70 (s, 3H), 2.68 (s, 3H), 2.13 (s, 2H), 2.04 (s, 3H), 1.53 (d, J=6.9 Hz, 1H), 1.45 (s, 2H), 1.37 (s, 2H), 1.34 (d, J=10.8 Hz, 2H), 1.25 (s, 2H), 1.09-0.81 (m, 48H), 0.71 (d, J=6.1 Hz, 2H); ESI MS m/z 1283 [C$_{67}$H$_{115}$N$_{11}$O$_{13}$+H]$^+$; HPLC 95.1% (AUC), t$_R$=19.71 min.

Example 51

Preparation of the Acetate of Cyclosporin Alkynyl Ether

A mixture of acetyl cyclosporin vinyl iodide from Example 3 (70 mg, 0.051 mmol), CuI (5 mg, 0.026 mmol) and PdCl$_2$(PPh$_3$)$_2$ (18 mg, 0.026 mmol) in Et$_3$N (3 mL) was stirred at room temperature under $N_2$ atmosphere. Reaction mixture was then treated with methyl propargyl ether (36 mg, 0.51 mmol). Reaction was allowed to stir for 4 h at room temperature. Solution was filtered through micro-filter and then concentrated in vacuo. The crude product was purified by semi-preparative HPLC to afford the acetate of cyclosporin alkynyl ether (61 mg, 91%) as an off-white solid: $^1$H NMR (300 MHz, CDCl$_3$) δ 8.39 (d, J=9.4 Hz, 1H), 8.02 (d, J=6.5 Hz, 1H), 7.70 (d, J=9.1 Hz, 1H), 7.69 (d, J=8.6 Hz, 1H), 6.04-5.91 (m, 4H), 5.52 (d, J=11.1 Hz, 2H), 5.39-5.14 (m, 8H), 5.06-4.61 (m, 12H), 4.45 (t, J=7.0 Hz, 2H), 4.21 (d, J=1.5 Hz, 2H), 3.40 (s, 3H), 3.28 (s, 3H), 3.22 (s, 3H), 3.19 (s, 3H), 3.09 (s, 3H), 2.69 (s, 3H), 2.67 (s, 3H), 2.01 (s, 2H), 1.44-1.25 (m, 8H), 1.06-0.74 (m, 50H); ESI MS m/z 1299 [C$_{67}$H$_{115}$N$_{11}$O$_{14}$+H]$^+$.

Example 52

Preparation of Cyclosporin Alkynyl Ether

A solution of the acetate of cyclosporin alkynyl ether from Example 51 (61 mg, 0.047 mmol) in methanol (2 mL) was stirred at room temperature. Reaction mixture was treated with potassium carbonate (80 mg, 0.58 mmol) and was allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl ether (31 mg, 52%) as a white solid: $^1$H NMR (300 MHz, CDCl$_3$) δ 7.93 (d, J=9.4 Hz, 1H), 7.63 (d, J=7.4 Hz, 1H), 7.47 (d, J=8.1 Hz, 1H), 7.18 (d, J=8.0 Hz, 1H), 6.19-6.08 (m, 2H), 5.70 (dd, J=11.0, 3.9 Hz, 1H), 5.50 (d, J=5.9 Hz, 1H), 5.45 (d, J=15.8 Hz, 1H), 5.33-5.27 (m, 2H), 5.12 (s, 2H), 5.09-5.01 (m, 1H), 4.93 (dd, J=9.8, 5.8 Hz, 1H), 4.82 (t, J=7.4 Hz, 2H), 4.76-4.61 (m, 2H), 4.53 (t, J=7.2 Hz, 2H), 4.26 (d, J=1.7 Hz, 1H), 4.20 (d, J=1.7 Hz, 3H), 3.78 (t, J=6.2 Hz, 2H), 3.51 (s, 3H), 3.39 (s, 6H), 3.38 (s, 3H), 3.25 (s, 3H), 3.11 (s, 3H), 3.10 (s, 3H), 2.70 (d, J=6.0 Hz, 6H), 1.54 (d, J=9.7 Hz, 2H), 1.46 (s, 1H), 1.36-1.24 (m, 6H), 1.08-0.82 (m, 48H), 0.70 (d, J=6.2 Hz, 2H); ESI MS m/z 1257 [C$_6$H$_{113}$N$_{11}$O$_{13}$+H]$^+$; HPLC>99% (AUC), t$_R$=18.99 min.

Example 53

Preparation of the Acetate of Cyclosporin Alkynyl Sulfide

A mixture of acetyl cyclosporin vinyl iodide from Example 3 (70 mg, 0.051 mmol), CuI (5 mg, 0.026 mmol), and PdCl$_2$(PPh$_3$)$_2$ (18 mg, 0.026 mmol) in Et$_3$N (3 mL) was stirred at room temperature under $N_2$ atmosphere. Reaction mixture was then treated with propargyl ethyl sulfide (52 mg, 0.51 mmol). Reaction was allowed to stir overnight at room temperature. Solution was filtered through micro-filter and then concentrated in vacuo. The crude product was purified by semi-preparative HPLC to afford the acetate of cyclosporin alkynyl sulfide (59 mg, 87%) as an off-white solid: $^1$H NMR (300 MHz, CDCl$_3$) δ 8.43 (d, J=8.6 Hz, 1H), 8.03 (d, J=6.4 Hz, 1H), 7.65 (d, J=8.9 Hz, 1H), 7.57 (d, J=7.9 Hz, 1H), 5.98-5.67 (m, 4H), 5.51 (d, J=10.8 Hz, 2H), 5.36-4.76 (m, 16H), 4.63 (d, J=14.2 Hz, 2H), 4.46 (t, J=7.0 Hz, 2H), 3.98 (s, 2H), 3.43 (s, 3H), 3.25 (s, 3H), 3.22 (s, 3H), 3.19 (s, 3H), 3.15 (s, 3H), 2.68 (s, 3H), 2.67 (s, 3H), 2.01 (s, 2H), 1.34-1.25 (m, 8H), 1.04 (d, J=6.6 Hz, 4H), 1.01-0.79 (m, 50H); ESI MS m/z 1329 [C$_{68}$H$_{117}$N$_{11}$O$_{13}$S+H]$^+$.

Example 54

Preparation of Cyclosporin Alkynyl Sulfide

A solution of the acetate of cyclosporin alkynyl sulfide from Example 53 (59 mg, 0.044 mmol) in methanol (2 mL) was stirred at room temperature. Reaction mixture was treated with potassium carbonate (70 mg, 0.51 mmol) and was allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl sulfide (25 mg, 45%) as a white solid: $^1$H NMR (300 MHz, CDCl$_3$) δ 7.92 (d, J=9.6 Hz, 1H), 7.63 (d, J=7.5 Hz, 1H), 7.46 (d, J=8.4 Hz, 1H), 7.16 (d, J=8.0 Hz, 1H), 6.11-6.02 (m, 2H), 5.70 (dd, J=11.4, 3.9 Hz, 1H), 5.51 (d, J=5.7 Hz, 2H), 5.46-4.91 (m, 16H), 4.82 (t, J=7.5 Hz, 2H), 4.75 (s, 1H), 4.72-4.61 (m, 4H), 4.53 (t, J=7.2 Hz, 2H), 4.26 (d J=1.7 Hz, 1H), 4.13 (s, 1H), 3.76 (t, J=7.1 Hz, 2H), 3.51 (s, 3H), 3.38 (s, 3H), 3.25 (s, 3H), 3.10 (s, 3H), 3.09 (s, 3H), 2.71 (s, 3H), 2.69 (s, 3H), 1.54 (d, J=9.6 Hz, 1H), 1.45-1.24 (m, 6H), 1.08-0.82 (m, 48H), 0.69 (d, J=6.0 Hz, 1H); ESI MS m/z 1287 [C$_{66}$H$_{115}$N$_{11}$O$_{12}$+H]$^+$; HPLC 93.1% (AUC), t$_R$=20.29 min.

Example 55

Preparation of the Acetate of Cyclosporin Alkynyl Ether

A mixture of acetyl cyclosporin vinyl iodide from Example 3 (70 mg, 0.051 mmol), CuI (5 mg, 0.026 mmol), and PdCl$_2$(PPh$_3$)$_2$ (18 mg, 0.026 mmol) in Et$_3$N (3 mL) was stirred at room temperature under $N_2$ atmosphere. Reaction mixture was then treated with propargyl ether (53 μL, 0.51 mmol). Reaction was allowed to stir overnight at room temperature. Solution was filtered through micro-filter and then concentrated in vacuo. The crude product was purified by semi-preparative HPLC to afford the acetate of cyclosporin alkynyl ether (28 mg, 41%) as an off-white solid: $^1$H NMR (300 MHz, CDCl$_3$) δ 8.47 (d, J=9.6 Hz, 1H), 8.01 (d, J=6.8 Hz, 1H), 7.51 (d, J=7.1 Hz, 2H), 5.68 (dd, J=10.8, 3.6 Hz, 1H), 5.52 (d, J=8.9 Hz, 2H), 5.38-4.74 (m, 18H), 4.64 (d, J=13.8 Hz, 2H), 4.37 (d, J=1.5 Hz, 3H), 4.25 (d, J=3.6 Hz, 3H), 4.22 (d, J=3.6 Hz, 1H), 3.44 (s, 3H), 3.26 (s, 3H), 3.24 (s, 3H), 3.20 (s, 3H), 3.08 (s, 3H), 2.67 (s, 3H), 2.65 (s, 3H), 2.01 (s, 2H), 1.31 (d, J=7.1 Hz, 4H), 1.27 (d, J=7.3 Hz, 4H), 1.06-0.84 (m, 48H), 0.80 (d, J=6.6 Hz, 2H); ESI MS m/z 1323 [C$_{69}$H$_{115}$N$_{11}$O$_{14}$+H]$^+$.

Example 56

Preparation of Cyclosporin Alkynyl Ether

A solution of the acetate of cyclosporin alkynyl ether from Example 55 (28 mg, 0.021 mmol) in methanol (2 mL) was stirred at room temperature. Reaction mixture was treated with potassium carbonate (35 mg, 0.25 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl ether (14 mg, 53%) as a white solid: $^1$H NMR (300 MHz, CDCl$_3$) δ 7.94 (d, J=9.6 Hz, 1H), 7.63 (d, J=7.5 Hz, 1H), 7.45 (d, J=8.2 Hz, 1H), 7.16 (d, J=7.9 Hz, 1H), 6.18-6.09 (m, 2H), 5.70 (dd, J=11.2, 4.1 Hz, 1H), 5.50 (d, J=5.9 Hz, 1H), 5.44 (d, J=15.9 Hz, 1H), 5.29 (dd, J=11.3, 4.3 Hz, 2H), 5.12-4.61 (m, 18H), 4.53 (d, J=7.3 Hz, 1H), 4.37 (d, J=1.7 Hz, 3H), 4.26 (d, J=2.4 Hz, 3H), 3.79 (d, J=6.5 Hz, 1H), 3.58 (s, 3H), 3.51 (s, 3H), 3.26 (s, 3H), 3.11 (s, 3H), 3.10 (s, 3H), 2.70 (s, 3H), 2.68 (s, 3H), 2.43 (t, J=2.9 Hz, 2H), 1.34 (d, J=7.2 Hz, 2H), 1.25 (d, J=6.7 Hz, 2H), 1.08-0.82 (m, 48H), 0.71 (d, J=6.2 Hz, 1H); ESI MS m/z 1281 [C$_{67}$H$_{113}$N$_{11}$O$_{13}$+H]$^+$; HPLC>99% (AUC), t$_R$=18.88 min.

Example 57

Preparation of the Acetate of Cyclosporin Alkynyl Ether

A mixture of acetyl cyclosporin vinyl iodide from Example 3 (70 mg, 0.051 mmol), CuI (5 mg, 0.026 mmol), and PdCl$_2$(PPh$_3$)$_2$ (18 mg, 0.026 mmol) in Et$_3$N (3 mL) was stirred at room temperature under N$_2$ atmosphere. Reaction mixture was then treated with phenyl propargyl ether (68 mg, 0.51 mmol). Reaction was allowed to stir overnight at room temperature. Solution was filtered through micro-filter and then concentrated in vacuo. The crude product was purified by semi-preparative HPLC to afford the acetate of cyclosporin alkynyl ether (67 mg, 96%) as an off-white solid: $^1$H NMR (300 MHz, CDCl$_3$) δ 8.40 (d, J=8.9 Hz, 1H), 8.02 (d, J=6.6 Hz, 1H), 7.74 (d, J=8.7 Hz, 1H), 7.59 (d, J=5.5 Hz, 1H), 7.01-6.84 (m, 3H), 6.01-5.59 (m, 4H), 5.54-5.05 (m, 14H), 4.97 (d, J=10.7 Hz, 2H), 4.81 (d, J=7.7 Hz, 2H), 4.46 (d, J=6.8 Hz, 2H), 3.44 (s, 3H), 3.24 (s, 3H), 3.20 (s, 3H), 3.19 (s, 3H), 3.12 (s, 3H), 2.69 (s, 3H), 2.67 (s, 3H), 2.07 (s, 1H), 2.02 (s, 2H), 1.93 (s, 2H), 1.34 (d, J=7.2 Hz, 4H), 1.32-1.24 (m, 6H), 1.04 (d, J=6.3 Hz, 2H), 1.01-0.73 (m, 48H); ESI MS m/z 1361 [C$_{72}$H$_{117}$N$_{11}$O$_{14}$+H]$^+$.

Example 58

Preparation of Cyclosporin Alkynyl Ether

A solution of the acetate of cyclosporin alkynyl ether from Example 57 (67 mg, 0.049 mmol) in methanol (2 mL) was stirred at room temperature. Reaction mixture was treated with potassium carbonate (35 mg, 0.58 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl ether (36 mg, 55%) as a white solid: $^1$H NMR (300 MHz, CDCl$_3$) δ 7.90 (d, J=9.5 Hz, 1H), 7.61 (d, J=7.2 Hz, 1H), 7.43 (d, J=7.8 Hz, 1H), 7.16 (d, J=7.6 Hz, 1H), 6.98 (d, J=7.3 Hz, 2H), 6.20-6.10 (m, 2H), 5.70 (dd, J=10.9, 3.7 Hz, 1H), 5.49 (d, J=5.9 Hz, 1H), 5.44 (d, J=16.1 Hz, 1H), 5.32-4.63 (m, 25H), 4.52 (t, J=7.2 Hz, 2H), 3.50 (s, 3H), 3.38 (s, 3H), 3.25 (s, 3H), 3.10 (s, 6H), 2.70 (s, 3H), 2.68 (s, 3H), 1.40 (d, J=5.7 Hz, 2H), 1.36-0.80 (m, 52H), 0.70 (d, J=6.3 Hz, 2H); ESI MS m/z 1319 [C$_{70}$H$_{115}$N$_{11}$O$_{13}$+H]$^+$; HPLC 94.2% (AUC), t$_R$=20.37 min.

Example 59

Preparation of the Acetate of Cyclosporin Alkynyl Ester

A mixture of acetyl cyclosporin vinyl iodide from Example 3 (70 mg, 0.051 mmol), CuI (5 mg, 0.026 mmol), and PdCl$_2$(PPh$_3$)$_2$ (18 mg, 0.026 mmol) in Et$_3$N (3 mL) was stirred at room temperature under N$_2$ atmosphere. Reaction mixture was then treated with t-butyl (2-propynyloxy)acetate (50 µL, 0.51 mmol). Reaction was allowed to stir for 6 h at room temperature. Solution was filtered through micro-filter and then concentrated in vacuo. The crude product was purified by semi-preparative HPLC to afford the acetate of cyclosporin alkynyl ester (71 mg, 98%) as an off-white solid: $^1$H NMR (300 MHz, CDCl$_3$) δ 8.45 (d, J=9.3 Hz, 1H), 8.03 (d, J=6.7 Hz, 1H), 7.70 (d, J=9.0 Hz, 1H), 7.59 (d, J=8.0 Hz, 1H), 6.02-5.56 (m, 5H), 5.52 (d, J=11.2 Hz, 2H), 5.38-4.70 (m, 12H), 4.63 (d, J=14.0 Hz, 2H), 4.45 (t, J=7.0 Hz, 2H), 4.39 (d, J=1.7 Hz, 3H), 4.07 (s, 2H), 3.98 (s, 2H), 3.53 (s, 3H), 3.43 (s, 3H), 3.25 (s, 3H), 3.22 (s, 3H), 3.19 (s, 3H), 3.09 (s, 3H), 2.68 (s, 3H), 2.67 (s, 3H), 2.01 (s, 3H), 1.48 (s, 4H), 1.43-0.20 (m, 8H), 1.05-0.79 (m, 50H); ESI MS m/z 1399 [C$_{72}$H$_{123}$N$_{11}$O$_{16}$+H]$^+$.

Example 60

Preparation of Cyclosporin Alkynyl Ester

A solution of the acetate of cyclosporin alkynyl ester from Example 59 (71 mg, 0.05 mmol) in methanol (2 mL) was stirred at room temperature. Reaction mixture was treated with potassium carbonate (85 mg, 0.62 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl acid (28 mg, 41%) as a white solid: $^1$H NMR (300 MHz, CDCl$_3$) δ 7.93 (d, J=10.2 Hz, 1H), 7.59 (d, J=8.7 Hz, 1H), 7.48 (d, J=8.6 Hz, 1H), 7.28 (hidden by solvent peak, 1H), 6.24-6.10 (m, 2H), 5.90-5.66 (m, 2H), 5.45 (d, J=7.2 Hz, 2H), 5.41 (s, 2H), 5.18-4.97 (m, 7H), 4.83 (t, J=7.0 Hz, 1H), 4.74-4.66 (m, 2H), 5.52-4.39 (m, 6H), 4.35 (s, 2H), 4.26 (d, J=1.7 Hz, 1H), 4.19 (s, 3H), 4.14 (d, J=2.0 Hz, 1H), 3.89 (t, J=6.6 Hz, 1H), 3.48 (s, 3H), 3.38 (s, 3H), 3.23 (s, 3H), 3.11 (s, 3H), 3.10 (s, 3H), 2.69 (s, 6H), 1.54 (d, J=9.6 Hz, 1H), 1.46 (s, 1H), 1.38-1.25 (m, 5H), 1.06-0.74 (m, 49H); ESI MS m/z 1301 [C$_{66}$H$_{113}$N$_{11}$O$_{15}$+H]$^+$; HPLC>99% (AUC), t$_R$=17.09 min.

Example 61

Preparation of the Acetate of Cyclosporin Alkynyl Acid

A mixture of acetyl cyclosporin vinyl iodide from Example 3 (70 mg, 0.051 mmol), CuI (5 mg, 0.026 mmol), and PdCl$_2$(PPh$_3$)$_2$ (18 mg, 0.026 mmol) in Et$_3$N (3 mL) was stirred at room temperature under N$_2$ atmosphere. Reaction mixture was then treated with 4-pentynoic acid (51 mg, 0.51 mmol). Reaction was allowed to stir for 4 h at room temperature. Solution was filtered through micro-filter and then concentrated in vacuo. The crude product was purified by semi-preparative HPLC to afford the acetate of cyclosporin alkynyl acid (23 mg, 34%) as an off-white solid: $^1$H NMR (300 MHz, CDCl$_3$) δ 8.62 (d, J=7.7 Hz, 1H), 8.41 (d, J=9.4 Hz, 1H), 7.97 (d, J=6.8 Hz, 1H), 7.68 (d, J=7.2 Hz, 1H), 5.68 (dd, J=11.1, 3.8 Hz, 2H), 5.59 (d, J=7.6 Hz, 2H), 5.55 (s, 1H), 5.50 (d, J=6.5 Hz, 2H), 5.46-4.77 (m, 13H), 4.63 (d, J=13.4 Hz, 2H), 4.49 (t, J=7.3 Hz, 1H), 4.42 (t, J=6.9 Hz, 2H), 3.44 (s, 3H), 3.35 (s, 3H), 3.25 (s, 3H), 3.20 (s, 3H), 3.12 (s, 3H), 3.08 (s, 3H), 2.67 (s, 3H), 2.65 (s, 3H), 2.01 (s, 2H), 1.36-1.18 (m, 10H), 1.06-0.78 (m, 50H); ESI MS m/z 1327 [C$_{68}$H$_{115}$N$_{11}$O$_{15}$+H]$^+$.

Example 62

Preparation of Cyclosporin Alkynyl Acid

A solution of the acetate of cyclosporin alkynyl acid from Example 61 (23 mg, 0.017 mmol) in methanol (2 mL) was stirred at room temperature. Reaction mixture was treated with potassium carbonate (30 mg, 0.22 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl acid (11 mg, 50%) as a white solid: $^1$H NMR (300 MHz, CDCl$_3$) δ 7.94 (d, J=9.4 Hz, 1H), 7.57 (d, J=7.2 Hz, 1H), 7.48 (d, J=8.4 Hz, 1H), 7.28 (hidden by solvent peak, 1H), 6.03-5.66 (m, 3H), 5.46 (d, J=6.1 Hz, 2H), 5.38 (d, J=16.0 Hz, 1H), 5.31 (d, J=8.8 Hz, 1H), 5.10 (d, J=10.8 Hz, 2H), 5.06-4.67 (m, 17H), 4.49 (t, J=7.1 Hz, 2H), 3.81 (t, J=6.5 Hz, 2H), 3.48 (s, 3H), 3.38 (s, 3H), 3.24 (s, 3H), 3.10 (s, 3H), 3.09 (s, 3H), 2.69 (s, 6H), 2.60 (s, 3H), 1.35 (d, J=7.2 Hz, 2H), 1.26 (d, J=6.4 Hz, 2H), 1.07-0.79 (m, 49H), 0.70 (d, J=6.4 Hz, 2H); ESI MS m/z 1285 [C$_{66}$H$_{113}$N$_{11}$O$_{14}$+H]$^+$; HPLC>99% (AUC), t$_R$=17.39 min.

Example 63

Preparation of Cyclosporin Alkynyl Acid

Cyclosporin alkynyl aldehyde from Example 22 (28 mg, 0.02 mmol) was dissolved in acetonitrile (1 mL) and stirred at room temperature under N$_2$ atmosphere. Reaction was treated with 40% NaH$_2$PO$_4$ solution in water (1 mL). Next the mixture was treated with NaClO$_2$ (3 mg, 0.03 mmol) and H$_2$O$_2$ (35% in water, 3 μL, 0.03 mmol). Reaction mixture was stirred for 1 h. Reaction was quenched with sodium sulfite (100 mg). Mixture was diluted with ethyl acetate and washed with 1 N HCl. Organic layer washed with water and brine, dried over sodium sulfate, and concentrated in vacuo. The crude product (28 mg, 100%) was carried forward without purification. A solution of the crude product (28 mg, 0.021 mmol) in methanol (1.5 mL) was stirred at room temperature. Reaction mixture was treated with potassium carbonate (100 mg, 0.72 mmol) and was allowed to keep stirring under N$_2$ atmosphere for 4 h. Mixture was diluted with ethyl acetate, washed with saturated sodium bicarbonate solution and brine, dried over sodium sulfate, and concentrated in vacuo. The crude product was purified by semi-preparative HPLC to afford cyclosporin alkynyl acid (3.5 mg, 13%) as a white solid: $^1$H NMR (300 MHz, CDCl$_3$) δ 7.89 (d, J=8.1 Hz, 1H), 7.65 (br s, 1H), 7.39 (br s, 1H), 7.30 (d, J=7.6 Hz, 1H), 6.33-6.22 (m, 2H), 5.69 (d, J=10.7 Hz, 2H), 5.60 (d, J=16.0 Hz, 1H), 5.34 (d, J=6.8 Hz, 2H), 5.12-4.64 (m, 15H), 4.46 (t, J=7.0 Hz, 2H), 4.08 (d, J=6.8 Hz, 2H), 3.50 (s, 3H), 3.39 (s, 3H), 3.23 (s, 3H), 3.15 (s, 3H), 3.09 (s, 3H), 2.69 (s, 3H), 2.68 (s, 3H), 1.38 (d, J=7.3 Hz, 3H), 1.32 (d, J=7.3 Hz, 3H), 1.27-0.81 (m, 52H); ESI MS m/z 1257 [C$_{64}$H$_{109}$N$_{11}$O$_{14}$+H]$^+$; HPLC 83.4% (AUC), t$_R$=17.48 min.

Example 64

Preparation of the Acetate of Cis-Cyclosporin Vinyl Iodide

To a vigorously stirred suspension of (iodomethyl)triphenylphosphonium iodide (1.3 g, 2.4 mmol) in dry THF (18 mL) under nitrogen, was added sodium bis(trimethylsilyl)amide (2.4 mL, 1 M in THF, 2.4 mmol). After 10 min at room temperature, the mixture was cooled to 0° C. and acetyl cyclosporin aldehyde from Example 2 (300 mg, 0.240 mmol) in anhydrous THF (10 mL) was added dropwise. After 10 min at 0° C., the reaction was quenched with a saturated solution of ammonium chloride (10 mL), and then allowed to warm to room temperature. The resulting solid was filtered off through a plug of diatomaceous earth and washed with ethyl acetate (200 mL). The organic layer was washed with an aqueous solution of sodium hydrogensulfite (20%, 200 mL), then dried over anhydrous sodium sulfate and concentrated under vacuum to afford crude product (540 mg). The material was purified by semi-preparative HPLC to afford the acetate of the cis-isomer of cyclosporin vinyl iodide (150 mg, 46%) as a pale-brown oil: $^1$H NMR (300 MHz, CDCl$_3$) δ 8.53 (d, J=9.8 Hz, 1H), 8.15 (d, J=6.5 Hz, 1H), 7.82 (d, J=9.0 Hz, 1H), 7.63 (d, J=8.2 Hz, 1H), 6.10 (d, J=7.4 Hz, 1H), 6.02-5.94 (m, 1H), 5.69 (dd, J=10.9, 3.8 Hz, 1H), 5.61-5.48 (m, 2H), 5.38-5.13 (m, 3H), 4.98 (d, J=10.9 Hz, 2H), 4.87 (t, J=7.4 Hz, 1H), 4.78 (t, J=9.6 Hz, 1H), 4.63 (d, J=14.2 Hz, 1H), 4.47 (t, J=7.0 Hz, 1H), 3.98 (s, 3H), 3.43 (s, 3H), 3.27 (s, 3H), 3.21 (s, 3H), 3.19 (s, 3H), 3.14 (s, 3H), 2.69 (s, 3H), 2.42-2.30 (m, 1H), 2.22-1.85 (m, 8H), 2.06 (s, 3H), 1.77-1.60 (m, 3H), 1.54-0.75 (m, 56H); ESI MS m/z 1357 [C$_{63}$H$_{110}$IN$_{11}$O$_{13}$+H]$^+$.

Example 65

Preparation of the Acetate of Cis-Cyclosporin Alkyne

A mixture of the acetate of cis-cyclosporin vinyl iodide from Example 64 (100 mg, 0.073 mmol), CuI (7 mg, 0.037 mmol), and PdCl$_2$(PPh$_3$)$_2$ (26 mg, 0.037 mmol) in Et$_3$N (3 mL) was stirred at room temperature under N$_2$ atmosphere. Reaction mixture was then treated with (trimethylsilyl)acetylene (72 mg, 0.737 mmol). Reaction was stirred overnight at room temperature. Solution was filtered through a short pad of silica gel and then filtrate was concentrated under reduced pressure. The crude product was purified by semi-preparative HPLC to afford the acetate of cis-cyclosporin alkyne (27 mg, 28%) as an off-white solid: $^1$H NMR (300 MHz, CDCl$_3$) δ 8.40 (d, J=9.7 Hz, 1H), 7.86 (d, J=6.0 Hz, 1H), 7.59 (d, J=9.1

Hz, 1H), 7.37 (d, J=7.6 Hz, 1H), 5.60-5.40 (m, 4H), 5.23 (d, J=11.3 Hz, 1H), 5.15-4.95 (m, 3H), 4.85-4.75 (m, 1H), 4.68 (t, J=7.0 Hz, 1H), 4.64 (t, J=9.5 Hz, 1H), 4.48 (d, J=13.9 Hz, 1H), 4.28 (t, J=7.0 Hz, 1H), 3.27 (s, 3H), 3.10 (s, 3H), 3.06 (s, 3H), 3.01 (s, 3H), 2.95 (s, 3H), 2.52 (s, 3H), 2.51 (s, 3H), 2.30-0.60 (m, 72H), 0.01 (s, 9H); ESI MS m/z 1327 $[C_{68}H_{119}N_{11}O_{13}Si+H]$.

Example 66

Preparation of Cis-Cyclosporin Alkyne

A solution of acetate of cis-cyclosporin alkyne from Example 65 (27 mg, 0.020 mmol) in methanol (2 mL) was stirred at room temperature. Reaction mixture was treated with potassium carbonate (12 mg, 0.087 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cis-cyclosporin alkyne (12 mg, 48%) as a white solid: $^1$H NMR (300 MHz, $CDCl_3$) δ 8.03 (d, J=9.7 Hz, 1H), 7.64 (d, J=7.2 Hz, 1H), 7.48 (d, J=8.4 Hz, 1H), 7.25 (d, J=7.8 Hz, 1H), 6.10-5.95 (m, 1H), 5.68 (dd, J=11.2, 4.2 Hz, 1H), 5.60-5.50 (m, 1H), 5.45-5.40 (m, 2H), 5.35-5.25 (m, 2H), 5.13-4.95 (m, 2H), 4.85 (t, J=6.9 Hz, 1H), 4.75-4.60 (m, 2H), 4.50 (t, J=7.3 Hz, 1H), 3.93 (t, J=6.7 Hz, 1H), 3.52 (s, 3H), 3.40 (s, 3H), 3.24 (s, 3H), 3.12 (s, 3H), 3.11 (s, 3H), 2.69 (s, 6H), 2.50-2.40 (m, 2H), 2.20-0.8 (m, 68H); ESI MS m/z 1213 $[C_{63}H_{109}N_{11}O_{12}+H]^+$; HPLC>99% (AUC), $t_R$=18.94 min.

Example 67

Preparation of the Acetate of Cis-Cyclosporin Alkyne

To a solution of 1-propynlmagnesium bromide (0.5 M solution in THF, 1.01 mL, 0.55 mmol) in THF (2 mL) was added $ZnCl_2$ (1.0 M solution in ether, 0.55 mL, 0.55 mmol) dropwise at 0° C. The resulting solution was stirred for 5 min at 0° C. Then ice-bath was removed and reaction mixture was allowed to warm to room temperature. A solution of the acetate of cis-cyclosporin vinyl iodide from Example 64 (75 mg. 0.055 mmol) in THF (1 mL) was added followed by the addition of $PdCl_2(PPh_3)_2$ (19 mg, 0.027 mmol) and the reaction mixture was stirred at room temperature under argon atmosphere overnight. Reaction mixture was concentrated under reduced pressure, diluted with ethyl acetate and filtered through a short pad of silica gel, the filtrate was then concentrated under reduced pressure. The crude product was purified by semi-preparative HPLC to afford the acetate of cis-cyclosporin alkyne (47 mg, 67%) as a brown solid: $^1$H NMR (500 MHz, $CDCl_3$) δ 8.56 (d, J=9.7 Hz, 1H), 8.02 (d, J=6.8 Hz, 1H), 7.65 (d, J=9.2 Hz, 1H), 7.52 (d, J=7.7 Hz, 1H), 5.70-5.50 (m, 4H), 5.30-5.10 (m, 3H), 5.00-4.90 (m, 2H), 4.85 (t, J=7.3 Hz, 1H), 4.76 (t, J=9.6 Hz, 1H), 4.63 (d, J=13.9 Hz, 1H), 4.43 (t, J=7.03 Hz, 1H), 3.41 (s, 3H), 3.27 (s, 3H), 3.22 (s, 3H), 3.20 (s, 3H), 3.10 (s, 3H), 2.68 (s, 3H), 2.67 (s, 3H), 2.45-2.35 (m, 1H), 2.30-0.65 (m, 74H); ESI MS m/z 1269 $[C_{66}H_{113}N_{11}O_{13}+H]^+$.

Example 68

Preparation of Cis-Cyclosporin Alkyne

A solution of the acetate of cis-cyclosporin alkyne from Example 67 (37 mg, 0.02 mmol) in methanol (2 mL) was stirred at room temperature. Reaction mixture was treated with potassium carbonate (30 mg, 0.21 mmol) and allowed to keep stirring under $N_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford cis-cyclosporin alkyne (15 mg, 45%) as a white solid: $^1$H NMR (300 MHz, $CDCl_3$) δ 8.09 (d, J=9.8 Hz, 1H), 7.68 (d, J=7.2 Hz, 1H), 7.52 (d, J=8.4 Hz, 1H), 7.30 (d, J=7.8 Hz, 1H), 5.85-5.75 (m, 1H), 5.68 (dd, J=10.7, 3.9 Hz, 1H), 5.43 (d, J=7.4 Hz, 1H), 5.38 (d, J=10.0 Hz, 1H), 5.30 (dd, J=11.6, 4.2 Hz, 1H), 5.15-4.95 (m, 4H), 4.82 (t, J=7.2 Hz, 1H), 4.75-4.65 (m, 2H), 4.50 (t, J=7.2 Hz, 1H), 3.94 (t, J=6.8 Hz, 1H), 3.51 (s, 3H), 3.41 (s, 3H), 3.24 (s, 3H), 3.12 (s, 3H), 3.10 (s, 3H), 2.69 (s, 6H), 2.50-0.81 (m, 72H); ESI MS m/z 1227 $[C_{64}H_{111}N_{11}O_{12}+H]^+$; HPLC 98.7% (AUC), $t_R$=19.90 min.

Example 69

Preparation of the Acetates of Cis- and Trans-Deuterated Cyclosporin Vinyl Iodide A mixture of acetyl cyclosporin aldehyde from Example 2 (500 mg, 0.40 mmol) and iodoform-d (1.35 g, 4.0 mmol) in anhydrous THF (10 mL) was cooled to −78° C. After cooling, chromium chloride (1.0 g, 8.0 mmol) was quickly added to the reaction. Mixture was allowed to warm to 0° C. and stirred under $N_2$ atmosphere for 5 h. Mixture was poured into ice-water (300 mL) and extracted with ethyl acetate (3×200 mL). Combined organic layers were washed with brine, dried over sodium sulfate, and concentrated in vacuo. The crude product was purified by semi-preparative HPLC to afford the acetate of trans-deuterated cyclosporin vinyl iodide (220 mg, 40%) as a light brown solid: $^1$H NMR (300 MHz, $CDCl_3$) δ 8.47 (d, J=9.6 Hz, 1H), 8.01 (d, J=6.8 Hz, 1H), 7.57 (t, J=8.6 Hz, 2H), 6.44 (dd, J=8.6, 6.1 Hz, 2H), 6.01-5.56 (m, 4H), 5.52 (d, J=10.3 Hz, 2H), 5.28 (d, J=3.4 Hz, 1H), 5.24 (d, J=3.4 Hz, 1H), 4.97 (d, J=10.9 Hz, 3H), 4.85-4.76 (m, 5H), 4.64 (d, J=13.9 Hz, 2H), 4.43 (t, J=7.0 Hz, 2H), 3.43 (s, 3H), 3.25 (s, 3H), 3.24 (s, 3H), 3.20 (s, 3H), 3.11 (s, 3H), 2.67 (s, 3H), 2.66 (s, 3H), 2.01 (s, 2H), 1.32 (d, J=7.1 Hz, 4H), 1.28 (d, J=6.9 Hz, 4H), 1.06-0.74 (m, 52H); ESI MS m/z 1357 $[C_{63}H_{109}DIN_{11}O_{13}+H]^+$; and the acetate of cis-deuterated cyclosporin vinyl iodide (40 mg, 7%) as a light brown solid: $^1$H NMR (300 MHz, $CDCl_3$) δ 8.57 (d, J=9.6 Hz, 1H), 8.02 (d, J=6.8 Hz, 1H), 7.66 (d, J=9.0 Hz, 1H), 7.53 (d, J=7.7 Hz, 1H), 6.02-5.92 (m, 2H), 5.69 (dd, J=11.0, 3.9 Hz, 1H), 5.54 (d, J=3.9 Hz, 3H), 5.33-5.13 (m, 5H), 4.98 (d, J=11.1 Hz, 3H), 4.82 (t, J=7.3 Hz, 2H), 4.74 (t, J=9.5 Hz, 2H), 4.64 (d, J=13.8 Hz, 2H), 4.32 (t, J=7.0 Hz, 2H), 3.44 (s, 3H), 3.28 (s, 3H), 3.25 (s, 3H), 3.20 (s, 3H), 3.11 (s, 3H), 2.67 (s, 3H), 2.66 (s, 3H), 2.05 (s, 2H), 1.29 (d, J=5.5 Hz, 4H), 1.24 (d, J=11.9 Hz, 4H), 1.05 (d, J=6.4 Hz, 2H), 1.02-0.64 (m, 50H); ESI MS m/z 1357 $[C_{63}H_{109}DIN_{11}O_{13}+H]^+$.

Example 70

Preparation of the Acetate of Trans-Deuterated Cyclosporin Alkyne

A mixture of the acetate of trans-deuterated cyclosporin vinyl iodide from Example 69 (75 mg, 0.055 mmol), CuI (5 mg, 0.028 mmol), and $PdCl_2(PPh_3)_2$ (19 mg, 0.028 mmol) in $Et_3N$ (3 mL) was stirred at room temperature under $N_2$ atmosphere. Reaction mixture was then treated with (trimethylsilyl)acetylene (54 mg, 0.55 mmol). Reaction was allowed to stir for 4 h at room temperature. Solution was filtered through micro-filter and then concentrated in vacuo. The crude product was purified by semi-preparative HPLC to afford the acetate of trans-deuterated cyclosporin alkyne (45 mg, 61%) as an off-white solid: $^1$H NMR (300 MHz, CDCl$_3$) δ 8.21 (d, J=9.2 Hz, 1H), 7.88 (d, J=6.6 Hz, 1H), 7.71 (d, J=9.0 Hz, 1H), 7.47 (d, J=7.6 Hz, 1H), 5.80 (t, J=7.3 Hz, 1H), 5.56-5.35 (m, 3H), 5.29 (d, J=10.8 Hz, 2H), 5.17-4.97 (m, 3H), 4.88 (d, J=10.3 Hz, 3H), 4.86-4.45 (m, 5H), 4.31 (t, J=6.8 Hz, 2H), 3.91 (d, J=16.3 Hz, 1H), 3.80 (s, 3H), 3.25 (s, 3H), 3.08 (s, 3H), 3.05 (s, 3H), 3.01 (s, 3H), 2.93 (s, 3H), 2.53 (s, 3H), 2.51 (s, 3H), 1.85 (s, 1H), 1.81 (s, 2H), 1.21-1.08 (m, 8H), 0.89-0.54 (m, 50H), 0.10 (s, 9H); ESI MS m/z 1328 [C$_{68}$H$_{118}$DN$_{11}$O$_{13}$Si+H]$^+$.

Example 71

Preparation of Trans-Deuterated Cyclosporin Alkyne

A solution of acetate of trans-deuterated cyclosporin alkyne from Example 70 (44 mg, 0.033 mmol) in methanol (2 mL) was stirred at room temperature. Reaction mixture was treated with potassium carbonate (55 mg, 0.40 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford trans-deuterated cyclosporin alkyne (29 mg, 72%) as a white solid: $^1$H NMR (300 MHz, CDCl$_3$) δ 7.93 (d, J=9.8 Hz, 1H), 7.64 (d, J=7.3 Hz, 1H), 7.46 (d, J=8.3 Hz, 1H), 7.19 (d, J=7.8 Hz, 1H), 5.99 (t, J=7.7 Hz, 2H), 5.70 (dd, J=11.1, 4.1 Hz, 1H), 5.49 (d, J=6.0 Hz, 2H), 5.31 (dd, J=10.9, 3.7 Hz, 1H), 5.13-4.62 (m, 16H), 4.52 (t, J=7.3 Hz, 2H), 3.79 (t, J=6.5 Hz, 2H), 3.50 (s, 3H), 3.38 (s, 3H), 3.25 (s, 3H), 3.10 (s, 6H), 2.70 (s, 3H), 2.69 (s, 3H), 1.91 (s, 2H), 1.35 (d, J=7.2 Hz, 2H), 1.26 (d, J=5.0 Hz, 2H), 1.08-0.81 (m, 50H), 0.71 (d, J=6.1 Hz, 1H); ESI MS m/z 1214 [C$_{63}$H$_{108}$DN$_{11}$O$_{12}$+H]$^+$; HPLC>99% (AUC), t$_R$=18.82 min.

Example 72

Preparation of the Acetate of Trans-Deuterated Cyclosporin Alkyne

ZnCl$_2$ (0.6 mL, 1 M in THF, 0.6 mmol) was added to a solution of 1-propynylmagnesium bromide (1.2 mL, 0.5 M in THF, 0.6 mmol) in THF (3 mL) at 0° C. Mixture was stirred under N$_2$ atmosphere for 5 min. Mixture was warmed to room temperature and then treated with the acetate of trans-deuterated cyclosporin vinyl iodide from Example 69 (80 mg, 0.060 mmol) and PdCl$_2$(PPh$_3$)$_2$ (20 mg, 0.030 mmol). Mixture stirred for 4 h under N$_2$ atmosphere at room temperature. Solution was filtered through micro-filter and then concentrated in vacuo. The crude product was purified by semi-preparative HPLC to afford the acetate of trans-deuterated cyclosporin alkyne (62 mg, 83%) as an off-white solid: $^1$H NMR (300 MHz, CDCl$_3$) δ 8.44 (d, J=9.3 Hz, 1H), 8.04 (d, J=6.7 Hz, 1H), 7.98 (d, J=9.2 Hz, 1H), 7.64 (d, J=7.7 Hz, 1H), 5.83-5.43 (m, 7H), 5.28 (d, J=3.3 Hz, 1H), 5.24 (d, J=3.3 Hz, 1H), 5.18 (d, J=5.7 Hz, 2H), 5.06-4.70 (m, 10H), 4.64 (d, J=14.2 Hz, 1H), 4.46 (t, J=6.9 Hz, 2H), 3.42 (s, 3H), 3.24 (s, 3H), 3.22 (s, 3H), 3.19 (s, 3H), 3.11 (s, 3H), 2.69 (s, 3H), 2.68 (s, 3H), 2.01 (s, 2H), 1.91 (s, 1H), 1.31 (dd, J=10.8, 7.2 Hz, 6H), 1.04 (d, J=6.5 Hz, 2H), 1.01-0.70 (m, 52H); ESI MS m/z 1270 [C$_{66}$H$_{112}$DN$_{11}$O$_{13}$+H]$^+$.

Example 73

Preparation of Trans-Deuterated Cyclosporin Alkyne

A solution of the acetate of trans-deuterated cyclosporine alkyne from Example 72 (62 mg, 0.049 mmol) in methanol (2 mL) was stirred at room temperature. Reaction mixture was treated with potassium carbonate (70 mg, 0.50 mmol) and was allowed to keep stirring under N$_2$ atmosphere overnight. Mixture was diluted with ethyl acetate, washed with saturated sodium bicarbonate solution and brine, dried over sodium sulfate, and concentrated in vacuo. The crude product was purified by semi-preparative HPLC to afford trans-deuterated cyclosporine alkyne (31 mg, 52%) as a white solid: $^1$H NMR (300 MHz, CDCl$_3$) δ 7.92 (d, J=9.7 Hz, 1H), 7.63 (d, J=7.3 Hz, 1H), 7.44 (d, J=8.2 Hz, 1H), 7.20 (d, J=7.8 Hz, 1H), 6.23 (t, J=7.3 Hz, 1H), 5.49 (d, J=6.0 Hz, 2H), 5.31 (dd, J=10.7, 3.4 Hz, 1H), 5.11-4.62 (m, 20H), 4.52 (t, J=7.2 Hz, 2H), 3.82 (t, J=6.5 Hz, 2H), 3.51 (s, 3H), 3.38 (s, 3H), 3.25 (s, 3H), 3.11 (s, 3H), 3.10 (s, 3H), 2.70 (s, 3H), 2.68 (s, 3H), 1.34 (d, J=7.2 Hz, 2H), 1.26 (d, J=4.8 Hz, 2H), 1.08-0.81 (m, 52H), 0.73 (d, J=6.4 Hz, 1H); ESI MS m/z 1228 [C$_{64}$H$_{110}$DN$_{11}$O$_{12}$+H]$^+$; HPLC>99% (AUC), t$_R$=19.47 min.

Example 74

Preparation of Cyclosporin Diol

To a mechanically stirred solution of diisopropylamine (2.6 mL, 18 mmol) in THF (50 mL) at −78° C. was added dropwise n-butyllithium (6.6 mL, 2.5 M in hexane, 17 mmol), then the mixture was stirred for 0.5 h. A solution of cyclosporin A (1.0 g, 0.83 mmol) in THF (8 mL) was added, and then the mixture was stirred for 2 h at −78° C. Paraformaldehyde (8.0 g) was heated to 170° C. and the resulting formaldehyde gas was transferred into the reaction via a glass tube which was wrapped with cotton and aluminum foil over 2 h. After stirred another 1 h at −78° C., the reaction mixture was quenched with water (10 mL). The mixture was allowed to warm to room temperature, diluted with ethyl acetate (150 mL) and washed with water (2×50 mL). The organic layer was separated, dried over anhydrous sodium sulfate and concentrated under vacuum. The crude material was purified by semi-preparative HPLC to afford cyclosporin diol (0.45 g, 44%) as a white solid: $^1$H NMR (300 MHz, CDCl$_3$) δ 8.09 (d, J=9.9 Hz, 1H), 7.70 (d, J=7.4 Hz, 1H), 7.57 (d, J=8.2 Hz, 1H), 7.15 (overlapped with CHCl$_3$, 1H), 5.70 (dd, J=11.0, 4.0 Hz, 1H), 5.49 (d, J=6.4 Hz, 1H), 5.38-5.30 (m, 3H), 5.16-4.93 (m, 5H), 4.83 (t, J=7.2 Hz, 1H), 4.65 (t, J=9.5 Hz, 1H), 4.54 (t, J=7.2 Hz, 1H), 4.05 (d, J=6.8 Hz, 2H), 3.73 (t, J=6.3 Hz, 1H), 3.49 (s, 3H), 3.30 (s, 3H), 3.25 (s, 3H), 3.15 (s, 3H), 3.11 (s, 3H), 2.70 (s, 3H), 2.69 (s, 3H), 2.50-2.38 (m, 2H), 2.20-1.92 (m, 6H), 1.75-0.65 (m, 64H); ESI MS m/z 1233 [C$_{63}$H$_{113}$N$_{11}$O$_{13}$+H]$^+$.

Example 75

Preparation of Cyclosporin Diacetate

To a solution of cyclosporin diol from Example 74 (0.43 g, 0.35 mmol) in methylene chloride (5 mL) was added pyridine (0.57 mL, 7.0 mmol) followed by 4-(dimethylamino)pyridine (86 mg, 0.70 mmol) and acetic anhydride (1.0 mL, 10.5 mmol). The reaction mixture was stirred for 2 d at room temperature. The reaction was diluted with ethyl ether (150 mL), washed with a saturated solution of sodium bicarbonate (30 mL), 1N HCl solution (30 mL) and brine (30 mL). The organic layer was separated, dried over anhydrous sodium sulfate and concentrated under vacuum. The crude material was purified by semi-preparative HPLC to afford cyclosporin diacetate (0.23 g, 50%) as a white solid: $^1$H NMR (300 MHz, CDCl$_3$) δ 8.60 (d, J=9.8 Hz, 1H), 8.05 (d, J=6.6 Hz, 1H), 7.55 (d, J=7.8 Hz, 1H), 7.49 (d, J=9.3 Hz, 1H), 5.68 (dd, J=11.0, 4.0 Hz, 1H), 5.49 (s, 2H), 5.40-4.95 (m, 8H), 4.85 (t, J=7.5 Hz, 1H), 4.76 (t, J=9.3 Hz, 1H), 4.58-4.34 (m, 3H), 3.37 (s, 3H), 3.27 (s, 3H), 3.23 (s, 3H), 3.20 (s, 3H), 3.14 (s, 3H), 2.67 (s, 3H), 2.66 (s, 3H), 2.48-2.35 (m, 1H), 2.10 (s, 3H), 2.01 (s, 3H), 1.98-1.85 (m, 2H), 1.75-0.65 (m, 67H); ESI MS m/z 1317 [C$_{67}$H$_{117}$N$_{11}$O$_{15}$+H]$^+$.

Example 76

Preparation of Cyclosporin Aldehyde

Ozone was bubbled into a solution of cyclosporin diacetate from Example 75 (0.22 g, 0.17 mmol) in methylene chloride (10 mL) at −78° C. until a blue color was developed. The mixture was degassed with nitrogen for a few min and dimethylsulfide (0.4 mL) was added at −78° C. The reaction mixture was allowed to warm to room temperature and stirred for 3 h. The reaction mixture was concentrated in vacuo and the residue was dissolved in ethyl acetate (120 mL), washed with water (2×20 mL) and brine (30 mL), dried over sodium sulfate, filtered, and concentrated in vacuo to afford cyclosporin aldehyde (0.19 g, 86%) as a white solid. The crude was carried to the next step without further purification: $^1$H NMR (300 MHz, CDCl$_3$) δ 9.55 (d, J=3.4 Hz, 1H), 8.60 (d, J=9.9 Hz, 1H), 7.96 (d, J=7.1 Hz, 1H), 7.53 (d, J=7.7 Hz, 1H), 7.33 (d, J=9.1 Hz, 1H), 5.68 (dd, J=−11.0, 4.0 Hz, 1H), 5.53 (d, J=11.2 Hz, 1H), 5.47 (d, J=11.2 Hz, 1H), 5.30 (dd, J=12.3, 3.6 Hz, 1H), 5.18-4.92 (m, 5H), 4.84 (t, J=6.9 Hz, 1H), 4.72 (t, J=9.6 Hz, 1H), 4.55-4.35 (m, 3H), 3.39 (s, 3H), 3.30 (s, 3H), 3.29 (s, 3H), 3.21 (s, 3H), 3.12 (s, 3H), 2.66 (s, 3H), 2.65 (s, 3H), 2.48-2.30 (m, 3H), 2.10 (s, 3H), 1.99 (s, 3H), 1.80-0.75 (m, 64H); ESI MS m/z 1305 [C$_{65}$H$_{113}$N$_{11}$O$_{16}$+H]$^+$.

Example 77

Preparation of the Acetates of Cis- and Trans-Cyclosporin Vinyl Iodide

To an ice-cooled suspension of chromium(II) chloride (664 mg, 5.4 mmol) in THF (7 mL) was added a solution of cyclosporin aldehyde from Example 76 (0.35 g, 0.27 mmol) and iodoform (850 mg, 2.16 mmol) in THF (7 mL), then the mixture was stirred at 0° C. After 4 h, the reaction mixture was poured into ice-water (40 mL). The aqueous layer was separated and extracted with ethyl acetate (3×50 mL). The combined organics were dried over anhydrous sodium sulfate and concentrated under vacuum. The crude was purified by semi-preparative HPLC to afford the acetate of cis-cyclosporin vinyl iodide (26 mg, 7%): $^1$H NMR (CDCl$_3$, 300 MHz) δ 8.62 (d, J=9.6 Hz, 1H), 8.02 (d, J=6.9 Hz, 1H), 7.60 (d, J=7.5 Hz, 1H), 7.55 (d, J=9.3 Hz, 1H), 6.07 (d, J=7.4 Hz, 1H), 6.02-5.92 (m, 1H), 5.69 (dd, J=11.1, 3.9 Hz, 1H), 5.50 (dd, J=15.6, 11.7 Hz, 2H), 5.30-4.93 (m, 6H), 4.85 (t, J=7.2 Hz, 1H), 4.74 (t, J=9.3 Hz, 1H), 4.55-4.32 (m, 3H), 3.36 (s, 3H), 3.29 (s, 3H), 3.23 (s, 3H), 3.20 (s, 3H), 3.14 (s, 3H), 2.67 (s, 6H), 2.43-2.32 (m, 1H), 2.23-2.15 (m, 2H), 2.10 (s, 3H), 2.06 (s, 3H), 1.95-1.82 (m, 3H), 1.75-1.60 (m, 3H), 1.48-0.82 (m, 58H); ESI MS m/z 1429 [C$_{66}$H$_{114}$IN$_{11}$O$_{15}$+H]$^+$; the acetate of trans-cyclosporin vinyl iodide (0.18 g, 47%): $^1$H NMR (CDCl$_3$, 300 MHz) δ 8.54 (d, J=9.9 Hz, 1H), 8.00 (d, J=6.6 Hz, 1H), 7.58 (d, J=7.5 Hz, 1H), 7.43 (d, J=9.0 Hz, 1H), 6.45-6.35 (m, 1H), 5.83 (d, J=14.4 Hz, 1H), 5.69 (dd, J=10.8, 3.9 Hz, 1H), 5.55-5.43 (m, 2H), 5.38 (dd, J=12.0, 3.9 Hz, 1H), 5.30-4.93 (m, 5H), 4.85 (t, J=6.9 Hz, 1H), 4.77 (t, J=9.6 Hz, 1H), 4.53-4.30 (m, 3H), 3.36 (s, 3H), 3.27 (s, 3H), 3.26 (s, 3H), 3.20 (s, 3H), 3.15 (s, 3H), 2.67 (s, 3H), 2.66 (s, 3H), 2.43-2.32 (m, 1H), 2.23-2.11 (m, 2H), 2.10 (s, 3H), 2.02 (s, 3H), 1.95-1.60 (m, 6H), 1.48-0.75 (m, 58H); ESI MS m/z 1429 [C$_{66}$H$_{114}$IN$_{11}$O$_{15}$+H]$^+$.

Example 78

Preparation of the Acetate of Cyclosporin Alkyne

To a mixture of the acetate of trans-cyclosporin vinyl iodide from Example 77 (60 mg, 0.042 mmol), copper(I) iodide (4 mg, 0.021 mmol), dichlorobis(triphenylphosphine)palladium(II) (15 mg, 0.021 mmol) in triethylamine (2 mL) was added (trimethylsilyl)acetylene (60 μL, 0.42 mmol), then the mixture was stirred at room temperature for 3 h. The reaction mixture was filtered through a micro-filter and concentrated under vacuum. The crude was purified by semi-preparative HPLC to afford the acetate of cyclosporin alkyne (16 mg, 28%) as a white solid: $^1$H NMR (CDCl$_3$, 300 MHz) δ 8.53 (d, J=9.3 Hz, 1H), 8.06 (d, J=6.6 Hz, 1H), 7.68 (app t, J=8.7 Hz, 2H), 6.02 (dt, J=15.9, 7.5 Hz, 1H), 5.70 (dd, J=10.8, 3.9 Hz, 1H), 5.55-5.37 (m, 2H), 5.35-5.13 (m, 4H), 5.06-4.93 (m, 4H), 4.87 (t, J=7.2 Hz, 1H), 4.75 (t, J=9.3 Hz, 1H), 4.53-4.33 (m, 4H), 3.38 (s, 3H), 3.27 (s, 3H), 3.24 (s, 3H), 3.19 (s, 3H), 3.12 (s, 3H), 2.69 (s, 3H), 2.68 (s, 3H), 2.43-2.32 (m, 1H), 2.23-2.11 (m, 2H), 2.11 (s, 3H), 2.01 (s, 3H), 1.95-1.60 (m, 6H), 1.48-0.75 (m, 56H), 0.17 (s, 9H); ESI MS m/z 1399 [C$_{71}$H$_{123}$N$_{11}$O$_{15}$Si+H]$^+$.

Example 79

Preparation of Cyclosporin Alkyne

To a solution of the acetate of cyclosporin alkyne from Example 78 (16 mg, 0.011 mmol) in MeOH (2 mL) was added potassium carbonate (46 mg, 0.33 mmol), then the mixture was stirred at room temperature. After 12 h, the reaction mixture was quenched with a saturated solution of ammonium chloride (10 mL). The aqueous layer was extracted with ethyl acetate (3×20 mL). The combined organics were dried over anhydrous sodium sulfate and concentrated under vacuum. The crude material was purified by semi-preparative HPLC to afford cyclosporin alkyne (8 mg, 57%) as a white solid: $^1$H NMR (300 MHz, CDCl$_3$) δ 8.07 (d, J=9.9 Hz, 1H), 7.68 (d, J=8.4 Hz, 1H), 7.45 (d, J=8.1 Hz, 1H), 7.20 (d, J=7.8 Hz, 1H), 6.28-6.15 (m, 1H), 5.70 (dd, J=10.8, 3.6 Hz, 1H), 5.50 (d, J=6.6 Hz, 1H), 5.39 (d, J=15.3 Hz, 1H), 5.30 (dd, J=11.7, 3.6 Hz, 1H), 5.12-4.92 (m, 5H), 4.84 (t, J=6.9 Hz, 1H), 4.66 (t, J=9 Hz, 1H), 4.51 (t, J=7.2 Hz, 1H), 4.04 (d, J=6.6 Hz, 2H), 3.76 (t, J=6.0 Hz, 1H), 3.51 (s, 3H), 3.31 (s, 3H), 3.27 (s, 3H), 3.15 (s, 3H), 3.11 (s, 3H), 2.69 (s, 3H), 2.68 (s, 3H), 2.55-2.38 (m, 5H), 2.20-1.90 (m, 6H), 1.80-1.60 (m, 5H), 1.45-0.75 (m, 54H); ESI MS m/z 1243 [C$_{64}$H$_{111}$N$_{11}$O$_{13}$+H]$^+$; HPLC 96.2% (AUC), t$_R$=13.18 min.

Example 80

Preparation of the Acetate of Cyclosporin Alkyne

To an ice-cooled solution of 1-(trimethylsilyl)-1-propyne-d$_3$ (49 mg, 0.42 mmol) in triethylamine (2 mL) was added tetrabutylammonium fluoride (0.5 mL, 1 M in THF, 0.5 mmol), then the mixture was stirred for 10 min. The reaction mixture was allowed to warm to room temperature, then the solution was transferred into a mixture of the acetate of trans-cyclosporin vinyl iodide from Example 77 (60 mg, 0.042 mmol), copper(I) iodide (4 mg, 0.021 mmol), dichlorobis (triphenylphosphine)palladium(II) (15 mg, 0.021 mmol). The resulting reaction mixture was stirred at room temperature for 3 h. The reaction mixture was filtered through a micro-filter and concentrated under vacuum. The crude was purified by semi-preparative HPLC to afford the acetate of cyclosporin alkyne (47 mg, 84%) as a white solid: $^1$H NMR (CDCl$_3$, 300 MHz) δ 8.56 (d, J=9.9 Hz, 1H), 8.04 (d, J=6.6 Hz, 1H), 7.68 (d, J=7.5 Hz, 1H), 7.60 (d, J=9.3 Hz, 1H), 5.88-5.77 (m, 1H), 5.70 (dd, J=10.8, 3.9 Hz, 1H), 5.57-5.42 (m, 2H), 5.40 (dd, J=12.0, 3.9 Hz, 1H), 5.30-5.20 (m, 2H), 5.17 (t, J=7.5 Hz, 1H), 5.05-4.94 (m, 3H), 4.90-4.75 (m, 2H), 4.57-4.35 (m, 3H), 3.37 (s, 3H), 3.26 (s, 3H), 3.24 (s, 3H), 3.19 (s, 3H), 3.14 (s, 3H), 2.68 (s, 6H), 2.45-2.37 (m, 1H), 2.30-2.12 (m, 2H), 2.11 (s, 3H), 2.02 (s, 3H), 1.95-1.65 (m, 6H), 1.48-0.75 (m, 58H); ESI MS m/z 1344 $[C_{69}H_{114}D_3N_{11}O_{15}+H]^+$.

Example 81

Preparation of Cyclosporin Alkyne

To a solution of the acetate of cyclosporin alkyne from Example 80 (45 mg, 0.033 mmol) in MeOH (3 mL) was added potassium carbonate (137 mg, 0.99 mmol), then the mixture was stirred at room temperature. After 12 h, the reaction mixture was quenched with a saturated solution of ammonium chloride (15 mL). The aqueous layer was extracted with ethyl acetate (3×30 mL). The combined organics were dried over anhydrous sodium sulfate and concentrated under vacuum. The crude material was purified by semi-preparative HPLC to afford cyclosporin alkyne (24 mg, 57%) as a white solid: $^1$H NMR (300 MHz, CDCl$_3$) δ 8.07 (d, J=9.6 Hz, 1H), 7.68 (d, J=7.2 Hz, 1H), 7.47 (d, J=8.1 Hz, 1H), 7.20 (d, J=8.1 Hz, 1H), 6.05-5.95 (m, 1H), 5.70 (dd, J=10.8, 3.6 Hz, 1H), 5.50 (d, J=6.6 Hz, 1H), 5.35 (d, J=16.2 Hz, 1H), 5.30 (dd, J=11.7, 3.6 Hz, 1H), 5.12-4.90 (m, 5H), 4.83 (t, J=6.9 Hz, 1H), 4.65 (t, J=9.0 Hz, 1H), 4.54 (t, J=7.2 Hz, 1H), 4.04 (d, J=6.6 Hz, 2H), 3.72 (t, J=6.3 Hz, 1H), 3.50 (s, 3H), 3.30 (s, 3H), 3.27 (s, 3H), 3.14 (s, 3H), 3.11 (s, 3H), 2.70 (s, 3H), 2.69 (s, 3H), 2.55-2.35 (m, 2H), 2.20-1.90 (m, 5H), 1.80-1.58 (m, 6H), 1.45-0.75 (m, 56H); ESI MS m/z 1260 $[C_{65}H_{110}D_3N_{11}O_{13}+H]^+$; HPLC>99% (AUC), $t_R$=13.48 min.

Example 82

Preparation of the Acetate of Cyclosporin Alkyne

To an ice-cooled solution of 1-propynylmagnesium bromide (0.76 mL, 0.5 M in THF, 0.38 mmol) in THF (1 mL) was added a solution of zinc chloride (0.38 mL, 1 M in ethyl ether, 0.38 mmol). The reaction was stirred at 0° C. for 10 min, and then allowed to warm to room temperature. A solution of the acetate of trans-cyclosporin vinyl iodide from Example 77 (54 mg, 0.038 mmol) in THF (2 mL) was added into the reaction mixture followed by copper(I) iodide (2 mg, 0.008 mmol) and dichlorobis(triphenylphosphine)palladium(II) (3 mg, 0.004 mmol). The resulting reaction mixture was stirred at room temperature for 1 h, and then quenched with a saturated solution of ammonium chloride. The aqueous layer was extracted with ethyl acetate (3×30 mL). The combined organics were dried over anhydrous sodium sulfate and concentrated under vacuum. The crude was purified by semi-preparative HPLC to afford the acetate of cyclosporin alkyne (27 mg, 53%) as a white solid: $^1$H NMR (CDCl$_3$, 300 MHz) δ 8.55 (d, J=9.6 Hz, 1H), 8.04 (d, J=6.9 Hz, 1H), 7.68 (d, J=7.8 Hz, 1H), 7.60 (d, J=9.0 Hz, 1H), 5.88-5.75 (m, 1H), 5.70 (dd, J=10.8, 3.9 Hz, 1H), 5.53 (d, J=11.4 Hz, 1H), 5.45 (d, J=11.1 Hz, 1H), 5.39 (dd, J=12.0, 3.9 Hz, 1H), 5.30-5.20 (m, 2H), 5.17 (t, J=7.5 Hz, 1H), 5.05-4.94 (m, 3H), 4.90-4.75 (m, 2H), 4.57-4.35 (m, 3H), 3.37 (s, 3H), 3.26 (s, 3H), 3.24 (s, 3H), 3.19 (s, 3H), 3.13 (s, 3H), 2.68 (s, 6H), 2.45-2.35 (m, 1H), 2.30-2.12 (m, 2H), 2.11 (s, 3H), 2.02 (s, 3H), 1.95-1.65 (m, 101H), 1.48-0.75 (m, 57H); ESI MS m/z 1341 $[C_{69}H_{117}N_{11}O_{15}+H]^+$.

Example 83

Preparation of Cyclosporin Alkyne

To a solution of the acetate of cyclosporin alkyne from Example 82 (25 mg, 0.019 mmol) in MeOH (2 mL) was added potassium carbonate (79 mg, 0.57 mmol), then the mixture was stirred at room temperature. After 8 h, the reaction mixture was quenched with a saturated solution of ammonium chloride (10 mL). The aqueous layer was extracted with ethyl acetate (3×20 mL). The combined organics were dried over anhydrous sodium sulfate and concentrated under vacuum. The crude material was purified by semi-preparative HPLC to afford cyclosporin alkyne (14 mg, 58%): $^1$H NMR (300 MHz, CDCl$_3$) δ 8.06 (d, J=9.9 Hz, 1H), 7.68 (d, J=7.5 Hz, 1H), 7.45 (d, J=8.1 Hz, 1H), 7.18 (d, J=8.1 Hz, 1H), 6.05-5.95 (m, 1H), 5.70 (dd, J=10.8, 3.6 Hz, 1H), 5.50 (d, J=6.6 Hz, 1H), 5.40-5.25 (m, 2H), 5.12-4.90 (m, 5H), 4.83 (t, J=6.9 Hz, 1H), 4.65 (t, J=9 Hz, 1H), 4.54 (t, J=7.2 Hz, 1H), 4.04 (d, J=6.6 Hz, 2H), 3.73 (t, J=6.3 Hz, 1H), 3.50 (s, 3H), 3.30 (s, 3H), 3.27 (s, 3H), 3.14 (s, 3H), 3.11 (s, 3H), 2.70 (s, 3H), 2.68 (s, 3H), 2.55-2.35 (m, 2H), 2.20-1.98 (m, 5H), 1.92 (d, J=1.7 Hz, 3H), 1.80-1.55 (m, 6H), 1.48-0.70 (m, 56H); ESI MS m/z 1257 $[C_{65}H_{113}N_{11}O_{13}+H]^+$; HPLC>99% (AUC), $t_R$=13.41 min.

Example 84

Preparation of the Acetate of Cyclosporin Alkyne

To a dried 25 mL flask charged with a solution of the acetate of trans-cyclosporin vinyl iodide from Example 77 (60 mg, 0.04 mmol) in triethylamine (2 mL) was added copper(I) iodide (3.8 mg, 0.02 mmol), followed by dichlorobis (triphenylphosphine)palladium(II) (7.0 mg, 0.01 mmol), and propargyl alcohol (0.02 mL, 0.40 mmol). After 2.5 h, the reaction mixture was filtered through a microfilter, and then concentrated under reduced pressure. The crude material was purified by semi-preparative HPLC to yield the acetate of cyclosporin alkyne (54 mg, quantitative): $^1$H NMR (300 MHz, CDCl$_3$) δ 8.47 (d, J=9.8 Hz, 1H), 7.94 (d, J=6.8 Hz, 1H), 7.42 (d, J=7.7 Hz, 1H), 7.27 (d, J=7.6 Hz, 1H), 5.38-5.26 (m, 1H), 5.47 (s, 2H), 5.45-5.32 (m, 1H), 5.22 (dd, J=9.3, 3.2 Hz, 1H), 5.15 (dd, J=7.7, 5.8 Hz, 1H), 5.07-4.91 (m, 2H), 4.83 (t, J=6.9 Hz, 1H), 4.55-4.21 (m, 4H), 3.35 (s, 3H), 3.27 (s, 3H), 3.26 (s, 3H), 3.21 (s, 3H), 3.15 (s, 3H), 2.67 (s, 3H), 2.65 (s, 3H), 2.44-2.11 (m, 1H), 2.10 (s, 3H), 2.03 (s, 3H), 2.01-1.59 (m, 4H), 1.49-0.74 (m, 68H); ESI MS m/z 1357 $[C_{69}H_{117}N_{11}O_{16}+H]^+$.

Example 85

Preparation of Cyclosporin Alkyne

To a dried 25 mL flask charged with a solution of the acetate of cyclosporin alkyne from Example 84 (54 mg, 0.04 mmol) in methanol (2 mL) was added potassium carbonate (110 mg, 0.80 mmol). This was allowed to stir at room temperature for 5 h, after which it was quenched with a saturated solution of ammonium chloride (8 mL). This was allowed to stir for 10 min. The aqueous layer was then extracted with ethyl acetate (3×40 mL). The combined organics were washed with brine (15 mL), dried over anhydrous sodium sulfate, and then concentrated under reduced pressure. The crude material was purified by semi-preparative HPLC to yield cyclosporin alkyne (28 mg, 54%) as a white solid: $^1$H NMR (300 MHz, CDCl$_3$) δ 7.80 (d, J=9.7 Hz, 1H), 7.55-7.47 (m, 2H), 7.32 (d, J=7.7 Hz, 1H), 6.05-5.92 (m, 1H), 5.67 (dd, J=10.7, 3.5 Hz, 1H), 5.48-5.35 (m, 3H), 5.14-4.86 (m, 6H), 4.81 (t, J=7.2 Hz, 1H), 4.74 (t, J=9.3 Hz, 1H), 4.47 (t, J=7.1 Hz, 1H), 4.34 (d, J=5.2 Hz, 1H), 4.09-3.96 (m, 3H), 3.49 (s, 3H), 3.31 (s, 3H), 3.24 (s, 3H), 3.18 (s, 3H), 3.14 (s, 3H), 3.10 (s, 3H), 2.69 (s, 6H), 2.48-2.37 (m, 1H), 2.32-2.03 (m, 5H), 2.01-0.77 (m, 61H); ESI MS m/z 1274 [C$_{65}$H$_{113}$N$_{11}$O$_{14}$+H]$^+$; HPLC>99% (AUC), $t_R$=17.32 min.

Example 86

Preparation of the Acetate of Cyclosporin Alkyne Alcohol

To a dried 25 mL flask charged with a solution of the acetate of trans-cyclosporin vinyl iodide from Example 77 (120 mg, 0.08 mmol) in triethylamine (3 mL) was added copper(I) iodide (15 mg, 0.08 mmol) followed by dichlorobis(triphenylphosphine)palladium(II) (21 mg, 0.04 mmol) and 3-butyn-2-ol (0.06 mL, 0.80 mmol). After 2.5 h, the reaction mixture was filtered through a microfilter then concentrated under reduced pressure. The crude material was purified by semi-preparative HPLC to yield the acetate of cyclosporin alkyne alcohol (79 mg, 73%): $^1$H NMR (300 MHz, CDCl$_3$) δ 8.49 (d, J=4.7 Hz, 0.5H), 8.46 (d, J=4.6 Hz, 0.5H), 7.98 (d, J=6.0 Hz, 0.5H), 7.96 (d, J=5.9 Hz, 0.5H), 7.49 (d, J=7.0 Hz, 0.5H), 7.46 (d, J=6.7 Hz, 0.5H), 7.38 (d, J=9.1 Hz, 0.5H), 7.34 (d, J=9.1 Hz, 0.5H), 5.79-5.58 (m, 1H), 5.47 (s, 2H), 5.43-5.09 (m, 3H), 5.04-4.78 (m, 4H), 4.76-4.33 (m, 3H), 3.37 (s, 1.5H), 3.35 (s, 1.5H), 3.25 (s, 6H), 3.20 (s, 3H), 3.14 (s, 1.5H), 3.13 (s, 1.5H), 2.67 (s, 3H), 2.66 (s, 3H), 2.49-2.18 (m, 1H), 2.10 (s, 3H), 2.03 (s, 3H), 1.98-1.58 (m, 4H), 1.47-0.71 (m, 70H); ESI MS m/z 1371 [C$_{70}$H$_{119}$N$_{11}$O$_{16}$+H]$^+$.

Example 87

Preparation of Cyclosporin Alkyne

To a dried 25 mL flask charged with a solution of the acetate of cyclosporin alkyne from Example 86 (25 mg, 0.018 mmol) in methanol (1.5 mL) was added potassium carbonate (50 mg, 0.36 mmol). This was allowed to stir at room temperature for 3.5 h, after which it was quenched with a saturated solution of ammonium chloride (1.5 mL). This was allowed to stir for 5 min. The aqueous layer was then extracted with ethyl acetate (2×20 mL). The combined organics were washed with brine (15 mL), dried over anhydrous sodium sulfate, and then concentrated under reduced pressure. The crude material was purified twice by semi-preparative HPLC to yield cyclosporin alkyne (11 mg, 48%) as a white solid and mixture of diastereomers: $^1$H NMR (300 MHz, CDCl$_3$) δ 7.89 (d, J=10.1 Hz, 0.7H), 7.70 (d, J=10.3 Hz, 0.3H), 7.54-7.44 (m, 2H), 7.30-7.21 (m, 1H), 6.02-5.86 (m, 1H), 5.67 (dd, J=7.1, 3.9 Hz, 1H), 5.49-5.28 (m, 3H), 5.17-4.42 (m, 9H), 4.09-3.91 (m, 3H), 3.50 (s, 3H), 3.31(s, 3H), 3.24 (s, 3H), 3.14 (s, 3H), 3.10 (s, 2.1H), 3.09 (s, 0.9H), 2.68 (s, 6H), 2.49-2.30 (m, 1H), 2.29-1.89 (m, 5H), 1.84-0.68 (m, 67H); ESI MS m/z 1287 [C$_{66}$H$_{115}$N$_{11}$O$_{14}$+H]$^+$; HPLC>99% (AUC), $t_R$=17.96 min.

Example 88

Preparation of the Diacetate of Cyclosporin Ene-Yne-Ene

To a 25 mL flask charged with a solution of the acetate of cyclosporin alkynyl alcohol from Example 86 (54 mg, 0.039 mmol) in benzene (2 mL) was added Burgess reagent (19 mg, 0.078 mmol). The resulting mixture was heated at 60° C. After 3.5 h, an additional 8 mg of Burgess reagent were added. The reaction was again heated at 60° C. for 2 h. The mixture was cooled to room temperature and partitioned between ether (60 mL) and water (15 mL). The aqueous layer was extracted once with ether (30 mL). The combined ethereal layers were washed with brine (20 mL), dried over anhydrous sodium sulfate, and then concentrated under reduced pressure. The crude material was purified by semi-preparative HPLC to yield the diacetate of cyclosporin ene-yne-ene (18 mg, 35%): $^1$H NMR (300 MHz, CDCl$_3$) δ 8.54 (d, J=9.7 Hz, 1H), 8.03 (d, J=6.8 Hz, 1H), 7.62 (d, J=7.7 Hz, 1H), 7.51 (d, J=9.1 Hz, 1H), 6.04-5.86 (m, 1H), 5.74-5.65 (m, 1H), 5.88 (dd, J=17.5, 2.2 Hz, 2H), 5.57-5.42 (m, 3H), 4.95 (t, J=7.5 Hz, 1H), 5.19-4.93 (m, 3H), 4.85 (t, J=7.4 Hz, 1H), 4.79 (t, J=12.0 Hz, 1H), 4.57-3.31 (m, 3H), 3.37 (s, 3H), 3.27 (s, 3H), 3.25 (s, 3H), 3.20 (s, 3H), 3.13 (s, 3H), 2.68 (s, 3H), 2.67 (s, 3H), 2.47-2.31 (m, 1H), 2.24-2.10 (m, 3H), 2.10 (s, 3H), 2.02 (s, 3H), 1.98-1.82 (m, 4H), 1.80-1.60 (m, 4H), 1.48-0.72 (m, 58H); ESI MS m/z 1353 [C$_{70}$H$_{117}$N$_{11}$O$_{15}$+H]$^+$.

Example 89

Preparation of Cyclosporin Ene-Yne-Ene

A solution of the diacetate of cyclosporin ene-yne-ene from Example 88 (28 mg, 0.02 mmol) in methanol (2 mL) was treated with potassium carbonate (55 mg, 0.40 mmol). This was allowed to stir at room temperature overnight, after which it was quenched with a saturated solution of ammonium chloride (10 mL). The aqueous layer was then extracted with ethyl acetate (2×40 mL). The combined organics were washed with brine (15 mL), dried over anhydrous sodium sulfate, and then concentrated under reduced pressure. The crude material was purified by semi-preparative HPLC to yield cyclosporin ene-yne-ene (8 mg, 32%) as a white solid: $^1$H NMR (300 MHz, CDCl$_3$) δ 8.07 (d, J=9.8 Hz, 1H), 7.70 (d, J=7.3 Hz, 1H), 7.58 (d, J=8.0 Hz, 1H), 7.27 (d, J=8.4 Hz, 1H), 6.14-6.04 (m, 1H), 5.97-5.85 (m, 1H), 5.76-5.66 (m, 1H), 5.63 (d, J=2.0 Hz, 1H), 5.58-5.41 (m, 4H), 5.30 (dd, J=11.4, 3.1 Hz, 1H), 5.17-4.91 (m, 6H), 4.83 (t, J=7.1 Hz, 1H), 4.65 (t, J=9.1 Hz, 1H), 4.55 (t, J=7.2 Hz, 1H), 4.05 (d, J=6.6 Hz, 1H), 3.73 (t, J=6.6 Hz, 1H), 3.50 (s, 3H), 3.30 (s, 3H), 3.26 (s, 3H), 3.15 (s, 3H), 3.10 (s, 3H), 2.71 (s, 3H), 2.69 (s, 3H), 2.63-2.52 (m, 1H), 2.44-2.34 (m, 1H), 2.23-1.88 (m, 5H), 1.83-1.60 (m, 7H), 1.50-0.69 (m, 54H); ESI MS m/z 1269 [C$_{66}$H$_{113}$N$_{11}$O$_{13}$+H]$^+$; HPLC 92.7% (AUC), $t_R$=19.67 min.

Example 90

Preparation of the Diacetate of Cyclosporin Alkynyl Bromide

To a flask charged with a solution of the acetate of cyclosporin alkyne from Example 78 (33 mg, 0.02 mmol) in acetone (2 mL) was added silver nitrate (3.4 mg, 0.02 mmol) and recrystallized N-bromosuccinimide (36 mg, 0.2 mmol). After 2 h, the reaction was cooled to 0° C. and 5 mL of water were added. The aqueous layer was then extracted with ether (3×75 mL). The combined ethereal layers were washed with water (20 mL) and then brine (20 mL). The organics were dried over anhydrous sodium sulfate and then concentrated under reduced pressure. The crude material was purified by semi-preparative HPLC to yield the diacetate of cyclosporin alkynyl bromide (23 mg, 80%): $^1$H NMR (300 MHz, CDCl$_3$) δ 8.54 (d, J=9.7 Hz, 1H), 8.02 (d, J=6.7 Hz, 1H), 7.67 (d, J=7.7 Hz, 1H), 7.57 (d, J=9.1 Hz, 1H), 6.11-6.00 (m, 1H), 5.69 (dd, J=11.1, 4.0 Hz, 1H), 5.58-5.42 (m, 1H), 5.40-5.13 (m, 5H), 5.07-4.91 (m, 3H), 4.88 (t, J=7.1 Hz, 1H), 4.85 (t, J=9.8 Hz, 1H), 4.57-4.34 (m, 3H), 3.37 (s, 3H), 3.26 (s, 3H), 3.24 (s, 3H), 3.19 (s, 3H), 2.68 (s, 6H), 2.48-2.32 (m, 1H), 2.27-2.12 (m, 3H), 2.11 (s, 3H), 2.02 (s, 3H), 1.98-1.61 (m, 7H), 1.49-0.66 (m, 59H); ESI MS m/z 1406 [C$_{68}$H$_{114}$BrN$_{11}$O$_{15}$+H]$^+$.

Example 91

Preparation of Cyclosporin Alkynyl Bromide

A solution of the diacetate of cyclosporin alkynyl bromide from Example 90 (22.5 mg, 0.02 mmol) in methanol (2 mL) was treated with potassium carbonate (55 mg, 0.40 mmol). The resulting mixture was stirred at room temperature for 4 h, after which it was quenched with a saturated solution of ammonium chloride (10 mL). The aqueous layer was then extracted with ethyl acetate (3×30 mL). The combined organics were washed with brine (20 mL), dried over anhydrous sodium sulfate, and then concentrated under reduced pressure. The crude material was purified by semi-preparative HPLC to yield cyclosporin alkynyl bromide (4.7 mg, 18%): $^1$H NMR (300 MHz, CDCl$_3$) δ 8.09 (d, J=10.0 Hz, 1H), 7.70 (d, J=7.4 Hz, 1H), 7.54 (d, J=8.3 Hz, 1H), 7.27 (d, J=9.9 Hz, 1H), 6.24-6.21 (m, 1H), 5.70 (dd, J=11.0, 3.9 Hz, 1H), 5.49 (d, J=6.6 Hz, 1H), 5.44-5.34 (m, 1H), 5.30 (dd, J=11.8, 3.8 Hz, 1H), 5.13-4.92 (m, 5H), 4.80 (t, J=5.6 Hz, 1H), 4.65 (t, J=8.6 Hz, 1H), 4.51 (t, J=6.8 Hz, 1H), 4.04 (d, J=6.7 Hz, 2H), 3.77 (t, J=6.4 Hz, 1H), 3.49 (s, 3H), 3.30 (s, 3H), 3.26 (s, 3H), 3.15 (s, 3H), 3.11 (s, 3H), 2.70 (s, 3H), 2.69 (s, 3H), 2.57-2.36 (m, 2H), 2.21-1.95 (m, 6H), 1.85-1.56 (m, 7H), 1.50-0.72 (m, 54H); ESI MS m/z 1320 [C$_{64}$H$_{110}$BrN$_{11}$O$_{13}$+H]$^+$; HPLC>99% (AUC), t$_R$=19.68 min.

Example 92

Preparation of the Diacetate of Cyclosporin Alkyne

A flask charged with a solution of cyclopropyl(trimethylsilyl)acetylene (0.1 mL, 0.6 mmol) in triethylamine (3 mL) was cooled to 0° C. Tetrabutylammonium fluoride (0.72 mL, 1 M in THF, 0.72 mmol) was added and the mixture was allowed to stir for 10 min. The ice bath was removed and the flask warmed to room temperature over 30 min. The acetate of trans-cyclosporin vinyl iodide from Example 77 (80 mg, 0.06 mmol) was added followed by copper(I) iodide (5.7 mg, 0.03 mmol) and dichlorobis(triphenylphosphine)palladium(II) (21 mg, 0.03 mmol). After 2 h, the reaction mixture was filtered twice through a microfilter then concentrated under reduced pressure. The crude material was purified by semi-preparative HPLC to afford the diacetate of cyclosporin alkyne (47 mg, 57%): $^1$H NMR (300 MHz, CDCl$_3$) δ 8.54 (d, J=9.5 Hz, 1H), 8.04 (d, J=6.8 Hz, 1H), 7.66 (d, J=7.7 Hz, 1H), 7.57 (d, J=9.1 Hz, 1H), 5.89-5.77 (m, 1H), 5.69 (dd, J=10.9, 3.6 Hz, 1H), 5.57-5.34 (m, 3H), 5.34-5.13 (m, 3H), 5.08-4.94 (m, 3H), 4.86 (t, J=7.1 Hz, 1H), 4.79 (t, J=9.3 Hz, 1H), 4.57-4.33 (m, 3H), 3.37 (s, 3H), 3.26 (s, 3H), 3.23 (s, 3H), 3.19 (s, 3H), 3.13 (s, 3H), 2.68 (s, 6H), 2.44-2.31 (m, 1H), 2.27-2.14 (m, 2H), 2.15 (s, 3H), 2.01 (s, 3H), 1.93-1.63 (m, 7H), 1.57-0.63 (m, 62H); ESI MS m/z 1367 [C$_{71}$H$_{119}$N$_{11}$O$_{15}$+H]$^+$.

Example 93

Preparation of Cyclosporin Alkyne

A solution of the diacetate of cyclosporin alkyne from Example 92 (47 mg, 0.03 mmol) in methanol (2 mL) was treated with potassium carbonate (82 mg, 0.60 mmol). The resulting mixture was stirred at room temperature for 16 h, after which it was quenched with a saturated solution of ammonium chloride (10 mL). The aqueous layer was then extracted with ethyl acetate (3×75 mL). The combined organics were washed with brine (15 mL), dried over anhydrous sodium sulfate, and then concentrated under reduced pressure. The crude material was purified by semi-preparative HPLC to yield cyclosporin alkyne (25 mg, 66%) as a white solid: $^1$H NMR (300 MHz, CDCl$_3$) δ 8.04 (d, J=10.1 Hz, 1H), 7.66 (d, J=7.7 Hz, 1H), 7.44 (d, J=8.3 Hz, 1H), 7.16 (d, J=7.9 Hz, 1H), 6.04-5.92 (m, 1H), 5.70 (dd, J=10.9, 3.6 Hz, 1H), 5.51 (d, J=6.2 Hz, 1H), 5.38-5.31 (m, 1H), 5.28 (dd, J=12.2, 4.0 Hz, 1H), 5.13-4.89 (m, 5H), 4.83 (t, J=7.2 Hz, 1H), 4.64 (t, J=9.7 Hz, 1H), 4.54 (t, J=7.5 Hz, 1H), 4.03 (d, J=6.7 Hz, 2H), 3.70 (t, J=6.2 Hz, 1H), 3.49 (s, 3H), 3.30 (s, 3H), 3.27 (s, 3H), 3.14 (s, 3H), 2.70 (s, 3H), 2.68 (s, 3H), 2.59-2.30 (m, 2H), 2.23-1.95 (m, 6H), 1.85-1.56 (m, 7H), 1.50-0.66 (m, 65H); ESI MS m/z 1283 [C$_{67}$H$_{115}$N$_{11}$O$_{13}$+H]$^+$; HPLC 97.7% (AUC), t$_R$=19.58 min.

Example 94

Preparation of the Acetate of Cyclosporin Alkynyl Thioether

To a flask charged with a solution of the acetate of trans-cyclosporin vinyl iodide from Example 77 (70 mg, 0.05 mmol) in triethylamine (3 mL) was added copper(I) iodide (5.7 mg, 0.03 mmol) followed by dichlorobis(triphenylphosphine)palladium(II) (21 mg, 0.03 mmol) and propargyl ethyl sulphide (0.1 mL, 0.5 mmol). After 5.5 h, an additional 21 mg of dichlorobis(triphenylphosphine)palladium(II) were added and the reaction was left to stir overnight. The reaction mixture was filtered through a microfilter then concentrated under reduced pressure. The crude material was purified by semi-preparative HPLC to afford the acetate of cyclosporin alkynyl thioether (45 mg, 64%): $^1$H NMR (300 MHz, CDCl$_3$) δ 8.54 (d, J=9.7 Hz, 1H), 8.04 (d, J=6.8 Hz, 1H), 7.67 (d, J=7.7 Hz, 1H), 7.62 (d, J=9.1 Hz, 1H), 5.96-5.84 (m, 1H), 5.70 (dd, J=11.1, 3.9 Hz, 1H), 5.57-5.42 (m, 2H), 5.39-5.13 (m, 5H), 5.08-4.97 (m, 3H), 4.86 (t, J=7.2 Hz, 1H), 4.78 (t, J=9.6 Hz, 1H), 4.59-4.33 (m, 3H), 3.37 (s, 3H), 3.26 (s, 3H), 3.23 (s, 3H), 3.19 (s, 3H), 3.13 (s, 3H), 2.69 (s, 3H), 2.68 (s, 3H), 2.45-2.34 (m, 1H), 2.24-2.12 (m, 2H), 2.14 (s, 3H), 2.02 (s, 3H), 1.97-1.83 (m, 5H), 1.76-1.13 (m, 4H), 1.48-0.75 (m, 61H); ESI MS m/z 1401 [C$_{71}$H$_{121}$N$_{11}$O$_{15}$S+H]$^+$.

Example 95

Preparation of Cyclosporin Alkynyl Thioether

A solution of the acetate of cyclosporin alkynyl thioether from Example 94 (45 mg, 0.03 mmol) in methanol (2 mL) was treated with potassium carbonate (83 mg, 0.60 mmol). The resulting mixture was stirred at room temperature for 16 h, after which it was quenched with a saturated solution of ammonium chloride (10 mL). The aqueous layer was then extracted with ethyl acetate (3×75 mL). The combined organics were washed with brine (50 mL), dried over anhydrous sodium sulfate, and then concentrated under reduced pressure. The crude material was purified by semi-preparative HPLC to yield cyclosporin alkynyl thioether (23 mg, 58%) as a white solid: $^1$H NMR (300 MHz, CDCl$_3$) δ 8.04 (d, J=10.0 Hz, 1H), 7.66 (d, J=7.8 Hz, 1H), 7.45 (d, J=8.2 Hz, 1H), 7.15 (d, J=7.8 Hz, 1H), 6.13-5.99 (m, 1H), 5.70 (dd, J=11.1, 4.2 Hz, 1H), 5.53 (d, J=5.9 Hz, 1H), 5.45-5.36 (m, 1H), 5.28 (dd, J=11.7, 3.8 Hz, 1H), 5.14-4.87 (m, 3H), 4.83 (t, J=7.3 Hz, 1H), 4.64 (t, J=9.5 Hz, 1H), 4.55 (t, J=7.5 Hz, 1H), 4.04 (d, J=6.8 Hz, 2H), 3.70 (t, J=6.3 Hz, 1H), 3.50 (s, 3H), 3.40 (s, 3H), 3.30 (s, 3H), 3.27 (s, 3H), 3.15 (s, 3H), 2.73-2.64 (m, 9H), 2.61-2.52 (m, 1H), 2.45-2.34 (m, 1H), 2.24-1.89 (m, 12H), 1.83-1.57 (m, 8H), 1.48-0.75 (m, 53H); ESI MS m/z 1317 [C$_{67}$H$_{117}$N$_{11}$O$_{13}$S+H]$^+$; HPLC 94.0% (AUC), t$_R$=19.80 min.

Example 96

Preparation of the Acetate of Cyclosporin Alkynyl Ether

To a flask charged with a solution of the acetate of trans-cyclosporin vinyl iodide from Example 77 (70 mg, 0.05 mmol) in triethylamine (3 mL) was added copper(I) iodide (5.7 mg, 0.03 mmol) followed by dichlorobis(triphenylphosphine)palladium(II) (21 mg, 0.03 mmol) and methyl propargyl ether (0.05 mL, 0.5 mmol). After 6 h, the reaction mixture was filtered through a microfilter then concentrated under reduced pressure. The crude material was purified by semi-preparative HPLC to afford the acetate of cyclosporin alkynyl ether (52 mg, 75%): $^1$H NMR (300 MHz, CDCl$_3$) δ 8.52 (d, J=9.6 Hz, 1H), 8.01 (d, J=6.8 Hz, 1H), 7.59 (d, J=7.7 Hz, 1H), 7.46 (d, J=9.1 Hz, 1H), 6.06-5.93 (m, 1H), 5.68 (dd, J=10.9, 3.8 Hz, 1H), 5.57-5.42 (m, 2H), 5.37-5.31 (m, 2H), 5.08-4.97 (m, 3H), 5.29 (dd, J=8.9, 2.6 Hz, 1H), 5.15 (t, J=5.6 Hz, 1H), 5.19-4.92 (m, 3H), 4.85 (t, J=7.2 Hz, 1H), 4.78 (t, J=9.6 Hz, 1H), 3.39 (s, 3H), 3.37 (s, 3H), 3.27 (s, 3H), 3.24 (s, 3H), 3.20 (s, 3H), 3.18 (s, 3H), 2.68 (s, 3H), 2.67 (s, 3H), 2.47-2.33 (m, 1H), 2.33-2.13 (m, 3H), 2.10 (s, 3H), 2.10 (s, 3H), 1.95-1.83 (m, 4H), 1.43-0.75 (m, 61H); ESI MS m/z 1371 [C$_{70}$H$_{119}$N$_{11}$O$_{16}$+H]$^+$.

Example 97

Preparation of Cyclosporin Alkynyl Ether

A solution of the acetate of cyclosporin alkynyl ether from Example 96 (52 mg, 0.04 mmol) in methanol (2 mL) was treated with potassium carbonate (111 mg, 0.80 mmol). The resulting mixture was stirred at room temperature for 16 h, after which it was quenched with a saturated solution of ammonium chloride (10 mL). The aqueous layer was then extracted with ethyl acetate (3×75 mL). The combined organics were washed with brine (15 mL), dried over anhydrous sodium sulfate, and then concentrated under reduced pressure. The crude material was purified by semi-preparative HPLC to yield cyclosporin alkynyl ether (37 mg, 73%) as a white solid: $^1$H NMR (300 MHz, CDCl$_3$) δ 8.07 (d, J=9.8 Hz, 1H), 7.67 (d, J=7.6 Hz, 1H), 7.46 (d, J=8.2 Hz, 1H), 7.17 (d, J=8.0 Hz, 1H), 6.19-6.07 (m, 1H), 5.70 (dd, J=10.9, 3.9 Hz, 1H), 5.52 (d, J=6.1 Hz, 1H), 5.49-5.41 (m, 1H), 5.27 (dd, J=11.7, 3.8 Hz, 1H), 5.11-4.91 (m, 6H), 4.83 (t, J=7.4 Hz, 1H), 4.64 (t, J=8.5 Hz, 1H), 4.54 (t, J=7.4 Hz, 1H), 4.20 (d, J=1.8 Hz, 2H), 4.04 (d, J=6.8 Hz, 2H), 3.72 (t, J=6.6 Hz, 1H), 3.50 (s, 3H), 3.39 (s, 3H), 3.30 (s, 3H), 3.27 (s, 3H), 3.15 (s, 3H), 3.11 (s, 3H), 2.70 (s, 3H), 2.68 (s, 3H), 2.53-2.41 (m, 5H), 2.41-2.21 (m, 6H), 2.20-1.92 (m, 6H), 1.85-1.56 (m, 7H), 1.51-0.66 (m, 44H); ESI MS m/z 1287 [C$_{66}$H$_{115}$N$_{11}$O$_{14}$+H]$^+$; HPLC>99% (AUC), t$_R$=18.42 min.

Example 98

Concanavalin A—Stimulated Splenocyte Assay

Male BALB/c mice, at 5 to 7 weeks of age, were sacrificed by CO$_2$ inhalation. Spleens were removed and dissociated by pushing through a nylon cell strainer. The splenocytes were washed in RPMI 1640/5% fetal calf serum (FCS) and pelleted at 400×g. Red blood cells were then lysed by resuspending the cell pellet in ACK lysis buffer (150 mM NH$_4$Cl, 1 mM KHCO$_3$, 0.1 mM EDTA, 3 mL per spleen) for 10 min at room temperature. After pelleting at 400×g, the cells were washed by resuspending in RPMI 1640/5% FCS and repelleting. The cell pellet was resuspended in RPMI 1640/5% FCS and again passed through a cell strainer to remove cell aggregates. The cells were then counted and adjusted to 2×10$^6$ cells/ml in RPMI 1640/10% FCS/50 µM 2-mercaptoethanol. Cell viability was assessed by Trypan blue staining. Cyclosporin A or the test compound and two micrograms of concanavalin A were added to the wells of a 96 well plate, prior to the addition of 2×10$^5$ splenocytes. The cells were cultured in a 37° C. CO$_2$ incubator for 2 days and then pulsed with 1 µCi of [$^3$H] thymidine for 6 hours. Cells were harvested onto filtermats with a TomTec 96 well plate harvester and lysed with H$_2$O. The filtermat and scintillation fluid were sealed in a plastic sleeve. [$^3$H]thymidine incorporation was measured with a Wallac Trilux plate counter. Initial screens were done at a fixed value of 100 ng/ml test compound. IC$_{50}$s were calculated from 7 point concentration-response curves using GraphPad software.

Example 99

Murine Ex Vivo Pharmacodynamic Assay

In vivo immunosuppressive activity can be determined for cyclosporin A and the disclosed cyclosporin analogs, as described below. The concanavalin A-stimulated splenocyte activity can be assessed in vivo using a method previously described by Peterson et al. (Peterson et al., "A Tacrolimus-Related Immunosuppressant with Biochemical Properties Distinct from Those of Tacrolimus," *Transplantation*, 65:10-18 (1998), which is hereby incorporated by reference in its entirety) or a slightly modified version thereof.

Optimal doses of cyclosporin A or an immunosuppressive compound of the present invention (four different doses of test drug plus a control set of animals with no drug) was administered orally or intravenously to male BALB/c or female C57BL mice. Three mice were tested at each dose. Concanavalin A was injected into the tail vein of the mouse at 4 hours after the administration of cyclosporin A or the immunosuppressive compound. One hour after the concanavalin A injection, the mice were euthanized, the spleens were removed under sterile conditions, and the extent of splenocyte proliferation was measured in a similar manner as described in Example 98. The percent inhibition relative to control was plotted graphically versus the dose of the immunosuppressive compound and an ED$_{50}$ value was determined. Each dose-response assay for the compound of the present invention was accompanied by a cyclosporin control at a single dose equal to the ED$_{50}$.

Example 100

Assay for Inhibition of Peptidyl Prolyl Isomerase Activity of Cyclophilin A

The assay for inhibition of peptidyl prolyl isomerase activity of cyclophilin A is a modification of the procedure described by Kofron et al., "Determination of Kinetic Constants for Peptidyl Prolyl cis-trans Isomerases by an Improved Spectrophotometric Assay," *Biochemistry* 30:6127-6134 (1991), which is hereby incorporated by reference in its entirety. Recombinant human cyclophilin A in 50 mM HEPES, 100 mM NaCl pH 8.0 is precooled to 40° C. Test compounds and the cyclosporin positive control are dissolved in dimethyl sulfoxide (DMSO) and introduced over a range of concentrations. Chymotrypsin is then added to a final concentration of 6 mg/ml. The peptide substrate, Suc-Ala-Ala-Pro-Phe-pNA (SEQ ID NO: 1), is dissolved in 470 mM LiCl in trifluoroethanol and then added to 25 µg/ml to initiate the reaction. After rapid mixing, the absorbance at 390 nm is monitored over a 90 second time course.

Example 101

Cellular Assay for Determination of HIV Inhibition

The in vitro anti-HIV activity of compounds of the present invention is measured in established cell line cultures as described by Mayaux et al., "Triterpene Derivatives That Block Entry of Human Immunodeficiency Virus Type 1 Into Cells," *Proc. Natl. Acad. Sci. USA* 91:3564-3568 (1994), which is hereby incorporated by reference in its entirety. The CEM4 cell line was infected with HIV-$1_{Lai}$ strain. The inhibition of HIV replication in the culture is estimated by the measure of the reverse transcriptase (RT) produced in the supernatant. Anti-viral activity is expressed as the $IC_{50}$ RT, the concentration required to reduce replication of HIV by 50%, and is determined by linear regression.

Example 102

Intracellular Replication of the HCV Genome In Vitro

The effect of the cyclosporin compounds of the present invention on the intracellular replication of the HCV genome in vitro, using an HCV replicon system in a cultured human hepatoma Huh7 cell line is determined by the method of Lohmann et al., "Replication of Subgenomic Hepatitis C Virus RNAs in a Hepatoma Cell Line," *Science* 285:110-113 (1999), which is hereby incorporated by reference in its entirety.

Example 103

In Vitro HCV Infection Experiment

The in vitro HCV infection experiment is performed as described by Kato et al., "Replication of Hepatitis C Virus in Cultured Non-Neoplastic Human Hepatocytes," *Jpn. J. Cancer Res.* 87:787-792 (1996), which is hereby incorporated by reference in its entirety, and Ikada et al., "Human Hepatocyte Clonal Cell Lines That Support Persistent Replication of Hepatitis C Virus," *Virus Res.* 56:157-167 (1998), which is hereby incorporated by reference in its entirety.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of treating a mammal with hepatitis C comprising:
administering to the mammal a therapeutically effective amount of a compound having the following formula:

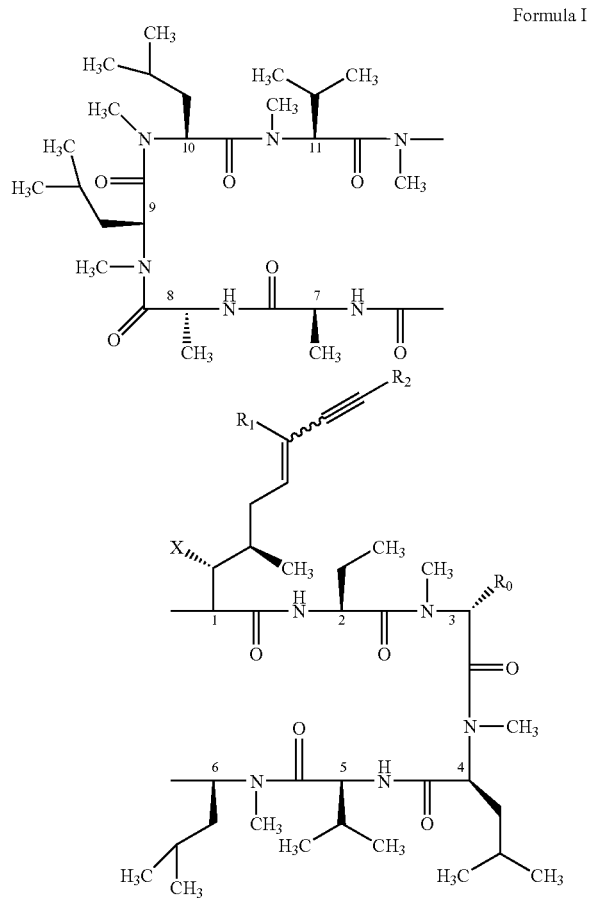

Formula I wherein:
X is OH or OAc;
$R_0$ is H, $CH_2OH$, or $CH_2OR_3$;
$R_1$ is hydrogen, deuterium, or methyl;
$R_2$ is selected from the group consisting of:
 hydrogen;
 halogen;
 $C_1$-$C_6$ saturated or unsaturated, straight or branched carbon chain;
 $C_1$-$C_6$ saturated or unsaturated, straight or branched carbon chain containing a substitution or substitutions selected from the group consisting of deuterium, halogen, nitrogen, sulfur, and silicon;
 $C_1$-$C_6$ saturated or unsaturated, straight or branched carbon chain containing a function group or function groups selected from the group consisting of alcohol, ether, aldehyde, ketone, carboxylic acid, ester, and amide;
 $C_1$-$C_6$ saturated or unsaturated, straight or branched carbon chain containing a function group of oxime or hydrazone;
 $C_1$-$C_6$ saturated or unsaturated, straight or branched carbon chain containing an aryl or a heteroaryl group;
 $C_3$-$C_6$ substituted and unsubstituted cycloalkyl;
 substituted and unsubstituted aryl; and
 substituted and unsubstituted heteroaryl; and
$R_3$ is selected from the group consisting of:
 alkanoyl,
 alkenoyl,
 alkynoyl,
 aryloyl,
 arylalkanoyl,
 alkylaminocarbonyl,
 arylaminocarbonyl,
 arylalkylaminocarbonyl,
 alkyloxycarbonyl,
 aryloxycarbonyl, and
 arylalkyloxycarbonyl,
wherein the compound is a cis geometric isomer, a trans geometric isomer, or a pharmaceutically acceptable salt thereof,
under conditions effective to treat hepatitis C.

2. The method according to claim 1, wherein X is OH or OAc, $R_0$ is H, $CH_2OH$, or $CH_2OAc$, and $R_1$ is H or D.

3. The method according to claim 2, wherein $R_2$ is H.

4. The method according to claim 2, wherein $R_2$ is selected from the group consisting of $CH_3$, $CD_3$, $CH_2CH_3$, and $CH_2CH_2CH_3$.

5. The method according to claim 2, wherein $R_2$ is selected from the group consisting of $CH=CH_2$, $CH=CHCH_3$, $C≡CH$, and $—C≡C—CH_3$.

6. The method according to claim 2, wherein $R_2$ is selected from the group consisting of F, Cl, Br, and I.

7. The method according to claim 2, wherein $R_2$ is cyclopropyl.

8. The method according to claim 2, wherein $R_2$ is selected from the group consisting of $CH_2OH$, $CH(OH)CH_3$, $CH_2OCH_3$, $CH_2OCH_2CH_3$, CHO, and $C(=O)CH_3$.

9. The method according to claim 2, wherein $R_2$ is selected from the group consisting of $CH=N—OCH_3$, $CH=N—OCH_2CH_3$, $CH=N—NHCH_3$, and $CH=N—N(CH_3)_2$.

10. The method according to claim 1, wherein said compound is administered in combination with an interferon.

11. The method according to claim 10, wherein the interferon is interferon α2a or interferon α2b.

12. The method according to claim 10, wherein the interferon is a pegylated interferon.

13. The method according to claim 12, wherein the pegylated interferon is pegylated interferon α2a or pegylated interferon α2b.

14. The method according to claim 1, wherein the compound is non-immunosuppressive.

* * * * *

```
                         SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  Peptide
      substrate
<220> FEATURE:
<221> NAME/KEY: MOD_RES
<222> LOCATION: (1)
<223> OTHER INFORMATION: Xaa at position 1 is alanine (Ala) modified
      with an N-terminal blocking group, succinyl (Suc) Group
<220> FEATURE:
<221> NAME/KEY: MOD_RES
<222> LOCATION: (4)
<223> OTHER INFORMATION: Xaa at position 4 is phenylalanine (Phe)
      modified with a C-terminal blocking group, p-nitroanilide
      (pNA)

<400> SEQUENCE: 1

Xaa Ala Pro Xaa
 1
```